US007557266B2

(12) United States Patent
Lawit et al.

(10) Patent No.: US 7,557,266 B2
(45) Date of Patent: Jul. 7, 2009

(54) ISOLATED POLYNUCLEOTIDE MOLECULES CORRESPONDING TO MUTANT AND WILD-TYPE ALLELES OF THE MAIZE D9 GENE AND METHODS OF USE

(75) Inventors: Shai J. Lawit, Urbandale, IA (US); Suman Kundu, New Delhi (IN); Aragula G. Rao, Urbandale, IA (US); Dwight T. Tomes, Grimes, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 11/736,615

(22) Filed: Apr. 18, 2007

(65) Prior Publication Data

US 2007/0266458 A1 Nov. 15, 2007

Related U.S. Application Data

(60) Provisional application No. 60/834,024, filed on Jul. 28, 2006, provisional application No. 60/793,048, filed on Apr. 19, 2006.

(51) Int. Cl.
*A01H 5/00* (2006.01)
*C12N 5/14* (2006.01)
*C12N 15/63* (2006.01)
*C07H 21/04* (2006.01)

(52) U.S. Cl. .................... 800/295; 435/419; 435/320.1; 536/23.1; 800/320.1; 800/312

(58) Field of Classification Search ........................ None
See application file for complete search history.

(56) References Cited

U.S. PATENT DOCUMENTS

| 6,762,348 | B1 | 7/2004 | Harberd et al. |
| 7,268,272 | B2 | 9/2007 | Harberd et al. |
| 2002/0102695 | A1* | 8/2002 | Silva et al. .................. 435/199 |
| 2004/0034888 | A1 | 2/2004 | Liu et al. |
| 2006/0236419 | A1* | 10/2006 | La Rosa et al. ............. 800/278 |

FOREIGN PATENT DOCUMENTS

WO   WO 99/09174 A1   2/1999

OTHER PUBLICATIONS

Wells (Biochemistry 29:8509-8517, 1990).*
Ngo et al., (The Protein Folding Problem and Tertiary Structure Prediction, K. Merz., and S. Le Grand (eds.) pp. 492-495, 1994).*
Keskin et al. (Protein Science, 13:1043-1055, 2004).*

Thornton et al. (Nature structural Biology, structural genomics supplement, Nov. 2000).*
Guo et al. (PNAS, 101: 9205-9210, 2004).*
Wen, C., et al.; "Arabidopsis RGL1 Encodes a Negative Regulator of Gibberellin Responses"; The Plant Cell (Jan. 2002) 14:87-100; American Society of Plant Physiologists, Rockville, MD, US.
Ashikari, M., et al.; "Rice gibberellin-insensitive dwarf mutant gene Dwarf 1 encodes the alpha-subunit of GTP- binding protein"; Proc. Natl. Acad. Sci. USA (Aug. 1999) 96:10284-10289; National Academy of Sciences; Washington, DC, US.
Alvey, L., et al.; "Della proteins: integrators of multiple plant growth regulatory inputs?"; Physiologia Plantarum (2005) 123:153-160; Munksgaard International Publishers Ltd; Copenhagen, Denmark.
Sun, T.; "Gibberellin signal transduction"; Current Opinion in Plant Biology (2000) 3:374-380; Elsevier Science Ltd; Amsterdam, The Netherlands.
Peng, J., et al.; "The Arabidopsis GAI gene defines a signaling pathway that negatively regulates gibberellin responses"; Genes & Development (1997) 11:3194-3205; Cold Spring Harbor Laboratory Press; Cold Spring Harbor, NY, US.
Fu, X., et al.; "Auxin promotes Arabidopsis root growth by modulating gibberellin response"; Nature (Feb. 13, 2003) 421:740-743; Nature Publishing Group, London, UK.
Ideda, A., et al.; "slender Rice, a Constitutive Gibberellin Response Mutant, Is Caused by a Null Mutation of the SLR1 Gene, an Ortholog of the Height-Regulating Gene GAI/RGA/RHT/D8"; The Plant Cell (May 2001) 13:999-1010; American Society of Plant Physiologists; Rockville, MD, US.
Gale, M., et al.; "Comparative genetics in the grasses"; Proc Natl Acad Sci USA (Mar. 1998) 95:1971-1974; National Academy of Sciences, Washington, DC, US.
Peng, J., et al., "' Green revolution' genes encode mutant gibberellin response modulators"; Nature (Jul. 15, 1999) 400:256-261; Nature Publishing Group, London, UK.
Winkler, R., et al.; "Physiological genetics of the dominant gibberellin-nonresponsive maize dwarfs, Dwarf8 and Dwarf9"; Planta (1994) 193:348; Springer-Verlag; Berlin/Heidelberg. Germany.
Silverston, A., et al.; "Gibberellins and the Green Revolution"; Trends in Plant Science (Jan. 2000) 5(1):1-2; Elsevier, Oxford, UK.
XP-002462715; Database Geneseq Accession No. AJ242530; Jul. 28, 1999; "*Zea mays* partial d8 gene for gibberellin response modulator".
XP-002462716; Database Geneseq Accession No. DQ903073; Sep. 25, 2006; "*Zea mays* dwarf plant9 (d9) mRNA, d9-B73 allele, partial cds."

* cited by examiner

*Primary Examiner*—Phuong T Bui
*Assistant Examiner*—Vinod Kumar

(57) ABSTRACT

The invention provides isolated polynucleotide molecules encoding mutant and wild-type alleles of the maize D9 gene. The invention further provides methods for modifying the growth of plants by decreasing or increasing plant height, altering stem and/or root growth, and involving the use of these isolated polynucleotide molecules, isolated polypeptides, and transformed plants, seeds, and cells.

13 Claims, 38 Drawing Sheets

FIGURE 6

```
            (1) 1         10        20        30        40        50        60        70
   ZM-D9   (1) MKREYQNAGGMDGYRGSSKDKSMAAAAGAGEQEEEVDELLAALGYKVRSSDMADVAQKLEQLEMAMGMGG
MUT1 ZM-D9 (1) MKREYQNAGGSDGYMGSSKDKSMAAAAGAGEQEEEVDELLAALGYKVRSSDMADVAQKLEQLEMAMGMGG

(71) 71        80        90       100       110       120       130       140
   ZM-D9  (71) ACPTADDGFVSHLATDTVHYNPSDLSSWVESMLSELNAPPPPLPPATPAPRLASTSSTVTSGAAAGAGYF
MUT1 ZM-D9(71) ACPTADDGFVSHLATDTVHYNPSDLSSWVESMLSELNTPPPPLPPATPAPRLASTSSTVTSGAAAGAGYF (141) 141       150       160       170       180       190       200       210
   ZM-D9 (141) DLPPAVDSSSSTYALKPIPSPVAAASADPSPDSAREPKRMRTGGGSTSSSSSSSSSMDGGRTSSVVEAA
MUT1 ZM-D9(141) DLPPAVDSSSSTYALKPIPSPVAAASADPSPDSAREPKRMRTGGGSTSSSSSSSSSMDGGRTSSVVEAA (211) 211       220       230       240       250       260       270       280
   ZM-D9 (211) PPATQAANGPAVPVVVVDTQEAGIRLVHALLACAEAVQQENFSAADALVKQIPVLASSQGGAMRKVAAYF
MUT1 ZM-D9(211) PPATQAANGPAVPVVVVDTQEAGIRLVHALLACAEAVQQENFSAADALVKQIPVLASSQGGAMRKVAAYF (281) 281       290       300       310       320       330       340       350
   ZM-D9 (281) GEALARRVYPLRPAPDGSLLDAAFADLLHAHFYESCPYLKFAHFTANQAILEAFAGCRRVHVVDFGIKQG
MUT1 ZM-D9(281) GEALARRVYPLRPAPDGSLLDAAFADLLHAHFYESCPYLKFAHFTANQAILEAFAGCRRVHVVDFGIKQG (351) 351       360       370       380       390       400       410       420
   ZM-D9 (351) MQWPALLQALALRPGGPPSFRLTGVGPPQPDETDALQQVGWKLAQFAHTIRVDFQYRGLVAATLADLEPF
MUT1 ZM-D9(351) MQWPALLQALALRPGGPPSFRLTGVGPPQPDETDALQQVGWKLAQFAHTIRVDFQYRGLVAATLADLEPF (421) 421       430       440       450       460       470       480       490
   ZM-D9 (421) MLRPEGGGDTDDEPEVIAVNSVCELHRLLAQPGTLDKVLGTVRAVRPRIVTVVEQEANHNSGTFLDRFTE
MUT1 ZM-D9(421) MLRPEGDGDTDDEPEVIAVNSVCELHRLLAQPGTLDKVLGTVRAVRPRIVTVVEQEANHNSGTFLDRFTE (491) 491       500       510       520       530       540       550       560
   ZM-D9 (491) SLHYYSTMFDSLEGAGSGSGSGSGSGQPTDASPP---GTDQVMSEVYLGRQICNIVACEGAERTERHET
MUT1 ZM-D9(491) SLHYYSTMFDSLEGAGSGSG-----QPTDASPAAASGTDQVMSEVYLGRQICNIVACEGAERTERHET (561) 561       570       580       590       600       610       628
   ZM-D9 (558) LVQMRGRLGGSGFEPVHLGSNAYKQASTLLALFAGGDYRVEEKDGCLTLGWHTRPLIATSAWRVAAP
MUT1 ZM-D9(555) LVQMRGRLGGSGFEPVHLGSNAYKQASTLLALFAGGDYRVEKKDGCLTLGWHTRPLIATSAWRVAAP
```

```
              (211) 211      220       230       240       250       260       270       280
        ZM-D8(200) SMDGGRTRSSVVEAAPPATQASAAANGPAVPVVVVDTQEAGIRLVHALLACAEAVQQFNFSAALALVKQI
    ZM-D8 MUT(196) SMDGGRTRSSVVEAAPPATQASAAANGPAVPVVVVDTQEAGIRLVHALLACAEAVQQENFSAALALVKQI
   ZM-D8 2023-1(188) SMDGGRTRSSVVEAAPPATQASAAANGPAVPVVVVDTQEAGIRLVHALLACAEAVQQENFSAALALVKQI
     ZM-D8 MPL(95) SMDGGRTRSSVVEAAPPATQASAAANGPAVPVVVVDIQEAGIRLVHALLACAEAVQQENFSAALALVKQI
        ZM-D9(196) SMDGGRTRSSVVEAAPP---ATQAANGPAVPVVVVDTQEAGIRLVHALLACAEAVQQENFSAALALVKQI
   MUT1 ZM-D9(196) SMDGGRTRSSVVEAAPP---ATQAANGPAVPVVVVDTQEAGIRLVHALLACAEAVQQENFSAALALVKQI
         AtGAI(135) KRLKCSNG---------VVETTTATAESTRHVIVDSQENGVRLVHALLACAEAVQKENLTVABALVKQI
         Atgai(109) GGGDTYTTNKRLKCSNGVVETTTATAESTRHVVIVDSQENGVRLVHALLACAEAVQKENLTVABALVKQI
        AtRGA1(178) TSTGTQIGGVIGTIVTTTTTTTAAGESTRSVIILVDSQENGVRLVHALVACAEAIQQNNLTLAEALVKQI
       BR-RGA1(168) SPDSMVTSPG---PAGVIGTIVTTVTESTRPLIIVDSQDNGVRLVHALLACAEAVQSSNLTLAEALVKQI
       BR-RGA2(171) SPDSLVTGTIVTTTTTESTRSVGLAAESTRSMVIVDSQENGVRLVHALLACAEAIQNNDLSIAEALVKQI
      BR-RGA1d(168) SPDSMVTSPG---PAGVIGTIVTTVTFSTRPIIIVDSQDNGVRLVHALLACAEAVQSSNLTIAEALVKQI
       HvSLN1(190) SLGGGAARSSVVEAAPPV--VAAAAAPALPVVVVDTQEAGIRLVHALLACAEAVQQENLSAALALVKQI
        OsGAI(198) SLGGGAERGSVVEAAPPATQGAAAAANAPAVPVVVVDTQEAGIRLVHALLACAEAVQQENFAAALALVKQI
       rht-D1a(193) SSLGGGARSSVVEAAPPV--AAAAAANAIPALPVVVVDTQEAGIRLVHALLACAEAVQQENLSAAEALVKQI
       rht-D1b(129) SSLGGGARSSVVEAAPPV--AAAAAANAIPALPVVVVDTQEAGIRLVHALLACAEAVQQENLSAAEALVKQI (281) 281      290       300       310       320       330       340       350
        ZM-D8(270) PMLAASQGGAMRKVAAYFGEALARRVYRFRPPPDSSLLDAAFADLLHAHFYESCPYLKFAHFTANQAILE
    ZM-D8 MUT(266) PMLAASQGGAMRKVAAYFGEALARRVYRFRPPPDSSLLDAAFADLLHAHFYESCPYLKFAHFTANQAILE
   ZM-D8 2023-1(258) PMLAASQGGAMRKVAAYFGEALARRVYRFRPPPDSSLLDAAFADLLHAHFYESCPYLKFAHFTANQAILE
     ZM-D8 MPL(165) PMLAASQGGAMRKVAAYFGEALARRVYRFRPPPDSSLLDAAFADLLHAHFYESCPYLKFAHFTANQAILE
        ZM-D9(263) PVLAASQGGAMRKVAAYFGEALARRVYRLRPAPDGSLLDAAFADLLHAHFYESCPYLKFAHFTANQAILE
   MUT1 ZM-D9(263) PVLAASQGGAMRKVAAYFGEALARRVYRLRPAPDGSLLDAAFADLLHAHFYESCPYLKFAHFTANQAILE
         AtGAI(196) GPLAVSQIGAMRKVALYFAEALARRIYRLS--PSQSPDFGTSDTILMHFYETCPYLKFAHFTANQAILE
         Atgai(179) GPLAVSQIGAMRKVALYFAEALARRIYRLS--PSQSPDESLSDTILMHFYETCPYLKFAHFTANQAILE
        AtRGA1(248) GCLAASQAGAMRKVAIYFAEALARRIYRLS--PPQNQLDFCLSDTLMHFYETCPYLKFAHFTANQAILE
       BR-RGA1(235) GPLAASQAGAMRKVAIYFAEALARRIYRLS--PPQIQLDFSLSDTILMHFYETCPYLKFAHFTANQAILE
       BR-RGA2(241) GPLAASQAGAMRKVAIYFAEALARRIYRLS--PPQIQLDFSLSDTILMHFYETCPYLKFAHFTANQAILE
      BR-RGA1d(235) GPLAASQAGAMRKVAIYFAEALARRIYRLS--PPQIQLDFSLSDTILMHFYETCPYLKFAHFTANQAILE
       HvSLN1(257) PLLAASQGGAMRKVAAYFGEALARRVFRKPPDSSLLDAAFADLLHAHFYESCPYLKFAHFTANQAILE
        OsGAI(268) PTLAASQGGAMRKVAAYFGEALARRVFR-PAESTLLDAAFADLLHAHFYESCPYLKFAHFTANQAILE
       rht-D1a(261) PLLAASQGGAMRKVAAYFGEALARRVRFRPQPDSSLLDAAFADLLHAHFYESCPYLKFAHFTANQAILE
       rht-D1b(197) PLLAASQGGAMRKVAAYFGEALARRVRFRPQPDSSLLDAAFADLLHAHFYESCPYLKFAHFTANQAILE (351) 351      360       370       380       390       400       410       420
        ZM-D8(340) AFAGCRRVHVVDFGIKQGMQWPALLQALALREGGPPSFRLTGVGPPQELETTDALQQVGWKLAQFAHIIRV
    ZM-D8 MUT(336) AFAGCRRVIIVDFGIKQGMQWPALLQALALREGGPPSFRLTGVGPPQELETTDALQQVGWKLAQFAHIIRV
   ZM-D8 2023-1(328) AFAGCRRVHVVDFGIKQGMQWPALLQALALREGGPPSFRLTGVGPPQELETTDALQQVGWKLAQFAHIIRV
     ZM-D8 MPL(235) AFAGCRRVHVVDFGIKQGMQWPALLQALALREGGPPSFRLTGVGPPQELETTDALQQVGWKLAQFAHIIRV
        ZM-D9(333) AFAGCRRVHVVDFGIKQGMQWPALLQALALREGGPPSFRLTGVGPPQELETTDALQQVGWKLAQFAHIIRV
   MUT1 ZM-D9(333) AFAGCRRVHVVDFGIKQGMQWPALLQALALREGGPPSFRLTGVGPPQELETTDALQQVGWKLAQFAHIIRV
         AtGAI(264) AFQGKKRVHVIDFSMSQGIQWPALMQALALRGGPPVFRLTGIGPPAPDNFDYLLEVGCKLAHFAEAIHV
         Atgai(247) AFQGKKRVHVIDFSMSQGIQWPALMQALALRGGPPVFRLTGIGPPAPDNFDYLLEVGCKLAHFAEAIHV
        AtRGA1(316) AFEGKKRVHVIDFSMNQGIQWPALMQALALREGGPPTFRLTGIGPPAPDNSDHLEVGCKLAQIAEAIHV
       BR-RGA1(303) AFEGKKRVHVIDFSMNQGIQWPALMQALALREGGPPSFRLTGIGPPAADNSDHLEVGCKLAQIAEAIHV
       BR-RGA2(309) AFEGKKRVHVIDFSMNQGIQWPALMQALALREGGPPVFRLTGIGPPAADNSDHLEVGCKLAQIAEAIHV
      BR-RGA1d(303) AFEGKKRVHVIDFSMNQGIQWPATMQALALREGGPPAADNSDHLEVGCKLAQIAEAIHV
       HvSLN1(327) AFAGCRRVHVVDFGIKQGMQWPALLQALALREGGPPSFRLTGVGPPQELETTDALQQVGWKLAQFAHIIRV
        OsGAI(337) AFAGCRRVHVVDFGIKQGMQWPALLQALALREGGPPSFRLTGVGPPQELETTDALQQVGWKLAQFAHIIRV
       rht-D1a(331) AFAGCRRVIIVDFGIKQGMQWPALLQALALREGGPPSFRLTGVGPPQELETTDALQQVGWKLAQFAHIIRV
       rht-D1b(267) AFAGCRRVHVVDFGIKQGMQWPALLQALALREGGPPSFRLTGVGPPQELETTDALQQVGWKLAQFAHIIRV
```

```
                    (631) 631              646
             ZM-D8(615) PLIATSAWRVAAAAAP
         ZM-D8 MUT(611) PLIATSAWRVAAAAAP
        ZM-D8 2023-1(601) PLIATSAWRVAAAAAP
          ZM-D8 MPL(510) PLIATSAWRVAAAAAP
             ZM-D9(613) PLIATSAWRVAAP---
          MUT1 ZM-D9(610) PLIATSAWRVAAP---
             AtGAI(521) PLIATSAWKLSTN---
             Atgai(504) PLIATSAWKLSTN---
            AtRGA1(573) PLITTSAWKLSTAAY-
            BR-RGA1(560) PLITTSAWKLSAVH--
            BR-RGA2(566) PLITTSAWKLSAAH--
           BR-RGA1d(560) PLITTSAWKLSAVH--
            HvSLN1(606) PLIATSAWRLAAP---
             OsGAI(613) PLIATSAWRVAAA---
            rht-D1a(611) PLIATSAWRLAGP---
            rht-D1b(547) PLIATSAWRLAGP---
```

```
             (1)  1         10        20        30        40        50        60        70
MUT1 ZM-D9   (1)  ATGAAGCGCGAGTACCAAAACGCCGGCGGGAGCGACGGCTACATGGGGTCCTCCAAGGACAAGTCGATGG
     ZM-D9   (1)  ATGAAGCGCGAGTACCAAAACGCCGGCGGGAACGACGGCTACAGGGGCTCCTCCAAGGACAAGTCGATGG

(71)  71        80        90        100       110       120       130       140
MUT1 ZM-D9  (71)  CGGCGGCGGCGGGGGCAGGGGAGCAGGAGGAGGAGGTGGACGAGCTGCTGGCGGCGCTCGGGTACAAGGT
     ZM-D9  (71)  CGGCGGCGGCGGGGGCAGGGGAGCAGGAGGAGGAGGTGGACGAGCTGCTGGCCGCGCTCGGGTACAAGGT (141)  141       150       160       170       180       190       200       210
MUT1 ZM-D9 (141)  GCGTTCGTCGGATATGGCGGACGTCGCGCAGAAGCTAGAGCAGCTCCGAGATGGCCATGGGGATGGCGGC
     ZM-D9 (141)  GCGTTCGTCGGATATGGCGGACGTCGCGCAGAAGCTAGAGCAGCTCCGAGATGCCCATGGGCATGGGCGC (211)  211       220       230       240       250       260       270       280
MUT1 ZM-D9 (211)  GCCTGCCCCACCGCTGATCACGGGTTCGTCTCCCACCTCGCCACCGACACCGTGCACTACAATCCCTCCC
     ZM-D9 (211)  GCCTGCCCCACCGCTGATCACGGGTTCGTCTCGCACCTCGCCACGGACACCGTGCACTACAATCCCTCCC (281)  281       290       300       310       320       330       340       350
MUT1 ZM-D9 (281)  ACCTGTCGTCCTGGGTCGAGAGCATGCTATCCGAGCTCAACAGCCCCGCCGCCGCTCCCGCCCGCGAC
     ZM-D9 (281)  ACCTGTCGTCCTGGGTCGAGAGCATGCTGTCCGAGCTCAACGCGCCCCGCCGCCGCTCCCACCCGCGAC (351)  351       360       370       380       390       400       410       420
MUT1 ZM-D9 (351)  GCCGGCACCAAGGCTCGCGTCCACCTCGTCCACCGTCACAAGTGGCGCCGCCGCCGGTGCCGGCTACTTC
     ZM-D9 (351)  GCCGGCACCAAGGCTGGCGTCCACCTCGTCCACCGTCACAAGTGGCGCCGCCGCCGGTGCCGGCTACTTC (421)  421       430       440       450       460       470       480       490
MUT1 ZM-D9 (421)  GATCTCCCGCCCGCCGTCGACTCGTCCAGCAGTACCTACGCTCTGAAGCCGATCCCCTCGCCGGTGGCGG
     ZM-D9 (421)  GATCTCCCGCCCGCCGTCGACTCGTCCAGCAGTACCTACGCTCTGAAGCCGATCCCCTCGCCGGTGGCGG (491)  491       500       510       520       530       540       550       560
MUT1 ZM-D9 (491)  CGGCGTCGGCCGACCCGTCCCCGGACTCGGCGCGGGAGCCCAAGCGCGATGCGAACTGGCGGCGGCAGCAC
     ZM-D9 (491)  CGGCGTCGGCCGACCCGTCCCCGGACTCGGCGCGGGAGCCCAAGCGCATGCGAACTGGCGGCGGCAGCAC (561)  561       570       580       590       600       610       620       630
MUT1 ZM-D9 (561)  GTCGTCGTCCTCTTCCTCGTCGTCATCCATGGACGGCGGCCGCACTAGGAGCTCCGTGGTCGAAGCTGCC
     ZM-D9 (561)  GTCGTCGTCCTCTTCCTCGTCGTCATCCATGGACGGCGGCCGCACTAGGAGCTCCGTGGTCGAAGCTGCC (631)  631       640       650       660       670       680       690       700
MUT1 ZM-D9 (631)  CCGCCGGCGACGCAGGCGGCCAACGGGCCCGCGGTGCCGGTGGTGGTGGTGGACACGCAGGAGGCCGGTA
     ZM-D9 (631)  CCGCCGGCGACGCAGGCGGCCAACGGGCCCGCGGTGCCGGTGGTGGTGGTGGACACGCAGGAGGCCGGGA (701)  701       710       720       730       740       750       760       770
MUT1 ZM-D9 (701)  TCCGGCTGGTGCACGCGCTGCTGGCGTGCGCGGAGGCCGTGCAGCAGGAGAACTTCTCTGCGGCGGACGC
     ZM-D9 (701)  TCCGGCTGGTGCACGCGCTGCTGGCGTGCGCGGAGGCCGTGCAGCAGGAGAACTTCTCTGCGGCGGACGC (771)  771       780       790       800       810       820       830       840
MUT1 ZM-D9 (771)  GCTGGTGAAGCAGATCCCCGTGCTGGCCTCGTCGCAGGGCGGCGCCATGCGCAAGGTCGCCGCCTACTTC
     ZM-D9 (771)  GCTGGTGAAGCAGATCCCCGTGCTGGCCTCGTCGCAGGGCGGCGCCATGCGCAAGGTCGCCGCCTACTTC
```

```
              (841) 841       850       860       870       880       890       900       910
MUT1 ZM-D9    (841) GGCGAGGCGCTCGCCCGGCCGTGTATCGCCTCCGCCCGGCACCGGACGGCTCCCTCCTCGACGCCGCCT
     ZM-D9    (841) GGCGAGGCGCTCGCCCGGCCGTGTATCGCCTCCGCCCGGCACCGGACGGCTCCCTCCTCGACGCCGCCT (911) 911       920       930       940       950       960       970       980
MUT1 ZM-D9    (911) TCGCCGACCTCCTGCACGCGCACTTCTACGAGTCCTGCCCCTACCCTCAAGTTCGCCCACTTCACCGCGAA
     ZM-D9    (911) TCGCCGACCTCCTGCACGCGCACTTCTACGAGTCCTGCCCCTACCCTCAAGTTCGCCCACTTCACCGCGAA (981) 981       990      1000      1010      1020      1030      1040      1050
MUT1 ZM-D9    (981) CCAGGCCATCCTCGAGGCTTTCGCCCGGGTGCCGCCGCGTCCACGTCGTCGACTTCGGCATCAAGCAGGGG
     ZM-D9    (981) CCAGGCCATCCTCGAGGCTTTCGCCCGGGTGCCGCCGCGTCCACGTCGTCGACTTCGGCATCAAGCAGGGG (1051) 1051     1060      1070      1080      1090      1100      1110      1120
MUT1 ZM-D9  (1051) ATGCAGTGGCCGGCTCTCCTCCAGGCCCTCGCCCTCCGCCCCGGTGGCCCCCGTCGTTCCGTCTCACCG
     ZM-D9  (1051) ATGCAGTGGCCGGCTCTCCTCCAGGCCCTCGCCCTCCGCCCCGGCGGCCCCCGTCGTTCCGTCTCACCG (1121) 1121     1130      1140      1150      1160      1170      1180      1190
MUT1 ZM-D9  (1121) GCGTAGGCCCGCCGCAGCCCGACGAGACCGACGCCCTGCAGCAGGTGGGCTGGAAGCTTGCCCAGTTCGC
     ZM-D9  (1121) GCGTAGGCCCGCCGCAGCCCGACGAGACCGACGCCCTGCAGCAGGTGGGCTGGAAGCTCGCCCAGTTCGC (1191) 1191     1200      1210      1220      1230      1240      1250      1260
MUT1 ZM-D9  (1191) GCACACCATCCGCGTCGACTTCCAGTACCGTGGCCTCGTCGCCGCCACGCTCGCTGACCTGGAGCCGTTC
     ZM-D9  (1191) GCACACCATCCGCGTCGACTTCCAGTACCGTGGCCTCGTCGCCGCCACGCTCGCTGACCTGGAGCCGTTC (1261) 1261     1270      1280      1290      1300      1310      1320      1330
MUT1 ZM-D9  (1261) ATGCTGCGACCGGAGGGCGACGGCGACACGGACGACGAGCCCGAGGTGATCGCCGTAAACTCGGTGTGCG
     ZM-D9  (1261) ATGCTGCGACCGGAGGGCGGCGGCGACACGGACGACGAGCCCGAGGTGATCGCCGTAAACTCGGTGTGCG (1331) 1331     1340      1350      1360      1370      1380      1390      1400
MUT1 ZM-D9  (1331) AGCTGCACCGGCTGCTCGCGCAGCCCGGTACACTCGACAAGGTCCTGGGCACCGTGCGCGCGGTGCGGCC
     ZM-D9  (1331) AGCTGCACCGGCTGCTCGCGCAGCCCGGTACACTCGACAAGGTCCTGGGCACCGTGCGCGCGGTGCGCC (1401) 1401     1410      1420      1430      1440      1450      1460      1470
MUT1 ZM-D9  (1401) GAGCATCGTCACCGTGGTGCAGCACCAGCCCAACCACAACTCCGGCACATTCCTCGACCGCTTCACGCAG
     ZM-D9  (1401) GAGGATCGTGACGGTGGTGGAGCAGGAGGCCAACCACAACTCCGGCACATTCCTCGACCGCTTCACGGAG (1471) 1471     1480      1490      1500      1510      1520      1530      1540
MUT1 ZM-D9  (1471) TCGCTGCACTACTACTGTACCATGTTCGACTCCCTCGAGGGCGCCGGCTCGGGCTCCGGCCAGCCGACCG
     ZM-D9  (1471) TCGCTGCACTACTACTGCACCATGTTCGACTCCCTCGAGGGCGCCGGCTCAGGCTCCGGCTCCGGCTCCG (1541) 1541     1550      1560      1570      1580      1590      1600      1610
MUT1 ZM-D9  (1541) AC----GCCTCCTGCCCGGC----GGCGGCCGGGGGCACGGACCAGGTGATGTCCGAGGTGTACCTCGG
     ZM-D9  (1541) GCTCCCCCAGCCGACCGACCCCTCCCGCCCCGCCGCCACCCACCAGGTCATGTCCGAGGTGTACCTCGG (1611) 1611     1620      1630      1640      1650      1660      1670      1680
MUT1 ZM-D9  (1602) GCGGCAGATCTGCAACATCGTGGCGTGCGAGGGCGCCGAGCGCACGGAGCGCCACGAGACGCTGGTCCAG
     ZM-D9  (1611) CCGGCAGATCTGCAACATCGTGGCGTGCGAGGGCGCCGAGCGCACGGAGCGCCACGAGACGCTGGTCCAG
```

```
             (1681) 1681      1690      1700      1710      1720      1730      1740      1750
MUT1 ZM-D9(1672) TGGCGCGGCCGCCTCGGCGGGTCCGGGTTCGAGCCCGTGCACCTGGGCTCCAACGCCTACAAGCAGGCAA
     ZM-D9(1681) TGGCGCGGCCGCCTCGGCGGGTCCGGGTTCGAGCCCGTGCACCTGGGATCCAACGCCTACAAGCAGGCAA (1751) 1751      1760      1770      1780      1790      1800      1810      1820
MUT1 ZM-D9(1742) GCACGCTGCTGGCCCTCTTCGCCGGCGGCGACGGGTACAGGGTGGAGAAGAAGGACGGGTGCCTGACTCT
     ZM-D9(1751) GCACGCTGCTGGCCCTCTTCGCCGGCGGCGACGGGTACAGGGTGGAGGAGAAGGACGGGTGCCTGACTCT (1821) 1821      1830      1840      1850      1860           1878
MUT1 ZM-D9(1812) GGGATGGCATACGCGCCCGCTCATCGCCACCTCGGCGTGGCGCGTCGCCGCTCCGTGA
     ZM-D9(1821) GGGATGGCATACGCGCCCGCTCATCGCCACCTCGGCGTGGCGCGTCGCCGCTCCGTGA
```

| Construct | Rosette Diameter (mm) | Height (mm) | Silique Length (mm) | Silique Width (μm) |
|---|---|---|---|---|
| MS-S2a PRO::GUSINT | 66.1±4.9[a] | 526.5±48.2[a] | 12.4±1.2[a] | 696±87[a] |
| MS-S2a PRO::d8 | 61.5±5.2[b] | 470.1±63.2[b] | 11.4±1.5[b] | 695±116[a] |
| MS-S2a PRO::D8 MPL | 48.0±9.7[cd] | 156.7±34.8[c] | 9.0±1.9[c] | 670±90[ab] |
| MS-S2a PRO::D8 MUT | 44.2±12.7[c] | 118.9±55.4[d] | 9.2±2.3[c] | 689±94[a] |
| MS-S2a PRO::d9 | 64.2±11.7[b] | 462.7±86.5[b] | 11.7±1.9[b] | 692±99[a] |
| MS-S2a PRO::D9 (VARIANT1) | 51.2±9.4[d] | 175.7±68.9[e] | 9.4±1.6[c] | 657±133[b] |

FIGURE 12

Title: ISOLATED POLYNUCLEOTIDE MOLECULES CORRESPONDING TO MUTANT AND WILD-TYPE ALLELES OF THE MAIZE D9 GENE AND METHODS OF USE
Inventors: Lawit et al.
Atty Dkt No. 2075

| Construct | Days to Flowering (*Arabidopsis*) | Above Soil Nodes (maize) |
|---|---|---|
| *MS-S2a PRO::GUSINT* | 41.5±5.6[a] | 8.22±0.74[a] |
| *MS-S2a PRO::d8* | 39.5±4.5[a] | ND |
| *MS-S2a PRO::D8 MPL* | 35.6±7.7[b] | ND |
| *MS-S2a PRO::D8 MUT* | 35.3±6.7[b] | ND |
| *MS-S2a PRO::d9* | 39.9±7.4[a] | 6.90±0.70[b] |
| *MS-S2a PRO::D9 (VARIANT)* | 30.5±4.8[c] | 9.00±0.67[c] |

FIGURE 13

| Chimeric CDS | Rosette Diameter (mm) | Height (mm) | Silique Length (mm) | Silique Width (μm) | Days to Flowering | Rosette Leaves at Flowering |
|---|---|---|---|---|---|---|
| d9 N11S, R15M | 68.4±11.5[a] | 403.2±70.9[a] | 10.6±1.3[a] | 576.9±94.4[ab] | 37.4±3.8[a] | 21.8±3.0[ab] |
| D9 (VARIANT1) S11N, M15R | 65.3±11.9[ab] | 287.1±96.9[b] | 9.8±1.5[ab] | 394.3±157.4[c] | 35.0±5.0[b] | 20.0±4.1[cd] |
| | ALT | - | ALT | - | - | - |
| d9 A108T | 69.5±11.2[a] | 515.0±106.3[c] | 10.3±1.6[a] | 462.8±118.4[de] | 38.2±3.8[a] | 22.8±2.7[a] |
| D9 (VARIANT1) T108A | 55.5±14.3[b] | 306.0±147.9[b] | 10.4±2.3[a] | 482.9±214.7[de] | 35.5±4.9[bc] | 20.1±3.3[cd] |
| | - | - | ALT | ALT | - | - |
| d9 G427D | 59.8±9.1[ab] | 440.7±84.4[ac] | 10.6±1.8[a] | 589.2±106.4[ab] | 36.9±4.4[ac] | 20.9±2.7[bcd] |
| D9 (VARIANT1) D427G | 62.7±16.1[ab] | 331.7±102.7[ab] | 9.6±2.4[ab] | 337.7±122.6[cf] | 34.9±4.4[b] | 19.7±3.4[cd] |
| | ALT | ALT | ALT | - | - | ALT |
| d9 INDEL | 69.9±14.3[a] | 393.1±69.5[a] | 11.7±1.9[c] | 541.2±163.3[ae] | 38.5±3.9[a] | 20.9±3.2[a] |
| D9 (VARIANT1) INDEL | 69.1±15.7[a] | 331.8±139.3[ab] | 9.6±2.0[ab] | 311.9±105.8[f] | 34.2±3.8[b] | 21.0±3.6[bc] |
| | ALT | ALT | - | - | - | ALT |
| d9 E600K | 56.3±14.6[b] | 262.2±81.2[b] | 9.4±1.8[b] | 608.1±76.1[b] | 34.5±4.7[b] | 18.3±3.1[e] |
| D9 (VARIANT1) K597E | 66.1±15.8[ab] | 393.5±65.2[a] | 11.1±1.6[ac] | 496.7±122.7[de] | 38.0±3.9[a] | 22.4±3.1[a] |
| | ALT | REV | REV | REV | REV | REV |

FIGURE 14

ISOLATED POLYNUCLEOTIDE MOLECULES CORRESPONDING TO MUTANT AND WILD-TYPE ALLELES OF THE MAIZE D9 GENE AND METHODS OF USE

CROSS REFERENCE

This utility application claims the benefit U.S. Provisional Application Nos. 60/834,024, filed Jul. 28, 2006, and 60/793,048, filed Apr. 19, 2006, each of which are incorporated herein by reference.

FIELD OF THE INVENTION

The present invention relates to the genetic manipulation of organisms, particularly plants, with genes that control growth and development. The invention further relates to genes that control growth, including homologues and mutant forms, the proteins encoded therefrom and plants transformed with these genes.

BACKGROUND OF THE INVENTION

Dwarf plants have had a major impact on agriculture. Dwarf varieties of wheat are widely used in North America due to both reduced potential for lodging and high yields. There are other benefits that may be realized from the use of dwarf crop plants including reductions in the amounts of pesticides and fertilizers required, higher planting densities, and reduced labor costs.

In view of the current trends of both increasing human population and the decreasing land area suitable for agriculture, increasing agricultural productivity is, and will continue to be, a challenge of paramount importance. Dwarf crop plants have been and will continue to be important components of our agricultural production system. Increased usage of dwarf crop plants may help to meet the agricultural production demands of the future. However, commercially acceptable dwarf varieties are not available for all crops.

In addition to the use of dwarf plants to control plant height, synthetic chemicals are routinely applied to certain economically important plant species to reduce growth. Plant growth regulators known as growth retardants are used to reduce stem elongation in a variety of crops including cotton, grape vines, fruit trees, peanuts, wheat and ornamentals such as azaleas, chrysanthemums, hydrangeas, poinsettias and many bedding plants. All of the commonly used growth retardants are inhibitors of gibberellin biosynthesis and limit stem or shoot growth by reducing elongation. In the United States, the most widely used growth retardant is mepiquat chloride, which is registered for use on cotton. Benefits attributed to the use of mepiquat chloride on cotton include increased yield, improved defoliation, improved stress tolerance, more uniform crop maturity and the ability to harvest earlier. Previously, the growth retardant daminozide was registered for use in the United States on apples, grapes and peanuts under the trademarks ALAR and KYLAR but was removed from use on food crops due to human health concerns. Despite the demands of agricultural producers for a product to replace diaminozide, there are no growth retardants registered for use on grapes, fruit trees and peanuts in the United States. Daminozide, however, is still widely used on certain non-food, plant species.

Uncovering the molecular mechanisms that control plant growth processes such as cell division and cell elongation will likely aid in the development of new plant varieties with reduced stature and new methods for reducing plant growth. Such new plant varieties and methods may provide both farmers and horticulturists with environmentally benign alternatives to the use of synthetic growth-retarding chemicals.

Elongation of plant cells and organs is one of the most critical parameters of plant growth and development. Regulation of this trait in plants, however, is a fairly complicated process, as both external and internal factors influence it. The most important external stimulus is light, with its normally repressible or negative effect on cell elongation (Quail, P. H. (1995) *Science* 268:675-680; Kende, et al., (1997) *Plant Cell* 9:1197-1210). The internal control of cell elongation is mediated by a number of chemicals, normally referred to as plant growth regulators or hormones (Kende, et al., (1997) *Plant Cell* 9:1197-1210). Among the classical plant hormones, auxins and gibberellins (GAs) both promote cell elongation whereas cytokinins and abscisic acid each have been shown to have a negative effect on cell elongation (Kende, et al., (1997) *Plant Cell* 9:1197-1210). Recently, another class of plant growth regulators, named brassinosteroids, has been identified that also dramatically promote plant growth (Yokota, T. (1997) *Trends Plant Sci.* 2:137-143; Azpiroz, et al., (1998) *Plant Cell* 10:219-230; Choe, et al., (1998) *Plant Cell* 10:231-243). However, the mechanisms by which plant hormones act, either singly or in concert, to control cell elongation remains unclear.

One way to gain an understanding of mechanisms that mediate cell elongation is to study mutants in which this aspect of plant growth is compromised (Klee, et al., (1991) *Annu. Rev. Plant Physiol. Plant Mol. Biol.* 42:529-551). Numerous such mutants have been identified across most plant species, including maize, in which more than 25 single-gene mutations that affect plant stature have been characterized (Coe, et al., (1988) In: *Corn & Corn Improvement*, G. F. Sprague (Ed.) Madison, Wis.; Sheridan, W. F. (1988) *Annu. Rev. Genet.* 22:353-385). These dwarf mutants are considered to be GA related, mainly because GA is the only phytohormone whose role in regulating height in maize has been convincingly established (Phinney, et al., (1985) *Curr. Top. Plant Biochem. Physiol.* 4:67-74; Fujioka, et al., (1988) *Proc. Natl. Acad. Sci. USA* 85:9031-9035). Both types of mutants, GA responsive and GA non-responsive, have been found in this collection of maize mutants. While genes for a number of GA-responsive mutants have been cloned and found to be involved in GA biosynthesis (Bensen, et al., (1995) *Plant Cell* 7:75-84; Winkler, et al., (1995) *Plant Cell* 7:1307-1317), less is known about the nature of defects in GA non-responsive maize mutants.

DELLA proteins are keystones of the gibberellin (GA) signal transduction cascade, acting as negative regulators of the GA response that are degraded in the presence of elevated GA concentrations (Silverstone, et al., (2001) *Plant Cell* 10:155-169). DELLA domain proteins are of particular interest because of the gibberellin insensitive dwarf phenotype of their gain-of-function mutants, which were partially responsible for the "Green Revolution" by way of their increase in wheat harvest index (Peng, et al., (1999) *Nature* 400:256-261). Mutations in the N-terminal DELLA domain often cause a dominant GA-insensitive phenotype by greatly increasing the stability of this negative regulator of GA signal transduction (Silverstone, et al., (2001) *Plant Cell* 10:155-169; Gubler, et al., (2002) *Plant Physiol.* 129:191-200; Itoh, et al., (2002) *Plant Cell* 14:57-70). Recently, Griffiths, et al., ((2006) *Plant Cell* 18:3399-3414) demonstrated that both N-terminal regions I and II are required for DELLA protein interaction with *Arabidopsis* GID1a. C-terminal mutations in the conserved GRAS domain typically lead to loss-of-function (Dill, et al., (2004) *Plant Cell* 16:1392-1405), constitutive GA growth response phenotype with the notable exception of a recently identified *Brassica rapa* mutant Brrga1-d (Muangprom, et al., (2005) *Plant Physiol.* 137:931-938) and the barley sln1c mutant (Gubler, et al., (2002) *Plant Physiol.* 129:191-200).

To keep up with the demand for increased agricultural production, new targets are needed for genetically engineering agricultural plants for the improvement of agronomic characteristics. The isolation and molecular characterization of genes encoding proteins that are involved in controlling cell division and elongation in plants will provide new targets for agricultural scientists to manipulate.

BRIEF SUMMARY OF THE INVENTION

Compositions and methods for expressing in plants genes encoding wild-type and variant forms of the DELLA protein encoded by the *Zea mays* D9 (Zm-D9) gene are provided. The compositions comprise isolated polynucleotide molecules encoding wild-type and variant forms of Zm-D9 proteins. The compositions further comprise isolated polynucleotide molecules of the D9 gene of *Zea mays*. The polynucleotide molecules of the invention are useful, for example, in transforming plants for tissue-preferred or constitutive expression of wild-type and variant forms of Zm-D9 proteins, for antisense suppression of the Zm-D9 gene, and for isolating homologous polynucleotide molecules that encode DELLA proteins. Such polynucleotide molecules find use in methods for altering the growth of plants, particularly stem and root growth in plants, more particularly for decreasing or increasing plant height. In one embodiment of the invention, the polynucleotide molecules find use in producing dwarf plants.

Expression cassettes comprising the polynucleotide molecules of the invention are provided. Additionally provided are transformed plants, plant tissues, plant cells and seeds thereof. Isolated proteins encoded by the polynucleotide molecules of the invention are provided.

BRIEF DESCRIPTION OF THE DRAWINGS

FIG. 3A is a DSRED (*Discosoma* sp. red fluorescent protein) EXPRESS control. FIG. 3B is Zm-D8:ACGFP1. FIG. 3C is a merge of A and B. FIG. 3D is a DSRED EXPRESS control. FIG. 3E is Zm-D9:ACGFP1. FIG. 3F is a merge of D and E. The green bars indicate 10 μm in the images.

FIG. 6 is an amino acid sequence alignment of the amino acid sequences of the Zm-D9 (SEQ ID NO: 2) and MUT1 Zm-D9 (SEQ ID NO: 4-5) proteins.

FIG. 7 is a multiple amino acid sequence alignment of DELLA proteins from:
maize (ZM) (ZM-D8—SEQ ID NO: 9, ZM-D8 MUT—SEQ ID NO:10, ZM-D8 2023-1—SEQ ID NO:11, ZM-D8 MPL—SEQ ID NO: 12, ZM-D9—SEQ ID NO: 2, MUT1 ZM-D9—SEQ ID NO: 5)
*Arabidopsis thaliana* (AT) (AtGAI—SEQ ID NO: 13, Atgai—SEQ ID NO: 14, AtRGA1—SEQ ID NO: 15)
*Brassica rapa* (BR) BR-RGA1—SEQ ID NO: 16, BR-RGA2—SEQ ID NO: 17, BR-RGA1d—SEQ ID NO: 18)
*Hordeum vulgare* (HV) (HvSLN1—SEQ ID NO: 19)
*Oryza sativa* (OS) (OsGAI—SEQ ID NO: 20), and
wheat (rht-D1a—SEQ ID NO: 21, rht-D1b—SEQ ID NO: 22).

FIG. 8 is a nucleotide sequence alignment of the nucleotide sequences of Zm-D9 (SEQ ID NO: 1) and MUT1 Zm-D9 (SEQ ID NO: 4).

Figure 9A:
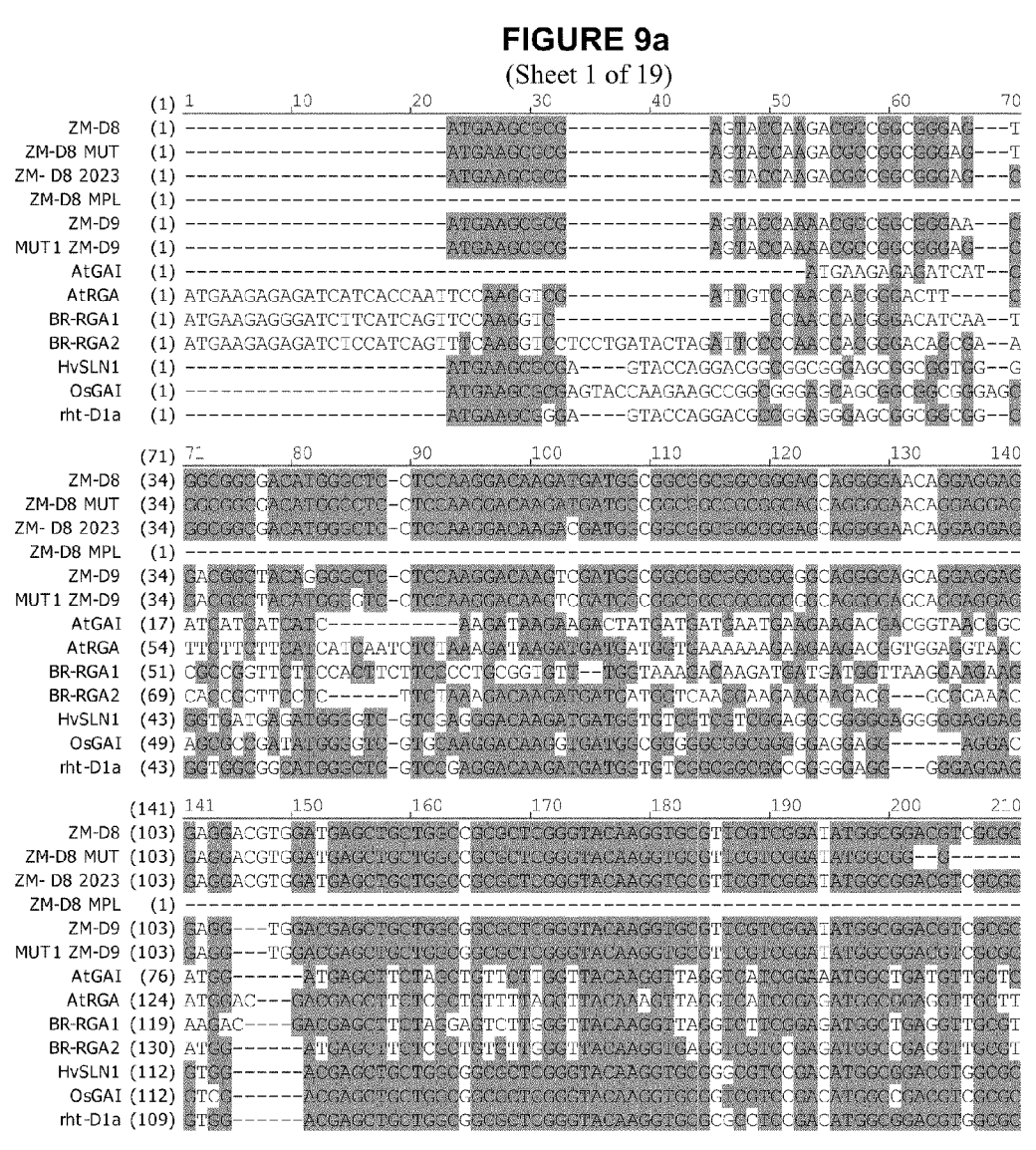
Figure 9B:
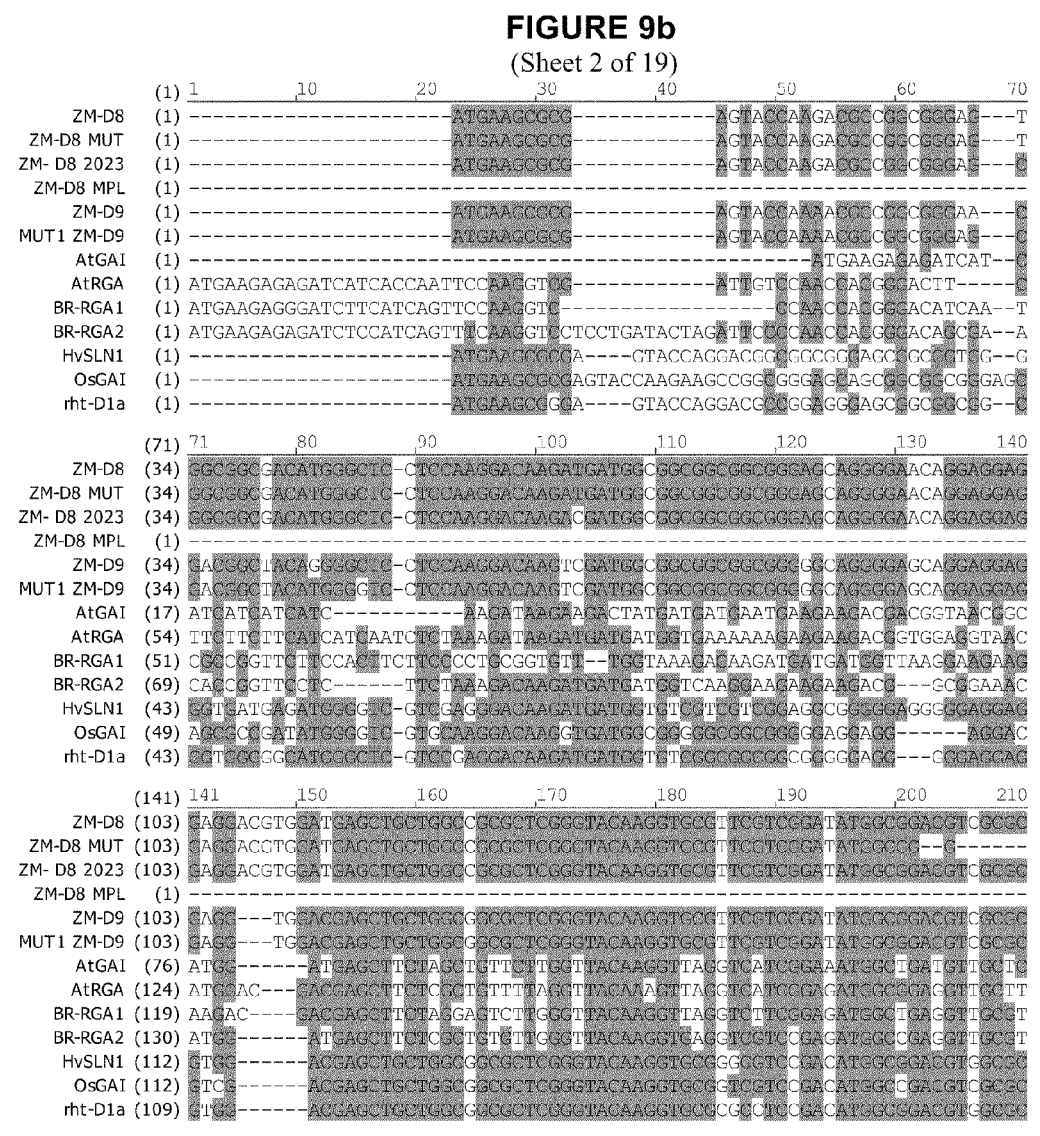
Figure 9C:
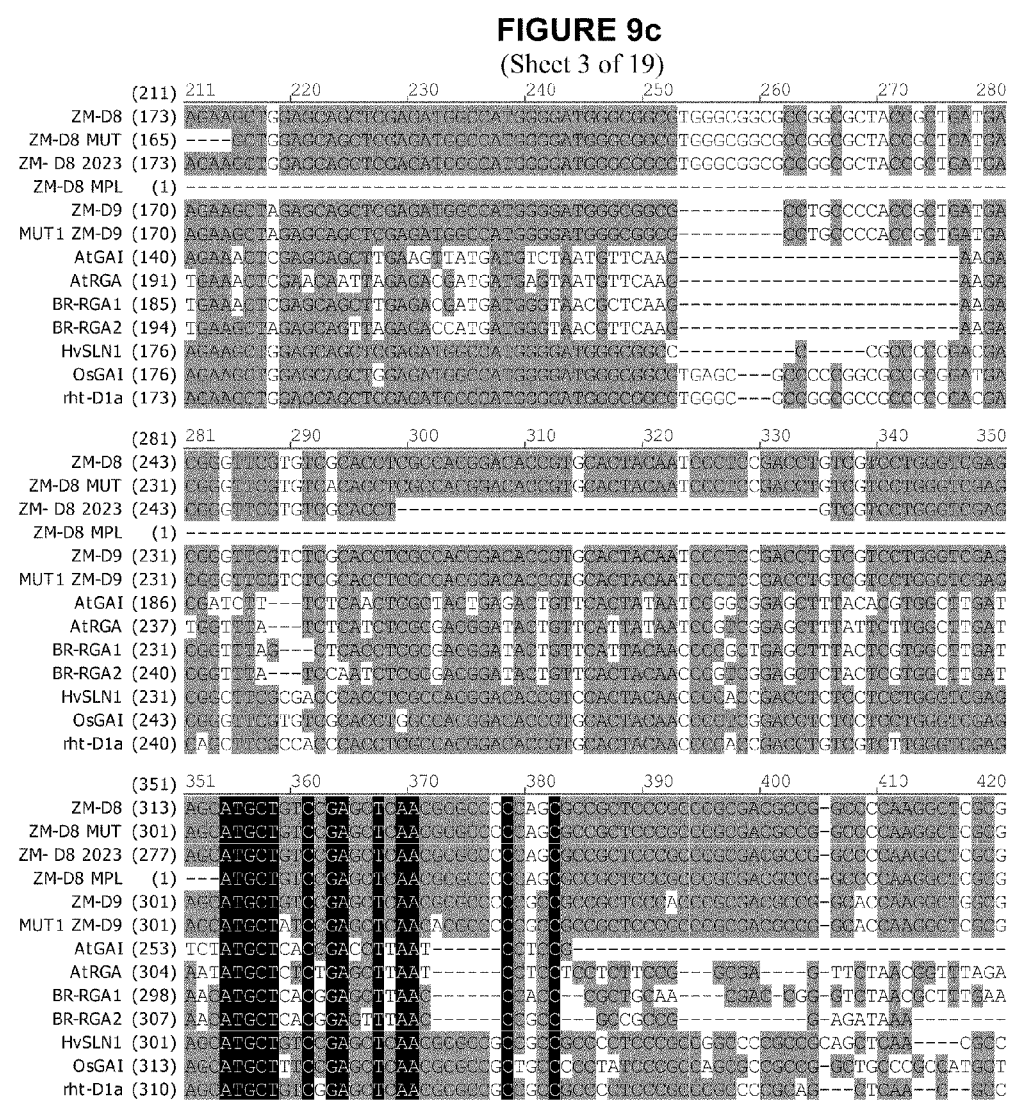
Figure 9D:
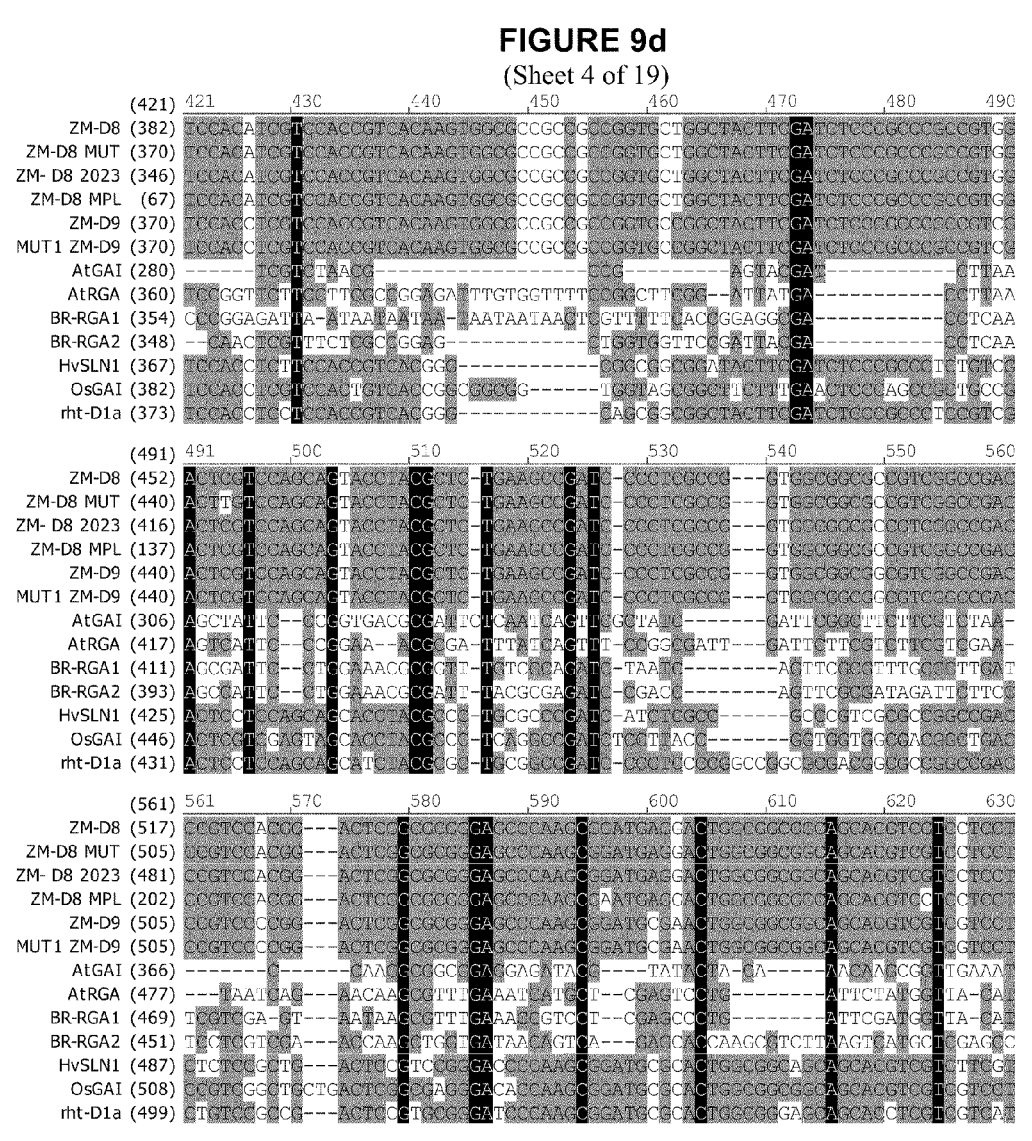
Figure 9E:
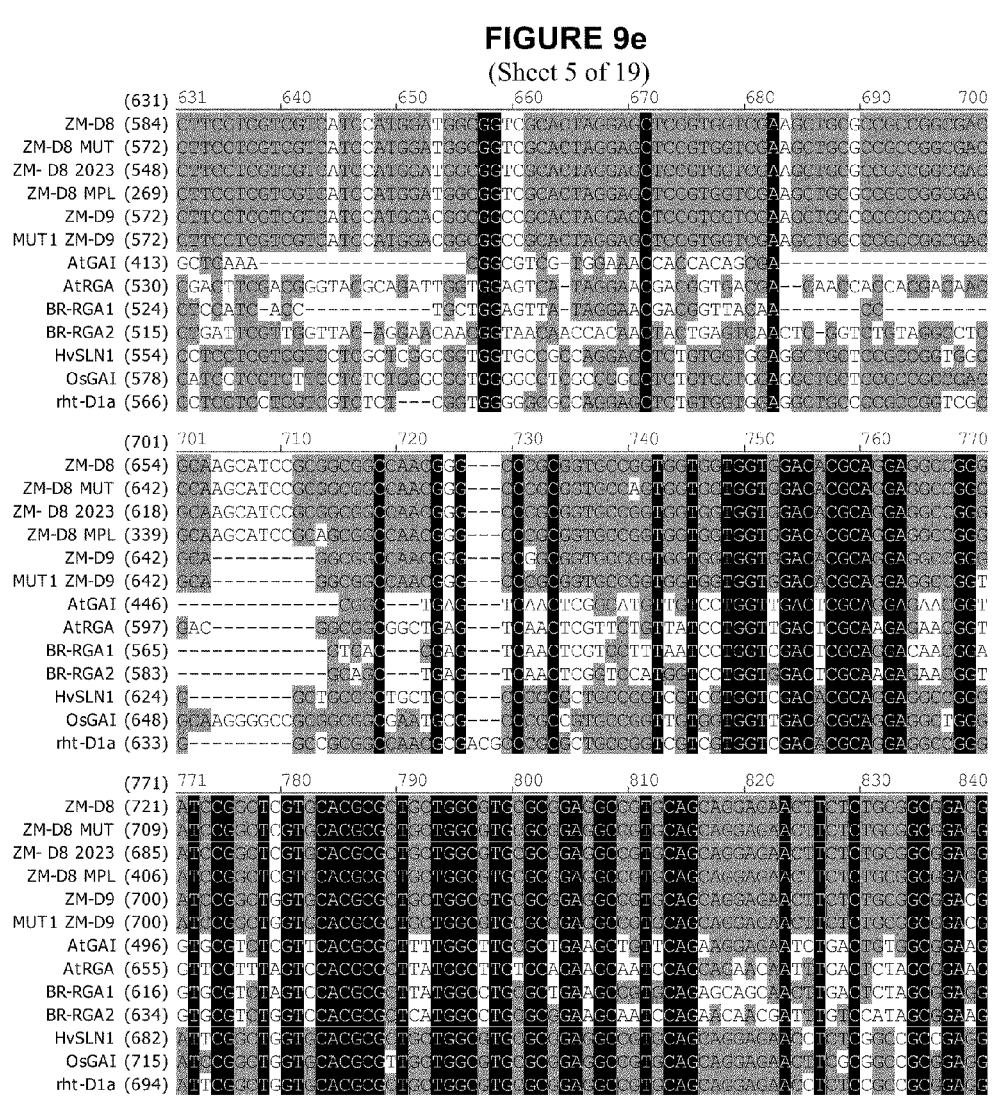
Figure 9F:
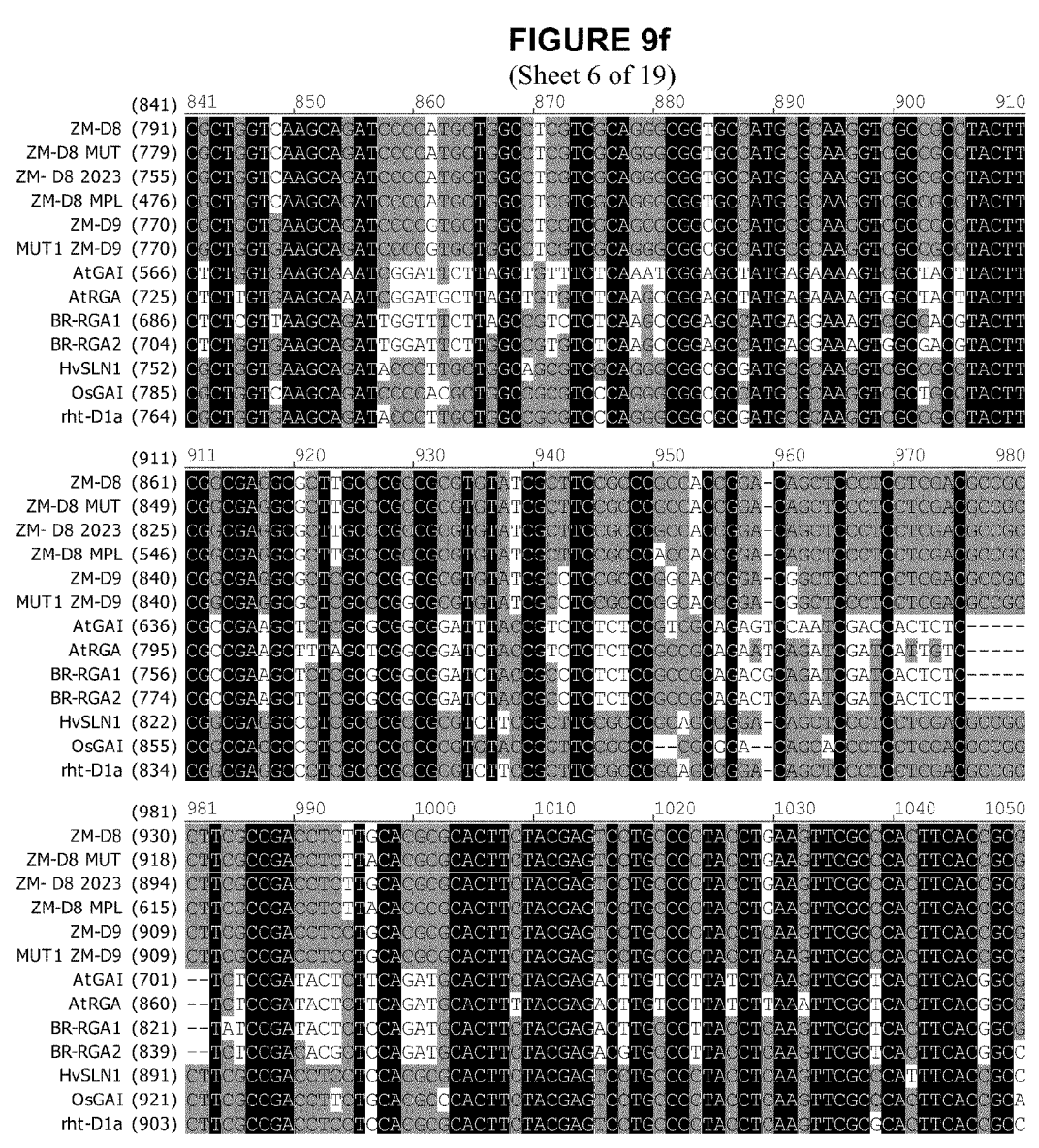
Figure 9G:
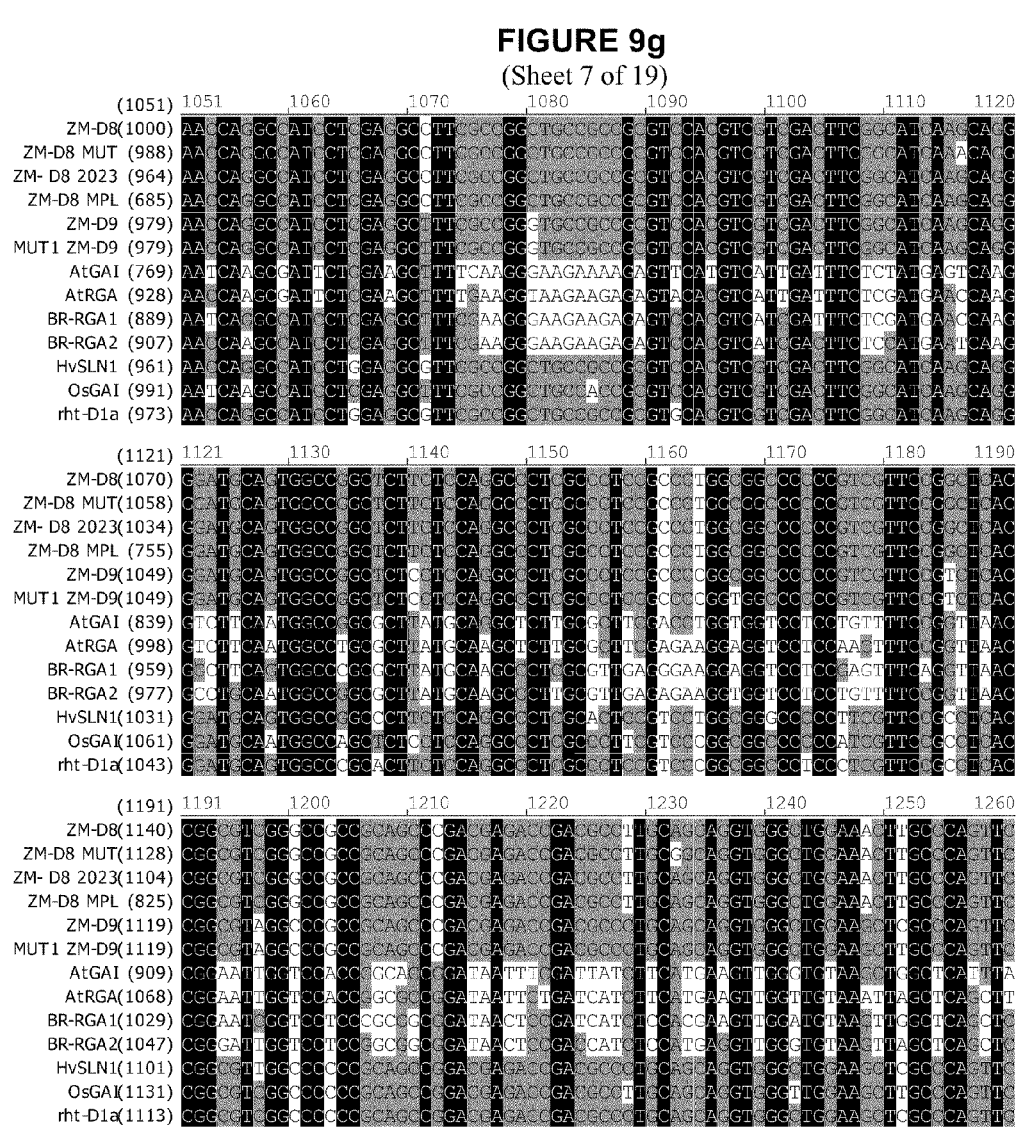
Figure 9H:
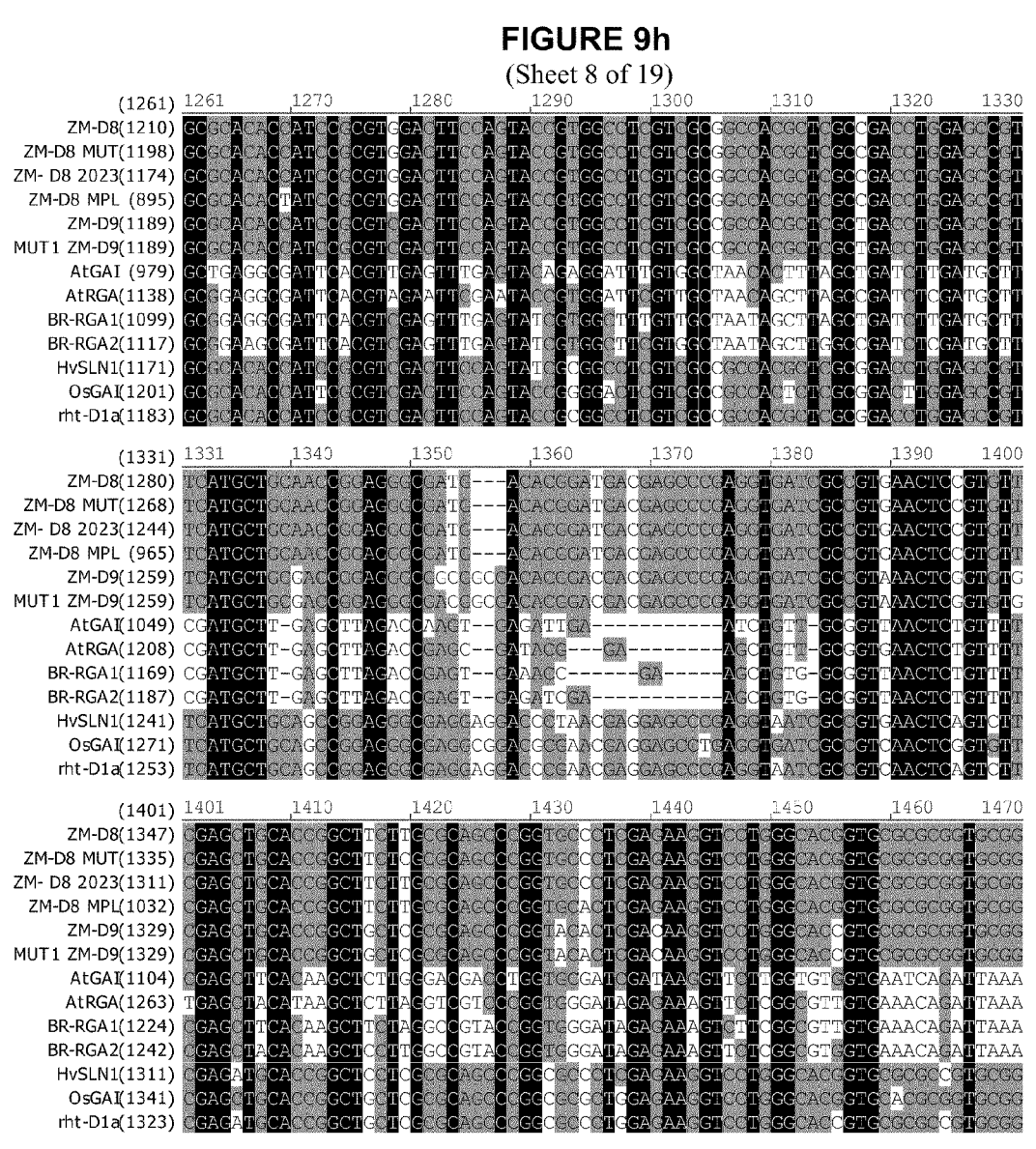
Figure 9I:
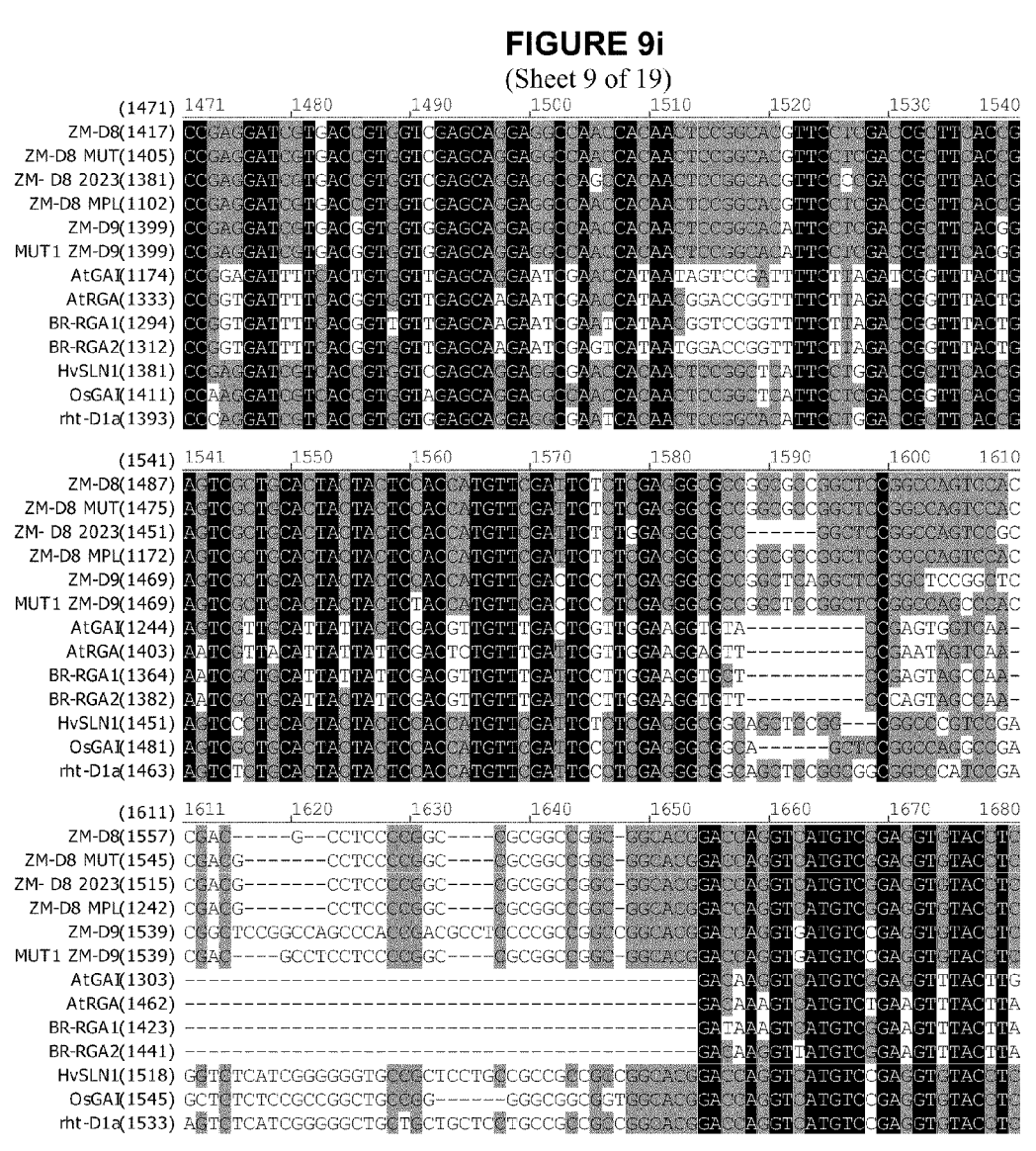
Figure 9J:
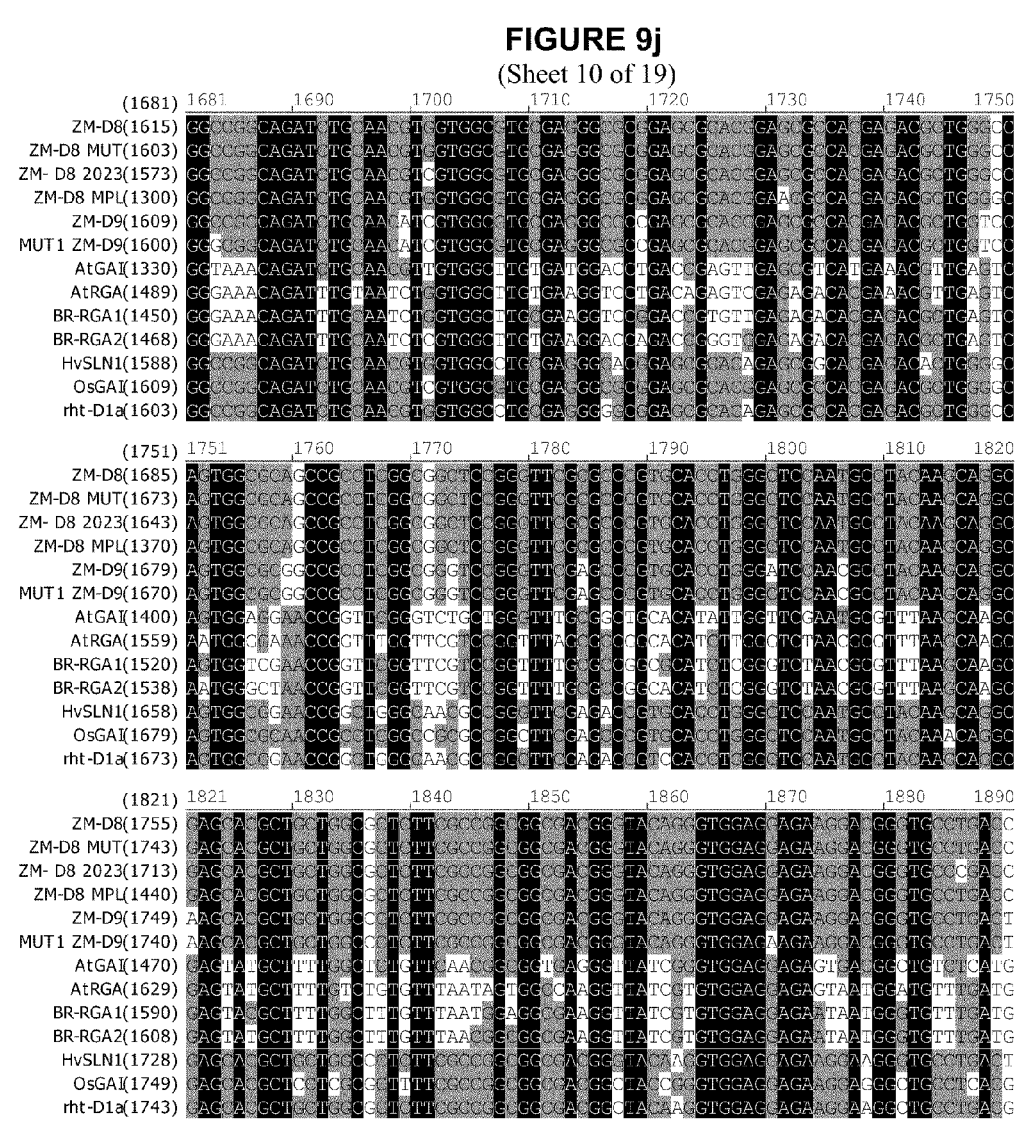
Figure 9K:
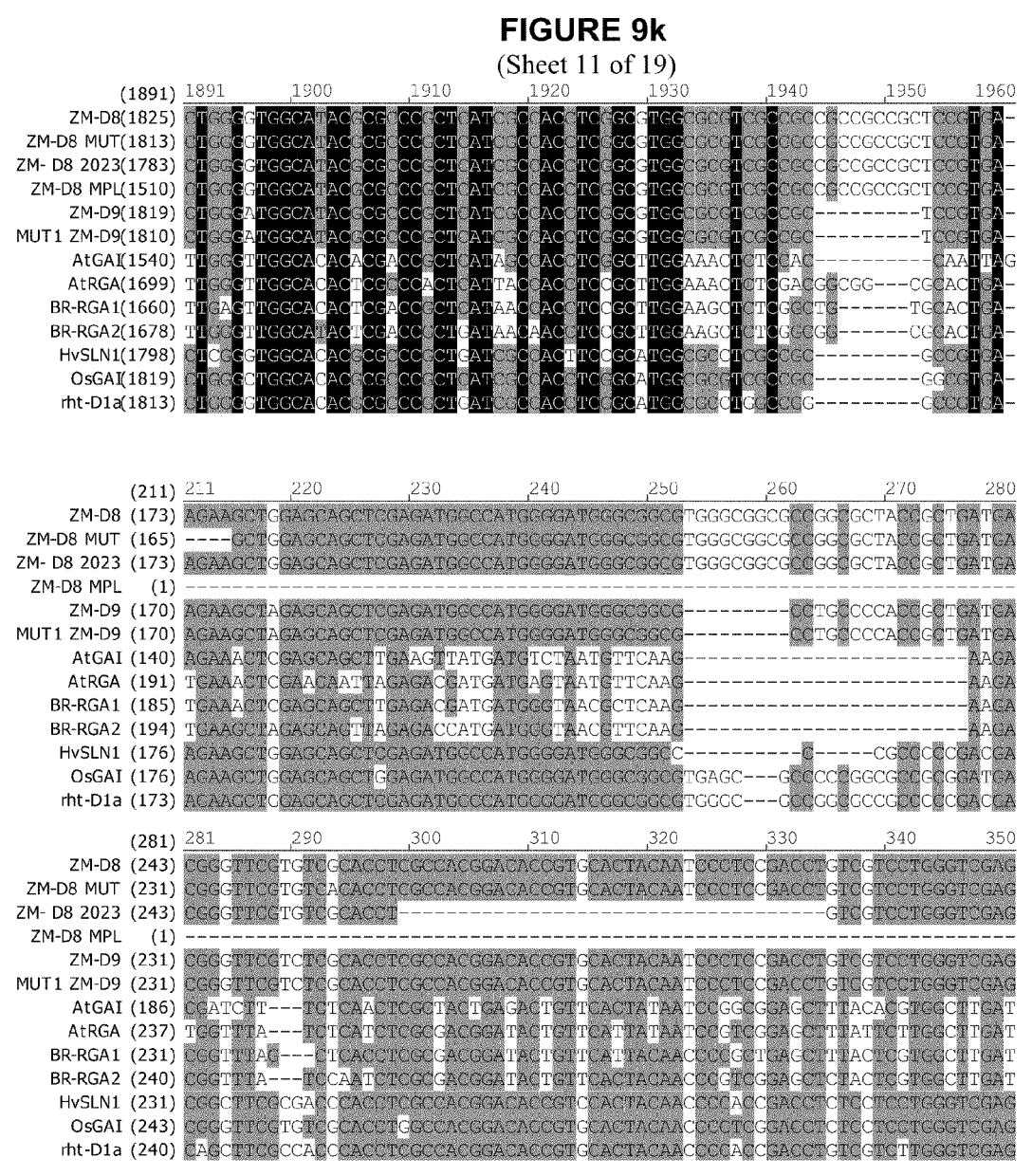
Figure 9I:
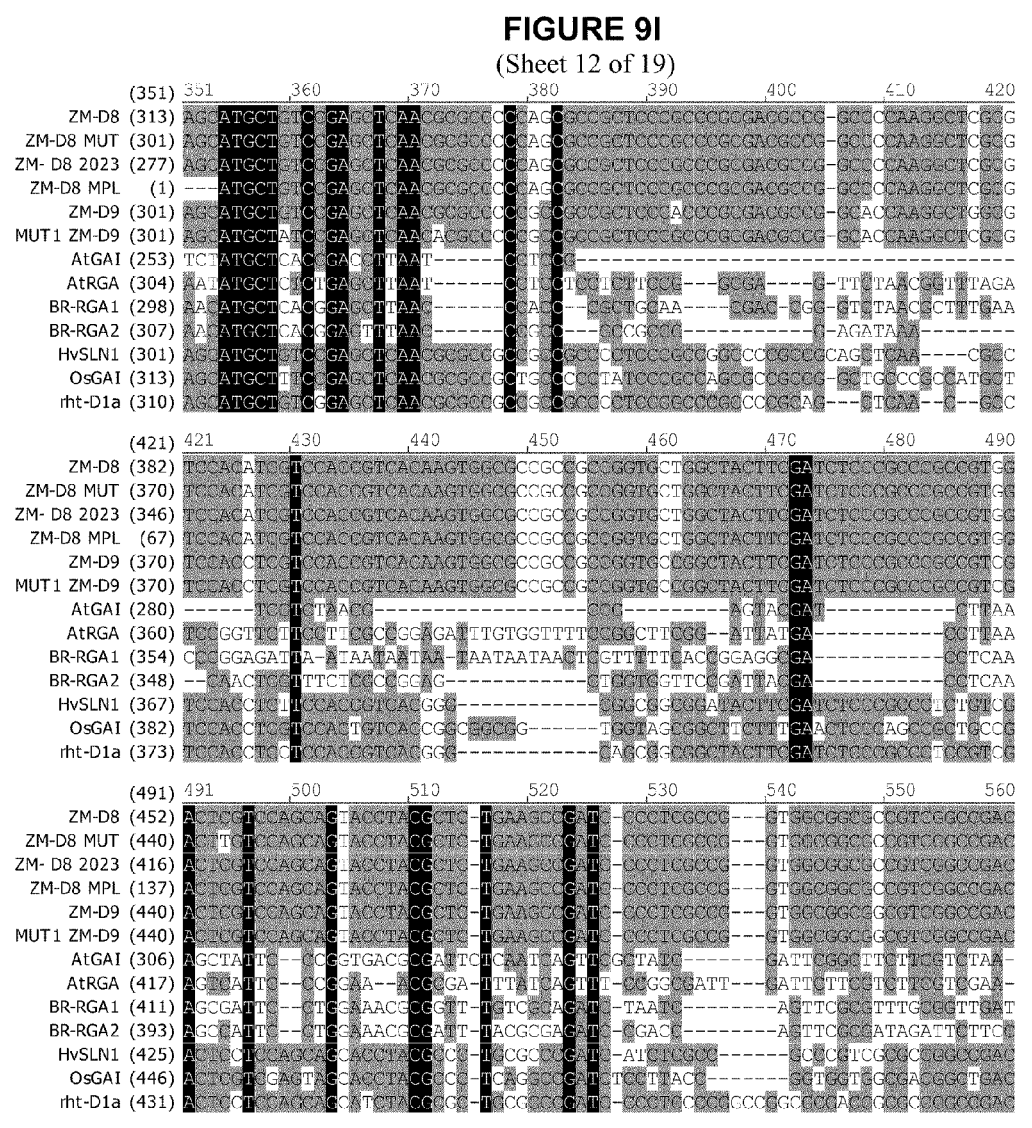
Figure 9M:
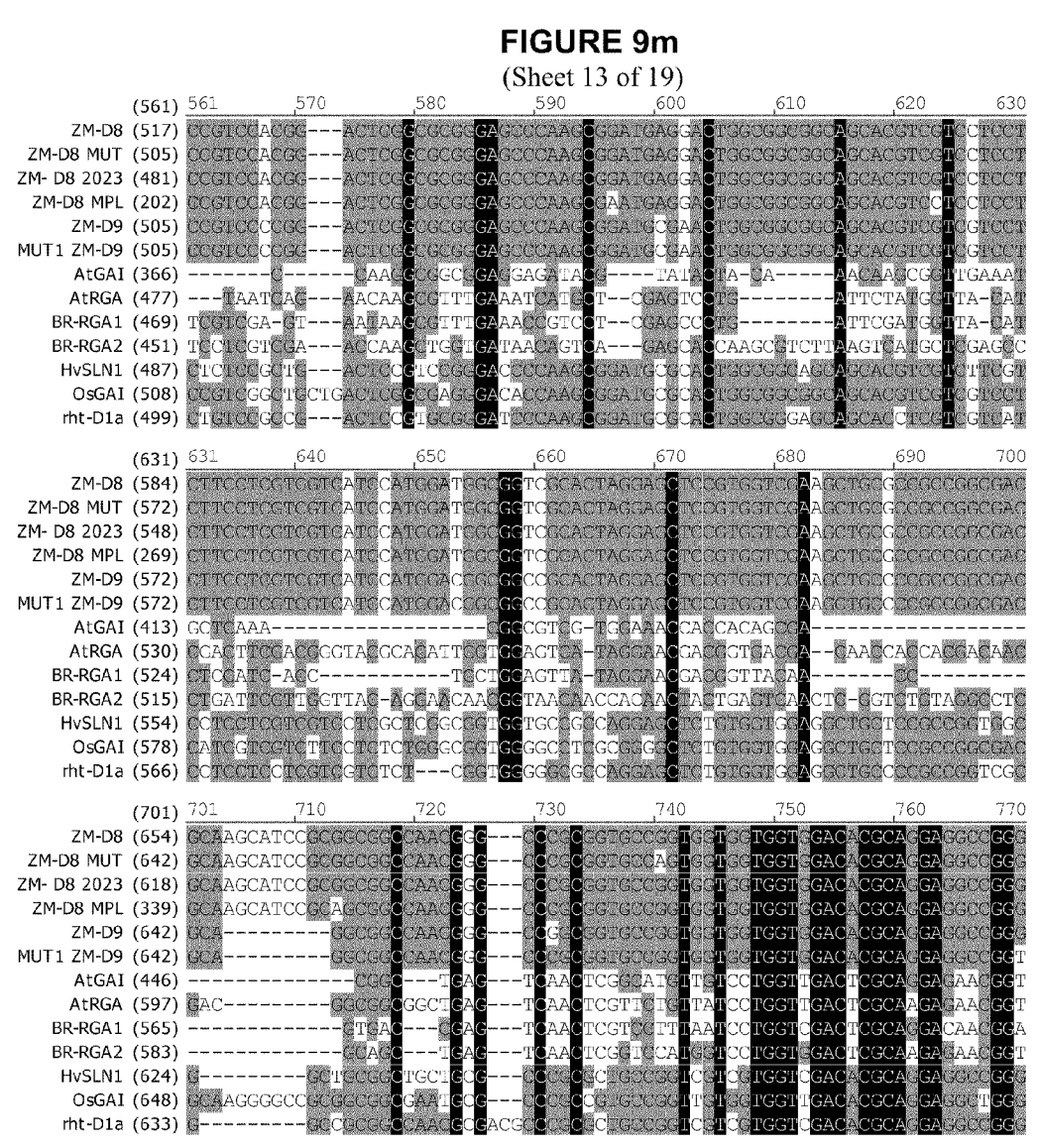
Figure 9N:
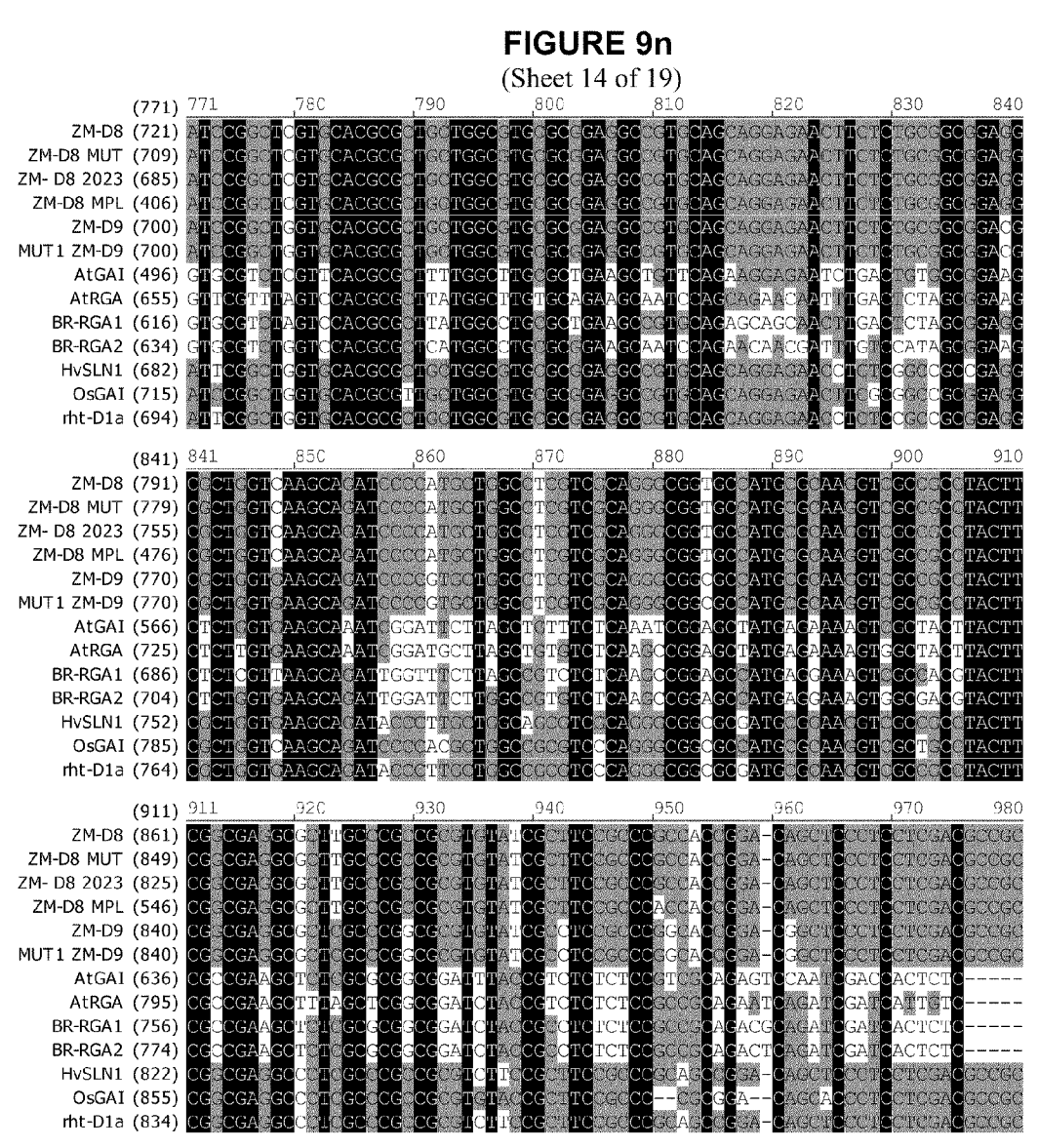
Figure 9O:
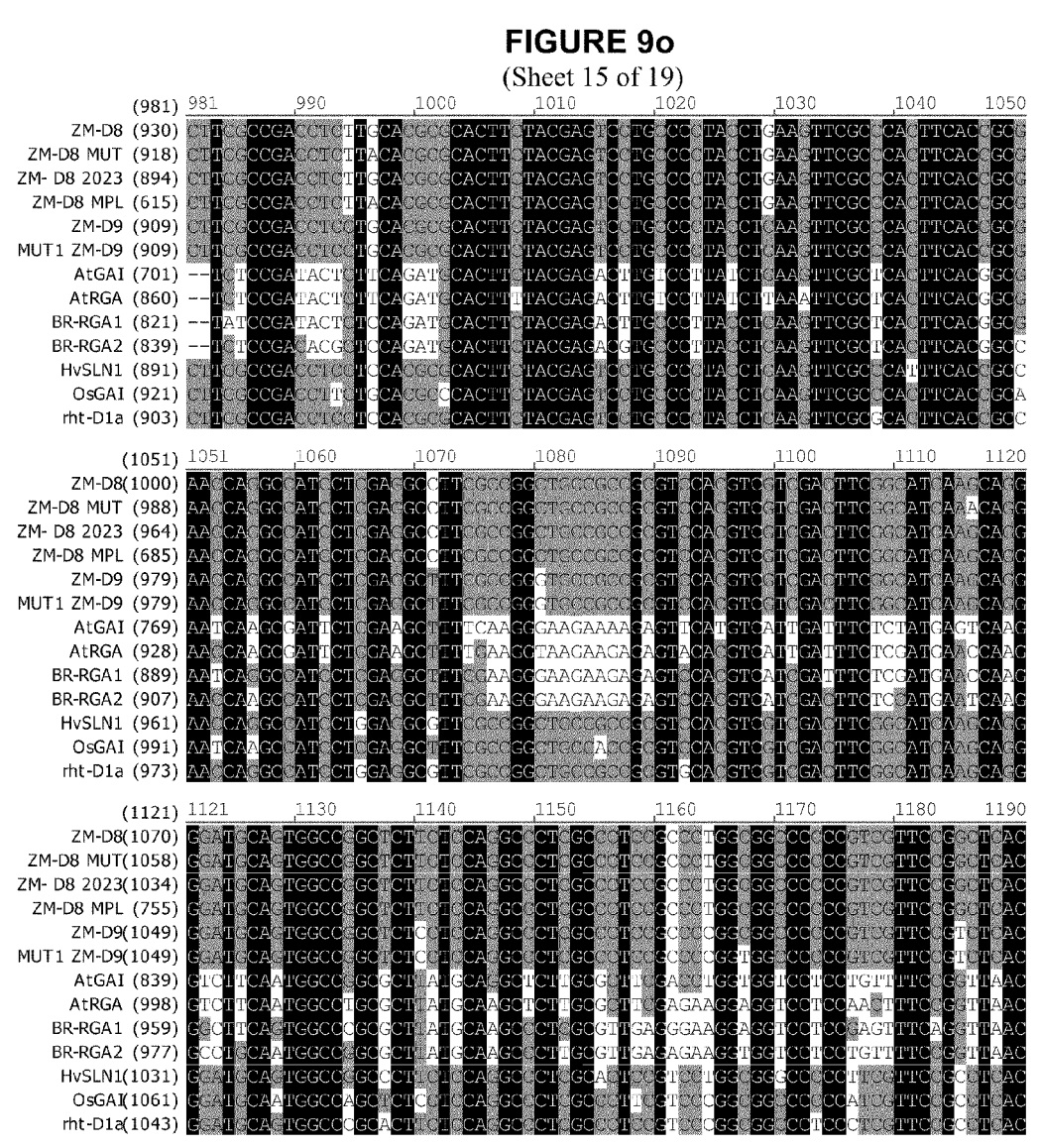
Figure 9P:
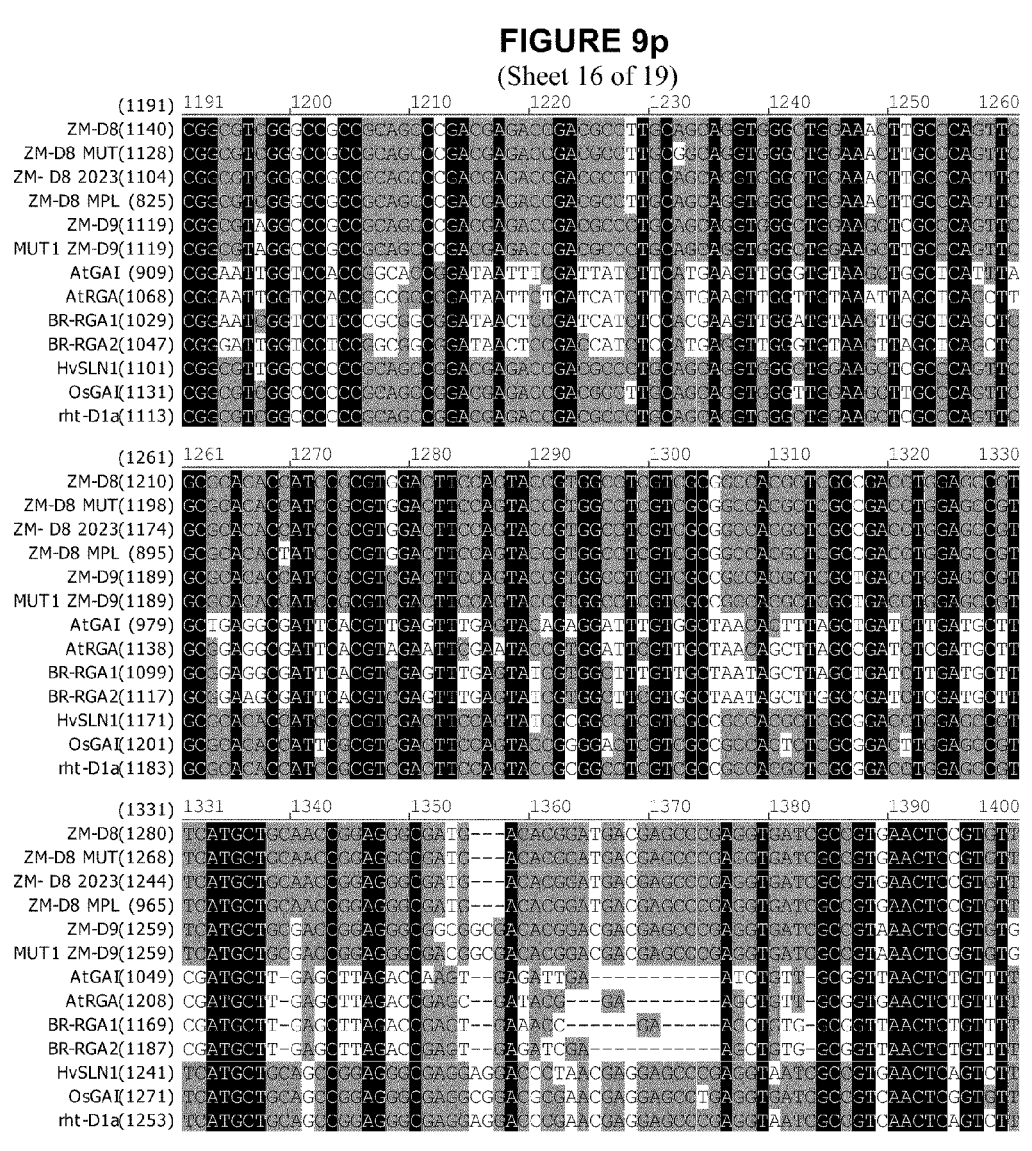
Figure 9Q:
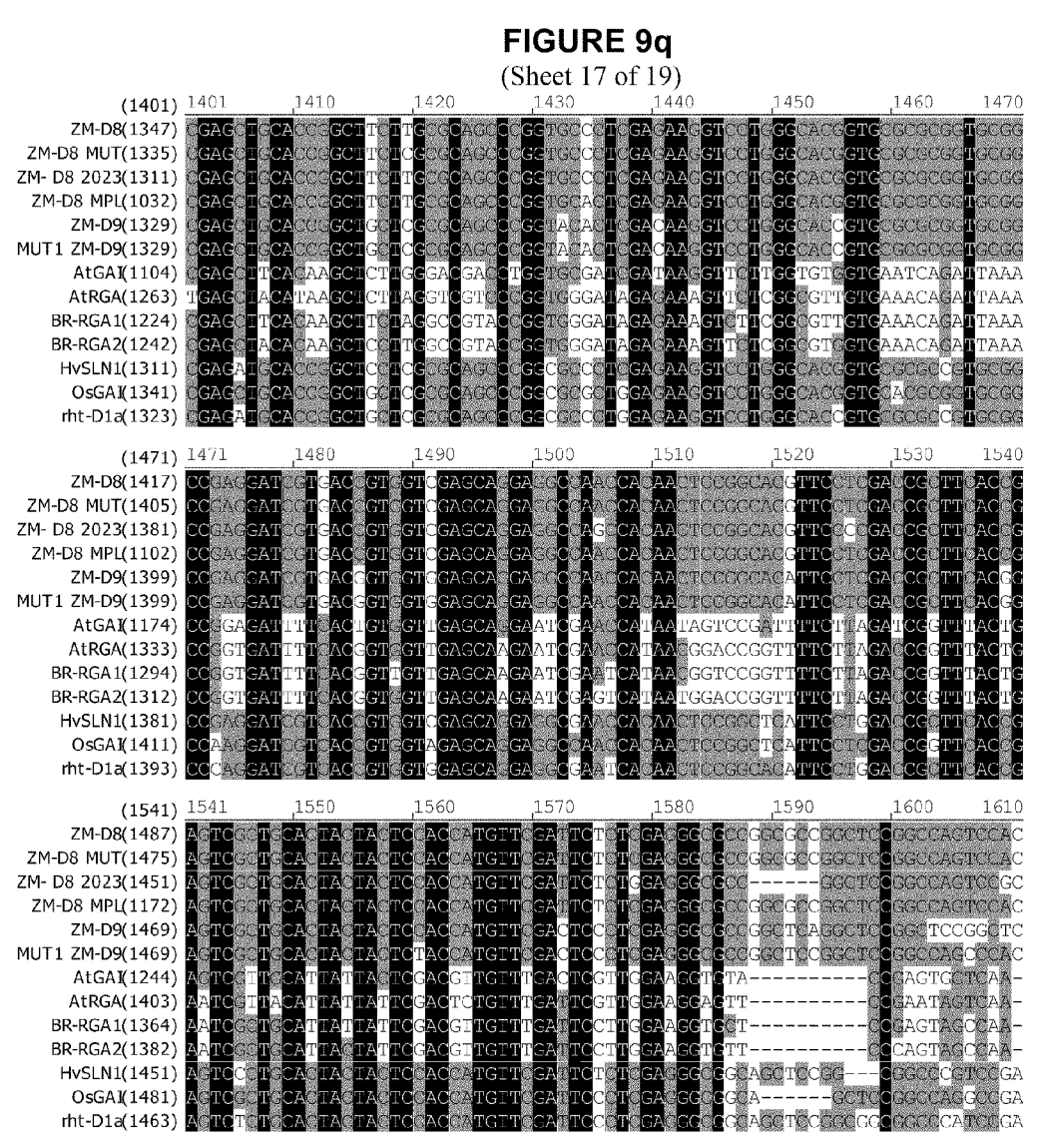
Figure 9R:
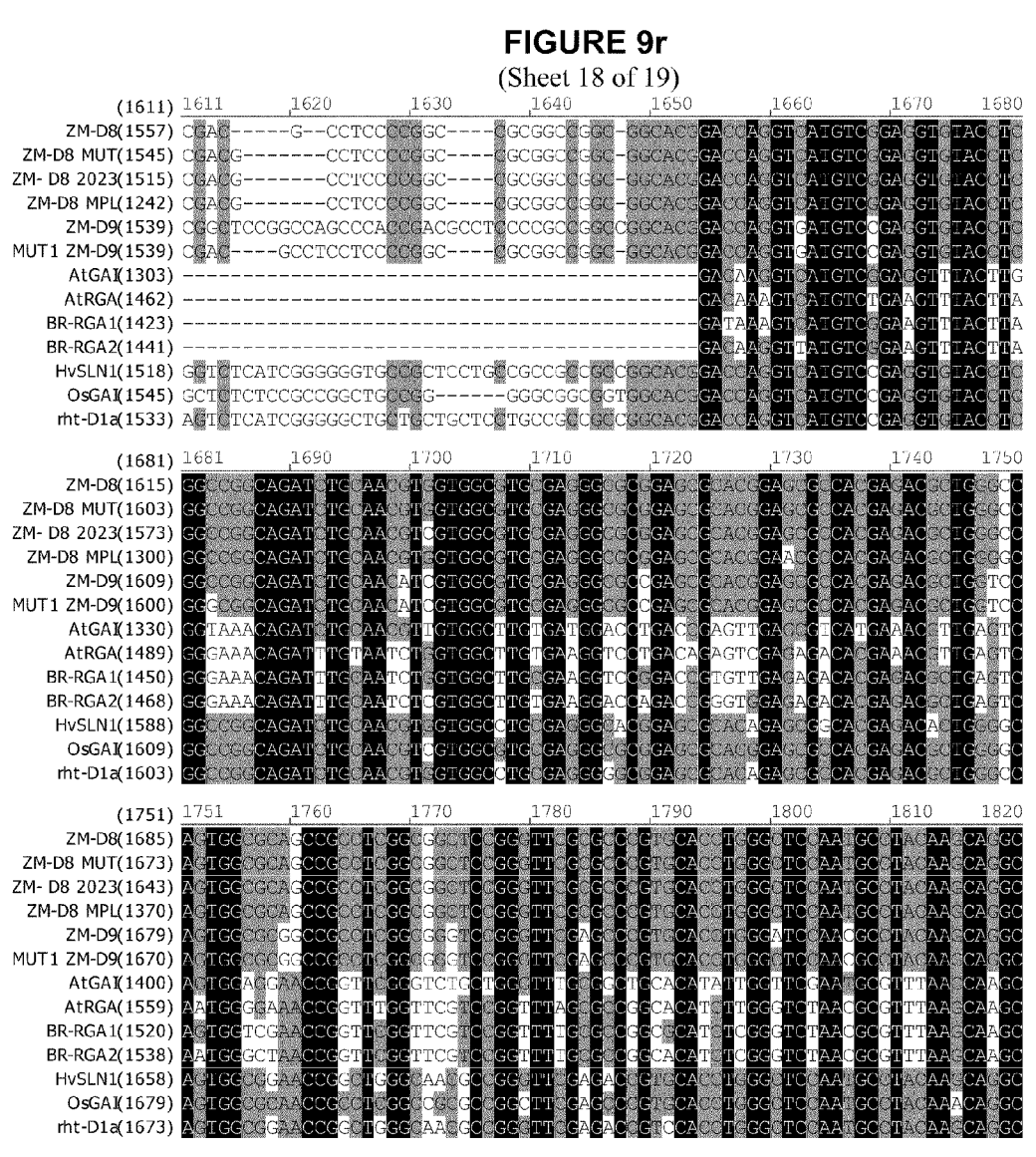
Figure 9S:
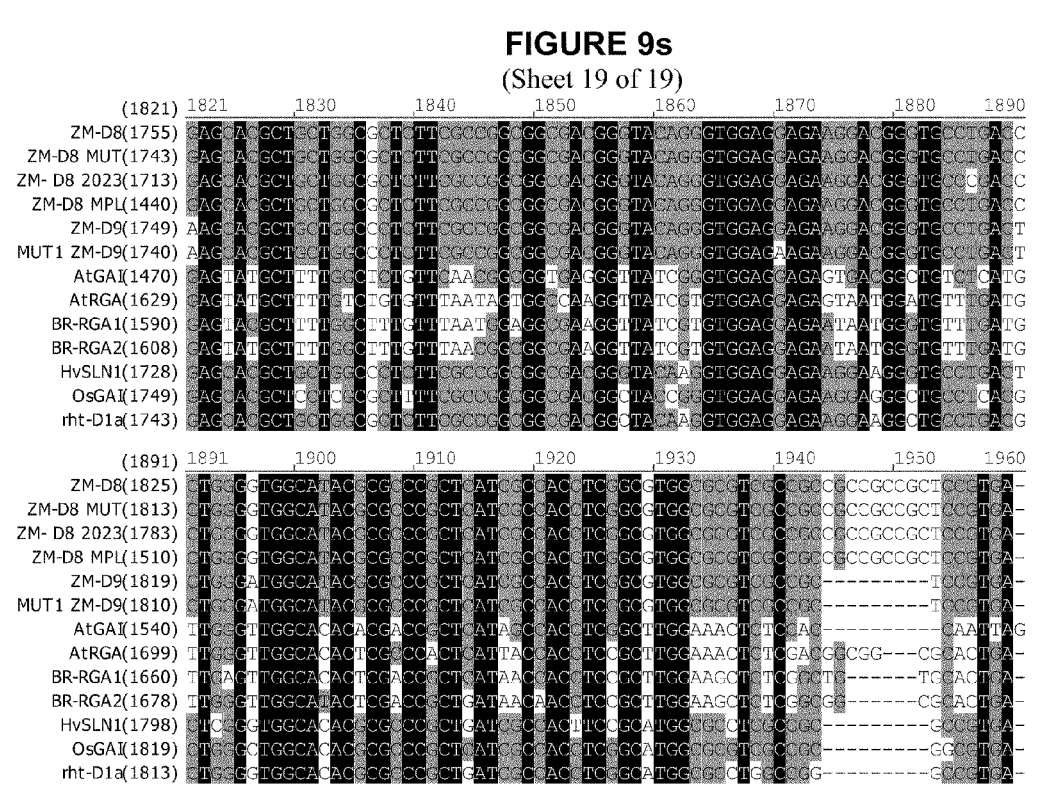

FIG. 9 is a multiple nucleotide sequence alignment of the nucleotide sequences encoding DELLA proteins from:
maize (ZM) (ZM-D8—SEQ ID NO: 23, ZM-D8 MUT—SEQ ID NO:24, ZM-D8 2023—SEQ ID NO:25, ZM-D8 MPL—SEQ ID NO: 26, ZM-D9—SEQ ID NO: 1, MUT1 ZM-D9—SEQ ID NO: 4)
*Arabidopsis thaliana* (AT) (AtGAI—SEQ ID NO: 27, AtRGA—SEQ ID NO: 28)
*Brassica rapa* (BR) (BR-RGA1—SEQ ID NO: 29, BR-RGA2—SEQ ID NO: 30)
*Hordeum vulgare* (HV) (HvSLN1—SEQ ID NO: 31)
*Oryza sativa* (OS) (OsGAI—SEQ ID NO: 32), and
wheat (rht-D1a—SEQ ID NO: 33)

FIG. 12 details morphometric data on T2 *Arabidopsis* plants at growth stage 8.00 (Boyes, et al., (2001) *Plant Cell* 13:1499-1510) expressing cDNAs from naturally occurring d8 and d9 alleles from the MS-S2A promoter. Superscript letters indicate groups that are not significantly different from one another by LSD analysis at 95% confidence level. Data were collected from an average of eight replicates of four independent transformation events.

FIG. 13 presents data on transition to flowering in *Arabidopsis* T2 and GS3x Gaspe Flint maize T0 plants. Superscript letters indicate groups that are not significantly different from one another by LSD analysis at 95% confidence level. These data were collected from an average of eight replicates of four independent events. Maize data were collected from a single replicate of 25 independent transformation events for each construct.

FIG. 14 details the morphometric and flowering time data for d9/D9 domain swap T1 *Arabidopsis*. Note that the superscript letters indicate groups that are not significantly different from one another by LSD analysis at 95% confidence level. ALT=altered; the phenotypic relationship of the alleles are changed by the swapped polymorphism such that differences are no longer significant. REV=reversed; the polymorphism produces a statistically significant reversal of the phenotypic relationship of the alleles. The MS-S2A promoter was used to drive all above coding sequences (CDS). Data were collected from an average of 16.3 independent transformation events per construct. Rosette diameter, height, silique length and silique width were measured at principal growth stage 8.00 (Boyes, et al., (2001) *Plant Cell* 13:1499-1510). Days to flowering and rosette leaves at flowering were measured at principal growth stage 5.10.

SEQUENCE LISTING

Figure 1:
FIG. 1 depicts GA3 non responsive plants (left) and responsive plants (right) segregating for the Zm-D9 MUT1 allele.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleic acid sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleic acid sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth the full-length coding sequence of the wild-type allele of the Zm-D9 gene.

SEQ ID NO: 2 sets forth the Zm-D9 amino acid sequence that is encoded by SEQ ID NO: 1.

SEQ ID NO: 3 sets forth the full-length coding sequence of the wild-type allele of the Zm-D9 gene minus the stop codon. Nucleotides 1-1875 of SEQ ID NO: 3 correspond to nucleotides 1-1875 of SEQ ID NO: 1. If desired, a stop codon can be added to the 3' end of the nucleotide sequence of SEQ ID NO: 3 or any other coding sequence that lacks a stop codon. Such stop codons include, for example, TAA, TAG, and TGA.

SEQ ID NO: 4 sets forth the full-length coding sequence of the mutant allele (MUT1) of the Zm-D9 gene.

SEQ ID NO: 5 sets forth the Zm-D9 amino acid sequence that is encoded by SEQ ID NO: 4.

SEQ ID NO: 6 sets forth the full-length coding sequence of the mutant allele (MUT1) of the Zm-D9 gene minus the stop codon. Nucleotides 1-1866 of SEQ ID NO: 6 correspond to nucleotides 1-1866 of SEQ ID NO: 4.

The amino acid sequence of the d9 INDEL is SEQ ID NO: 7. The D9 INDEL amino acid sequence is SEQ ID NO: 8.

DETAILED DESCRIPTION OF THE INVENTION

The present invention is drawn to compositions and methods for modifying the growth of plants. The compositions include isolated polynucleotide molecules comprising the full-length coding sequences of wild-type and mutant alleles of the maize D9 gene, which is referred to herein as the Zm-D9 gene. Although, Zm-D9 has been described genetically (Winkler and Freeling (1994) *Planta* 193:341-348), the gene has not been previously characterized at the molecular level. The invention further provides the amino acid sequences of the DELLA proteins encoded by the wild-type and mutant alleles of Zm-D9. The methods of the present invention involve transforming plants with polynucleotide molecules encoding wild-type and variant forms of the *Zea mays* DELLA protein encoded by Zm-D9.

The polynucleotide molecules of the present invention are useful for modifying stem or stalk growth in plants so as to produce a transformed plant with a modified stem or stalk. More particularly, the polynucleotide molecules are useful for decreasing or increasing stem or stalk height so as to result in plants with decreased or increased plant height or stature. The polynucleotide molecules also find use in modifying root architecture and other agronomic traits in desirable ways in transformed plants. Such agronomic traits include, but are not limited to, seed set, seed number, harvestable yield, ear length, drought tolerance, water use efficiency, nitrogen use efficiency, lodging resistance, leaf area, nitrogen accumulation, photosynthetic capacity, and carbon and nitrogen partitioning. Thus, the present invention provides transformed plants, plant cells, plant tissues and seeds. The polynucleotide molecules find further use in the construction of expression cassettes for subsequent transformation into plants and plant cells of interest, as probes for the isolation of other D9-like genes, as molecular markers, and the like.

Compositions of the invention include the native wild-type and MUT1 Zm-D9 polynucleotide molecules and variants and fragments thereof. The compositions further include the respective amino acid sequences of the native wild-type and MUT1 Zm-D9 polynucleotide molecules, as well as fragments and variants of such amino acid sequences. The Zm-D9 sequences are set forth in SEQ ID NOS: 1-6. The nucleotide sequences or corresponding antisense sequences find use in modulating the expression of Zm-D9 proteins in a plant or plant cell. That is, the coding sequences can be used to increase the expression while antisense sequences can be used to decrease expression.

DELLA proteins are known to regulate plant cell elongation and can be used to modify, for example, plant cell elongation, plant height and root elongation. See, Itoh, et al., (2002) *Plant Cell* 14:57-70; Achard, et al., (2003) *Plant Cell* 15:2816-2825; and Fu and Harberd (2003) *Nature* 421:740-743; all of which are herein incorporated by reference.

Thus, the polynucleotide molecules of the invention find use in methods of modifying the growth of a plant. In one embodiment of the invention, the polynucleotide molecules of the invention find use in methods of modifying plant growth. Toward this end, the polynucleotide molecules of the invention may be utilized in expression cassettes or polynucleotide constructs operably linked to any one of a variety of plant promoters. Aspects of plant growth that may be impacted by the methods of the invention include, but are not limited to one or more of the following: plant height; stem or stalk height; plant stem or stalk metabolic activity, one or more aspects of root architecture (e.g., root depth, root angle, root branching, number of root tips, nodal root diameter, nodal root volume, root metabolic activity); the size, shape and number of cells and organs; cell division rate; cell elongation rate; the growth rate of the plant, its organs, tissues and cells; timing and location of organ initiation; life span; and the like.

Methods of the invention involve the transformation of plants with polynucleotide molecules of the invention to reduce plant growth. In one embodiment of the invention, a plant is transformed with a MUT1 Zm-D9 polynucleotide molecule operably linked to a promoter that drives expression in a plant. Such a polynucleotide molecule comprises the nucleotide sequence set forth in SEQ ID NO: 4 or 6, a nucleotide sequence encoding the polypeptide set forth in SEQ ID NO: 5, or a fragment or variant of any of such polynucleotide molecules that encodes a polypeptide retaining substantially the same biological activity as the native MUT1 Zm-D9 polypeptide. By expressing such a MUT1 Zm-D9 polynucleotide molecule in plant, a plant of reduced stature, a dwarf plant, can be produced.

Thus, the methods of the invention find use in producing dwarf varieties of crop plants. Dwarf crop plants having improved agronomic characteristics, such as, for example, reduced potential for lodging, increased water-use efficiency, reduced life cycle, increased harvest efficiency and increased yield per unit area are obtained by these methods.

By "dwarf" is intended to mean atypically small. By "dwarf plant" is intended to mean an atypically small plant. Generally, such a "dwarf plant" has a stature or height that is reduced from that of a typical plant by about 5%, 10%, 15%, 20%, 25%, 30%, 35%, 40%, 45%, 50%, 55%, 60% or greater. Generally, but not exclusively, such a dwarf plant is characterized by a reduced stem, stalk or trunk length when compared to the typical plant.

The invention encompasses isolated or substantially purified polynucleotide molecule or protein compositions. An "isolated" or "purified" polynucleotide molecule or protein, or biologically active portion thereof, is substantially or essentially free from components that normally accompany or interact with the polynucleotide molecule or protein as found in its naturally occurring environment. Thus, an isolated or purified polynucleotide molecule or protein is substantially free of other cellular material, or culture medium when produced by recombinant techniques, or substantially free of chemical precursors or other chemicals when chemically synthesized. Optimally, an "isolated" polynucleotide molecule is free of sequences (optimally protein encoding sequences) that naturally flank the polynucleotide (i.e., sequences located at the 5' and 3' ends of the polynucleotide) in the genomic DNA of the organism from which the polynucleotide molecule is derived. For example, in various embodiments, the isolated polynucleotide molecule can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide molecule is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5% or 1% (by dry weight) of chemical precursors or non-protein-of-interest chemicals.

Fragments and variants of the disclosed polynucleotide molecules and proteins encoded thereby are also encompassed by the present invention. By "fragment" is intended a portion of the polynucleotide molecule or a portion of the amino acid sequence and hence protein encoded thereby. Fragments of a polynucleotide molecule may encode protein fragments that retain the biological activity of the wild-type and MUT1 Zm-D9 proteins as disclosed herein and hence gibberellin-response repressive activity. Alternatively, fragments of a polynucleotide molecule that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length polynucleotide molecule encoding the proteins of the invention.

Unless otherwise noted or obvious from the context, the term "Zm-D9" is intended to encompass polynucleotide molecules comprising the wild-type and MUT1 alleles of the Zm-D9 gene and fragments and variants thereof. Preferably, such fragments and variants of the wild-type and MUT1 alleles of the Zm-D9 gene encode Zm-D9 proteins that retain the biological activity of a full-length wild-type or MUT1 Zm-D9 protein as disclosed herein. The term "Zm-D9" may also be used herein to refer the proteins encoded by Zm-D9 polynucleotide molecules of the present invention.

A fragment of an Zm-D9 polynucleotide molecule that encodes a biologically active portion of a Zm-D9 protein of the invention will encode at least 15, 25, 30, 50, 100, 150, 200, 250, 300, 350, 400, 450, 500, 550 or 600 contiguous amino acids, or up to the total number of amino acids present in a full-length wild-type or MUT1 Zm-D9 protein of the invention (for example, 625 and 622 amino acids for SEQ ID NOS: 2 and 5, respectively). Fragments of a Zm-D9 polynucleotide molecule that are useful as hybridization probes or PCR primers generally need not encode a biologically active portion of a Zm-D9 protein.

Thus, a fragment of a Zm-D9 polynucleotide molecule may encode a biologically active portion of a wild-type or MUT1 Zm-D9 protein or it may be a fragment that can be used as a hybridization probe or PCR primer using methods disclosed below. A biologically active portion of a Zm-D9 protein can be prepared by isolating a portion of one of the Zm-D9 polynucleotide molecule of the invention, Zm-D9 protein (e.g., by recombinant expression in vitro), and assessing the activity of the Zm-D9 portion of the Zm-D9 protein. Polynucleotide molecules that are fragments of an Zm-D9 nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, 1,400 1,500, 1,600, 1,700, 1,800 or 1,850 contiguous nucleotides, or up to the number of nucleotides present in a full-length Zm-D9 polynucleotide disclosed herein (for example, 1878, 1875, 1869, and 1866 nucleotides for SEQ ID NOS: 1, 3, 4 and 6, respectively).

"Variants" is intended to mean substantially similar sequences. For polynucleotide molecules, a variant comprises a deletion and/or addition of one or more nucleotides at one or more internal sites within the native polynucleotide molecule and/or a substitution of one or more nucleotides at one or more sites in the native polynucleotide. As used herein, a "native" polynucleotide molecule or polypeptide comprises a naturally occurring nucleotide sequence or amino acid sequence, respectively. For polynucleotide molecules, conservative variants include those sequences that, because of the degeneracy of the genetic code, encode the amino acid sequence of one of the Zm-D9 polypeptides of the invention. Naturally occurring allelic variants such as these can be identified with the use of well-known molecular biology techniques, as, for example, with polymerase chain reaction (PCR) and hybridization techniques as outlined below. Variant polynucleotide molecules also include synthetically derived polynucleotide, such as those generated, for example, by using site-directed mutagenesis but which still encode a Zm-D9 protein of the invention. Generally, variants of a particular polynucleotide molecule of the invention will have at least about 80%, 85%, 90%, 91%, 92%, 93%, 94%, 95%, 96%, 97%, 98%, 99% or more sequence identity to that particular polynucleotide molecule as determined by sequence alignment programs and parameters described elsewhere herein.

Variants of a particular polynucleotide molecule of the invention (i.e., the reference polynucleotide) can also be evaluated by comparison of the percent sequence identity between the polypeptide encoded by a variant polynucleotide molecule and the polypeptide encoded by the reference polynucleotide. Thus, for example, an isolated polynucleotide molecule that encodes a polypeptide with a given percent sequence identity to the polypeptide of SEQ ID NO: 2 and/or 5 are disclosed. Percent sequence identity between any two polypeptides can be calculated using sequence alignment programs and parameters described elsewhere herein. Where any given pair of polynucleotide molecules of the invention is evaluated by comparison of the percent sequence identity shared by the two polypeptides they encode, the percent sequence identity between the two encoded polypeptides is at least about 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, wild-type or MUT1 Zm-D9 protein activity as described herein. Such variants may result from, for example, genetic polymorphism or from human manipulation. Biologically active variants of a native Zm-D9 protein of the invention will have at least about 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the Zm-D9 proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel, et al., (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotide molecules of the invention include both the naturally occurring sequences as well as mutant forms. Likewise, the proteins of the invention encompass naturally occurring proteins as well as variations and modified forms thereof. Such variants will continue to possess the desired wild-type or MUT1 Zm-D9 activity. Obviously, the mutations that will be made in the DNA encoding the variant must not place the sequence out of reading frame and optimally will not create complementary regions that could produce secondary mRNA structure. See, EP Patent Application Publication No. 75,444.

Figure 4:
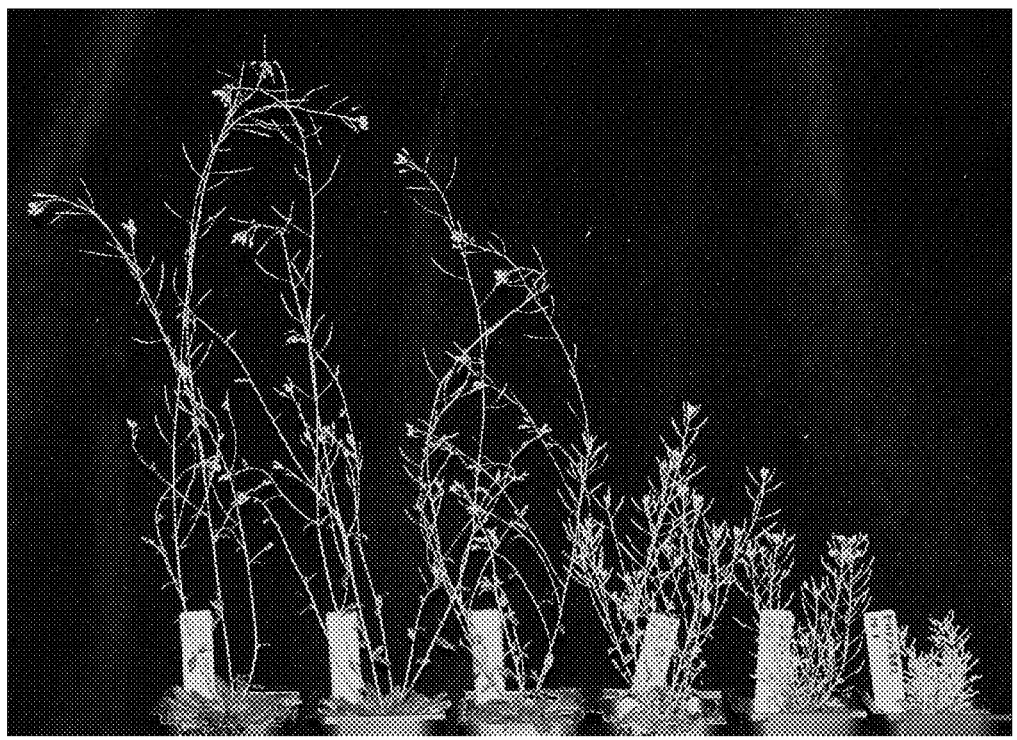
FIG. 4 depicts *Arabidopsis thaliana* ecotype Columbia T2 plants, 56 days after germination, comprising the maize DELLA cDNAs driven by the MS-S2a promoter. From left to right: MS-S2A PRO::GUS; MS-S2A PRO::ZM-D8; MS-S2A PRO::ZM-D9; MS-S2A PRO::MUT1 ZM-D9; MS-S2A PRO::ZM-D8 MPL; and MS-S2A PRO::ZM-D8 MUT.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by plant or root morphology changes in transgenic plants, such as, for example, monitoring changes in stem and/or root elongation in plants transformed with a Zm-D9 polynucleotide molecule of the present invention. See, for example, Example 1 below and FIG. 4.

Variant polynucleotide molecules and proteins also encompass sequences and proteins derived from a mutagenic and recombinogenic procedure such as DNA shuffling. With such a procedure, one or more different Zm-D9 coding sequences can be manipulated to create a new Zm-D9 possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the Zm-D9 gene of the invention and other known Zm-D9 genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

The polynucleotide molecules of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire Zm-D9 sequence set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99% or greater sequence identity. Functions of orthologs are often highly conserved among species. Thus, isolated polynucleotide molecules that encode for a Zm-D9 protein and which hybridize under stringent conditions to the Zm-D9 sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.). See also. Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide molecule is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the Zm-D9 polynucleotides of the invention. Methods for preparation of probes for hybridization and for construction of cDNA and genomic libraries are generally known in the art and are disclosed in Sambrook, et al., (1989) *Molecular Cloning: A Laboratory Manual* (2d ed., Cold Spring Harbor Laboratory Press, Plainview, N.Y.).

For example, an entire Zm-D9 polynucleotide molecule disclosed herein, or one or more portions thereof, may be used as a probe capable of specifically hybridizing to corresponding Zm-D9 polynucleotide molecule and messenger RNAs. To achieve specific hybridization under a variety of conditions, such probes include sequences that are unique among Zm-D9 polynucleotide sequences and are optimally at least about 10 nucleotides in length, and most optimally at least about 20 nucleotides in length. Such probes may be used to amplify a corresponding Zm-D9 polynucleotide molecule from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook, et al., (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel, et al., eds. (1995) *Current Protocols in Molecular Biology*, Chapter 2 (Greene Publishing and Wiley-Interscience, New York). See, Sambrook, et al., (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith, et al., (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65; and Pearson, et al., (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul, et al., (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul, et al., (1997) *Nucleic Acids Res.* 25:3389. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See, www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see, Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The Zm-D9 polynucleotide molecule of the invention can be provided in expression cassettes for expression in the plant Zm-D9 of interest. The cassette will include 5' and 3' regulatory sequences operably linked to a Zm-D9 polynucleotide molecule of the invention. "Operably linked" is intended to mean a functional linkage between two or more elements. For example, an operable linkage between a polynucleotide molecule of interest and a regulatory sequence (i.e., a promoter) is functional link that allows for expression of the polynucleotide molecule of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the Zm-D9 polynucleotide molecule to be under the transcriptional regulation of the regulatory regions. The expression cassette may additionally contain selectable marker genes.

The expression cassette will include in the 5'-3' direction of transcription, a transcriptional and translational initiation region (i.e., a promoter), a Zm-D9 polynucleotide molecule of the invention, and a transcriptional and translational termination region (i.e., termination region) functional in plants. The regulatory regions (i.e., promoters, transcriptional regulatory regions, and translational termination regions) and/or the Zm-D9 polynucleotide molecule of the invention may be native/analogous to the host cell or to each other. Alternatively, the regulatory regions and/or the Zm-D9 polynucleotide molecule of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide molecule is from a species different from the species from which the polynucleotide molecule was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

While it may be optimal to express the sequences using heterologous promoters, the native promoter sequences may be used. Such constructs can change expression levels of Zm-D9 in the plant or plant cell. Thus, the phenotype of the plant or plant cell can be altered.

The termination region may be native with the transcriptional initiation region, may be native with the operably linked Zm-D9 polynucleotide molecule of interest, may be native with the plant host, or may be derived from another source (i.e., foreign or heterologous) to the promoter, the Zm-D9 polynucleotide molecule of interest, the plant host, or any combination thereof. Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903; and Joshi, et al., (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray, et al., (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus) (Virology 154:9-20), and human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256); and maize chlorotic mottle virus leader (MCMV) (Lommel, et al., (1991) *Virology* 81:382-385). See also, Della-Cioppa, et al., (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention, including the native promoter of the polynucleotide sequence of interest. The promoters can be selected based on the desired outcome. The nucleic acids of the invention can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072, 050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237, and U.S. Pat. Nos. 5,814,618 and 5,789,156), herein incorporated by reference.

Tissue-preferred promoters can be utilized to target enhanced Zm-D9 expression within a particular plant tissue. Tissue-preferred promoters include Yamamoto, et al., (1997) *Plant J.* 12(2):255-265; Kawamata, et al., (1997) *Plant Cell Physiol.* 38(7):792-803; Hansen, et al., (1997) *Mol. Gen. Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam (1994) *Results Probl. Cell Differ.* 20:181-196; Orozco, et al., (1993) *Plant Mol. Biol.* 23(6): 1129-1138; Matsuoka, et al., (1993) *Proc Natl. Acad. Sci. USA* 90(20):9586-9590; and Guevara-Garcia, et al., (1993) *Plant J.* 4(3):495-505. Such promoters can be modified, if necessary, for weak expression.

Certain embodiments of the invention make use of plants transformed with tissue-preferred promoters, particularly stem-preferred promoters, operably linked to nucleotide sequences encoding Zm-D9 proteins. In one embodiment of the invention, the MS-S2A promoter (Abrahams, et al., (1995) *Plant Mol Biol* 27:513-28) is operably linked to a polynucleotide sequence encoding the wild-type or MUT1 Zm-D9 protein. The choice of promoter, and inherent tissue specificity, would likely influence the degree or intensity of morphological changes in transgenic plants which express the wild-type or MUT1 Zm-D9 protein of the invention. Stem-preferred in the case of the MS-S2A promoter implies expression associated with the vascular elements which has been documented (data not shown). The MS-S2A promoter appears to be optimal for expression of MUT1 Zm-D9 while actin, a constitutively expressed promoter with higher expression in leaf tissue has very modest or slight changes in morphology when used to express the MUT1 ZM-D9 protein.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138; and Matsuoka, et al., (1993) *Proc. Natl. Acad. Sci. USA* 90(20):9586-9590. (See above.)

Root-preferred promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*); and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2):343-350). The TR1' gene, fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772); and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732; and 5,023,179.

Where low level expression is desired, weak promoters will be used. Generally, by "weak promoter" is intended a promoter that drives expression of a coding sequence at a low level. By low level is intended at levels of about $1/1000$ transcripts to about $1/100,000$ transcripts to about $1/500,000$ transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core $^{35}$S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su, et al., (2004) *Biotechnol Bioeng* 85:610-9 and Fetter, et al., (2004) *Plant Cell* 16:215-28), cyan florescent protein (CYP) (Bolte, et al., (2004) *J. Cell Science* 117:943-54 and Kato, et al., (2002) *Plant Physiol.* 129:913-42), and yellow florescent protein (PhiYFP™ from Evrogen, see, Bolte, et al., (2004) *J. Cell Science* 117:943-54). For additional selectable markers, see generally, Yarranton (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Aci. USA* 86:5400-5404; Fuerst, et al., (1989) *Proc. Natl. Acad. Sci. USA* 86:2549-2553; Deuschle, et al., (1990) *Science* 248:480-483; Gossen (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman (1989) *Topics Mol. Struc. Biol.* 10:143-162; Degenkolb, et al., (1991) *Antimicrob. Agents Chemother.* 35:1591-1595; Kleinschnidt, et al. (1988) *Biochemistry* 27:1094-1104; Bonin (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin); Gill, et al., (1988) *Nature* 334:721-724. Such disclosures are herein incorporated by reference.

The above list of selectable marker genes is not meant to be limiting. Any selectable marker gene can be used in the present invention.

In one embodiment, the polynucleotide molecule of interest is targeted to the chloroplast for expression. In this manner, where the polynucleotide of interest is not directly inserted into the chloroplast, the expression cassette will additionally contain a nucleic acid encoding a transit peptide to direct the gene product of interest to the chloroplasts. Such transit peptides are known in the art. See, for example, Von Heijne, et al., (1991) *Plant Mol. Biol. Rep.* 9:104-126; Clark, et al., (1989) *J. Biol. Chem.* 264:17544-17550; Della-Cioppa, et al., (1987) *Plant Physiol.* 84:965-968; Romer, et al., (1993) *Biochem. Biophys. Res. Commun.* 196:1414-1421; and Shah, et al., (1986) *Science* 233:478-481.

Chloroplast targeting sequences are known in the art and include the chloroplast small subunit of ribulose-1,5-bisphosphate carboxylase (Rubisco) (de Castro Silva Filho, et al., (1996) *Plant Mol. Biol.* 30:769-780; Schnell, et al., (1991) *J. Biol. Chem.* 266(5):3335-3342); 5-(enolpyruvyl)shikimate-3-phosphate synthase (EPSPS) (Archer, et al., (1990) *J. Bioenerg. Biomemb.* 22(6):789-810); tryptophan synthase (Zhao, et al., (1995) *J. Biol. Chem.* 270(11):6081-6087); plastocyanin (Lawrence, et al., (1997) *J. Biol. Chem.* 272(33): 20357-20363); chorismate synthase (Schmidt, et al., (1993) *J. Biol. Chem.* 268(36):27447-27457); and the light harvesting chlorophyll a/b binding protein (LHBP) (Lamppa, et al., (1988) *J. Biol. Chem.* 263:14996-14999). See also, Von Heijne, et al., (1991) *Plant Mol. Biol. Rep.* 9:104-126; Clark, et al., (1989) *J. Biol. Chem.* 264:17544-17550; Della-Cioppa, et al., (1987) *Plant Physiol.* 84:965-968; Romer, et al., (1993) *Biochem. Biophys. Res. Commun.* 196:1414-1421; and Shah, et al., (1986) *Science* 233:478-481.

Methods for transformation of chloroplasts are known in the art. See, for example, Svab, et al., (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) *Proc. Natl. Acad. Sci. USA* 91:7301-7305.

The polynucleotides of interest to be targeted to the chloroplast may be optimized for expression in the chloroplast to account for differences in codon usage between the plant nucleus and this organelle. In this manner, the polynucleotide molecule of interest may be synthesized using chloroplast-preferred codons. See, for example, U.S. Pat. No. 5,380,831, herein incorporated by reference.

The methods of the invention involve introducing a polypeptide or polynucleotide molecule into a plant. "Introducing" is intended to mean presenting to the plant the polynucleotide molecule or polypeptide in such a manner that the sequence gains access to the interior of a cell of the plant. The methods of the invention do not depend on a particular method for introducing a sequence into a plant, only that the polynucleotide molecule or polypeptides gains access to the interior of at least one cell of the plant. Methods for introducing polynucleotide molecule or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide molecule is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway, et al., (1986) *Biotechniques* 4:320-334), electroporation (Riggs, et al., (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski, et al., (1984) *EMBO J.* 3:2717-2722), and ballistic particle acceleration (see, for example, U.S. Pat. Nos. 4,945,050; 5,879,918; 5,886,244; and 5,932,782; Tomes, et al., (1995) in *Plant Cell, Tissue, and Organ Culture: Fundamental Methods*, ed. Gamborg and Phillips (Springer-Verlag, Berlin); McCabe, et al., (1988) *Biotechnology* 6:923-926); and Lec1 transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783; and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature (London)* 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

In specific embodiments, the Zm-D9 sequences of the invention can be provided to a plant using a variety of transient transformation methods. Such transient transformation methods include, but are not limited to, the introduction of the Zm-D9 protein or variants and fragments thereof directly into the plant or the introduction of the Zm-D9 transcript into the plant. Such methods include, for example, microinjection or particle bombardment. See, for example, Crossway, et al., (1986) *Mol. Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107:775-784, all of which are herein incorporated by reference. Alternatively, the Zm-D9 polynucleotide molecule can be transiently transformed into the plant using techniques known in the art. Such techniques include viral vector system and the precipitation of the polynucleotide molecule in a manner that precludes subsequent release of the DNA. Thus, the transcription from the particle-bound DNA can occur, but the frequency with which it is released to become integrated into the genome is greatly reduced. Such methods include the use particles coated with polyethylimine (PEI; Sigma #P3143).

In other embodiments, the polynucleotide molecule of the invention may be introduced into plants by contacting plants with a virus or viral nucleic acids. Generally, such methods involve incorporating a nucleotide construct of the invention within a viral DNA or RNA molecule. It is recognized that the Zm-D9 amino acid sequence of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta, et al., (1996) *Molecular Biotechnology* 5:209-221; herein incorporated by reference.

Methods are known in the art for the targeted insertion of a polynucleotide molecule at a specific location in the plant genome. In one embodiment, the insertion of the polynucleotide molecule at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide molecule of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide molecule of interest is thereby integrated at a specific chromosomal position in the plant genome.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide molecule of the invention, for example, an expression cassette of the invention, stably incorporated into their genome.

Pedigree breeding starts with the crossing of two genotypes, such as an elite line of interest and one other elite inbred line having one or more desirable characteristics (i.e., having stably incorporated a polynucleotide molecule of the invention, having a modulated activity and/or level of the polypeptide of the invention, etc) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→$F_5$, etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line of interest, comprising the steps of crossing a plant of maize inbred line of interest with a donor plant comprising a mutant gene or transgene conferring a desired trait (i.e., reduced plant height or stature), selecting an F1 progeny plant comprising the mutant gene or transgene conferring the desired trait, and backcrossing the selected F1 progeny plant to the plant of maize inbred line of interest. This method may further comprise the step of obtaining a molecular marker profile of maize inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development" Fehr, 1993 Macmillan Publishing Company the disclosure of which is incorporated herein by reference. In addition, mutations created in other lines may be used to produce a backcross conversion of elite lines that comprises such mutations.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos* nucifera), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

A method for modulating the concentration and/or activity of the polypeptide of the present invention in a plant is provided. In general, concentration and/or activity is increased or decreased by at least 1%, 5%, 10%, 20%, 30%, 40%, 50%, 60%, 70%, 80% or 90% relative to a native control plant, plant part, or cell which did not have the sequence of the invention introduced. Modulation in the present invention may occur during and/or subsequent to growth of the plant to the desired stage of development. In specific embodiments, the polypeptides of the present invention are modulated in monocots, particularly maize.

The expression level of the Zm-D9 polypeptide may be measured directly, for example, by assaying for the level of the Zm-D9 polypeptide in the plant, or indirectly, for example, by measuring the Zm-D9 activity of the Zm-D9 polypeptide in the plant by, for example, determining overall plant height or the height of the stem or stalk. Methods for determining the Zm-D9 activity are described elsewhere herein.

In specific embodiments, the polypeptide or the polynucleotide molecule of the invention is introduced into the plant cell. Subsequently, a plant cell having the introduced sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of polypeptides of the present invention in the plant. Plant forming conditions are well known in the art and discussed briefly elsewhere herein.

It is also recognized that the level and/or activity of the polypeptide may be modulated by employing a polynucleotide molecule that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham, et al., (1999) *Proc. Natl. Acad. Sci. USA* 96:8774-8778; herein incorporated by reference.

It is therefore recognized that methods of the present invention do not depend on the incorporation of the entire polynucleotide into the genome, only that the plant or cell thereof is altered as a result of the introduction of the polynucleotide molecule into a cell. In one embodiment of the invention, the genome may be altered following the introduction of the polynucleotide molecule into a cell. For example, the polynucleotide, or any part thereof, may incorporate into the genome of the plant. Alterations to the genome of the present invention include, but are not limited to, additions, deletions, and substitutions of nucleotides into the genome. While the methods of the present invention do not depend on additions, deletions, and substitutions of any particular number of nucleotides, it is recognized that such additions, deletions, or substitutions comprises at least one nucleotide.

In one embodiment, the activity and/or level of the Zm-D9 polypeptide of the invention is increased. An increase in the level and/or activity of the Zm-D9 polypeptide of the invention can be achieved by providing to the plant a Zm-D9 polypeptide. As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide having Zm-D9. It is also recognized that the methods of the invention may employ a polynucleotide molecule that is not capable of directing, in the transformed plant, the expression of a protein or an RNA. Thus, the level and/or activity of a Zm-D9 polypeptide may be increased by altering the gene encoding the Zm-D9 polypeptide or its promoter. See, e.g., Kmiec, U.S. Pat. No. 5,565,350; Zarling, et al., PCT/US93/03868. Therefore mutagenized plants that carry mutations in Zm-D9 genes, where the mutations increase expression of the Zm-D9 gene or increase the Zm-D9 activity of the encoded Zm-D9 polypeptide are provided.

In other embodiments, the activity and/or level of the Zm-D9 polypeptide of the invention is reduced or eliminated by introducing into a plant a polynucleotide that inhibits the level or activity of the Zm-D9 polypeptide of the invention. The polynucleotide may inhibit the expression of Zm-D9 directly, by preventing translation of the Zm-D9 messenger RNA, or indirectly, by encoding a polypeptide that inhibits the transcription or translation of a Zm-D9 gene encoding a Zm-D9 protein. Methods for inhibiting or eliminating the expression of a gene in a plant are well known in the art, and any such method may be used in the present invention to inhibit the expression of Zm-D9 in a plant. In other embodiments of the invention, the activity of Zm-D9 polypeptide is reduced or eliminated by transforming a plant cell with a sequence encoding a polypeptide that inhibits the activity of the Zm-D9 polypeptide. In other embodiments, the activity of a Zm-D9 polypeptide may be reduced or eliminated by disrupting the gene encoding the Zm-D9 polypeptide. The invention encompasses mutagenized plants that carry mutations in Zm-D9 genes, where the mutations reduce expression of the Zm-D9 gene or inhibit the Zm-D9 activity of the encoded Zm-D9 polypeptide.

Reduction of the activity of specific genes (also known as gene silencing or gene suppression) is desirable for several aspects of genetic engineering in plants. Many techniques for gene silencing are well known to one of skill in the art, including, but not limited to, antisense technology (see, e.g., Sheehy, et al., (1988) *Proc. Natl. Acad. Sci. USA* 85:8805-8809; and U.S. Pat. Nos. 5,107,065; 5,453,566; and 5,759, 829); cosuppression (e.g., Taylor (1997) *Plant Cell* 9:1245; Jorgensen (1990) *Trends Biotech.* 8(12):340-344; Flavell (1994) *Proc. Natl. Acad. Sci. USA* 91:3490-3496; Finnegan, et al., (1994) *Bio/Technology* 12:883-888; and Neuhuber, et al., (1994) *Mol. Gen. Genet.* 244:230-241); RNA interference (Napoli, et al., (1990) *Plant Cell* 2:279-289; U.S. Pat. No. 5,034,323; Sharp (1999) *Genes Dev.* 13:139-141; Zamore, et al., (2000) *Cell* 101:25-33; and Montgomery, et al., (1998) *Proc. Natl. Acad. Sci. USA* 95:15502-15507), virus-induced gene silencing (Burton, et al., (2000) *Plant Cell* 12:691-705; and Baulcombe (1999) *Curr. Op. Plant Bio.* 2:109-113); target-RNA-specific ribozymes (Haseloff, et al., (1988) *Nature* 334:585-591); hairpin structures (Smith, et al., (2000) *Nature* 407:319-320; WO 99/53050; WO 02/00904; WO 98/53083; Chuang and Meyerowitz (2000) *Proc. Natl. Acad. Sci. USA* 97:4985-4990; Stoutjesdijk, et al., (2002) *Plant Physiol.* 129: 1723-1731; Waterhouse and Helliwell (2003) *Nat. Rev. Genet.* 4:29-38; Pandolfini, et al., *BMC Biotechnology* 3:7, U.S. Patent Publication Number 20030175965; Panstruga, et al., (2003) *Mol. Biol. Rep.* 30:135-140; Wesley, et al., (2001) *Plant J.* 27:581-590; Wang and Waterhouse (2001) *Curr. Opin. Plant Biol.* 5:146-150; U.S. Patent Publication Number 20030180945; and, WO 02/00904, all of which are herein incorporated by reference); ribozymes (Steinecke, et al., (1992) *EMBO J.* 11:1525; and Perriman, et al., (1993) *Antisense Res. Dev.* 3:253); oligonucleotide-mediated targeted modification (e.g., WO 03/076574 and WO 99/25853); Zn-finger targeted molecules (e.g., WO 01/52620; WO 03/048345; and WO 00/42219); transposon tagging (Maes, et al., (1999) *Trends Plant Sci.* 4:90-96; Dharmapuri and Sonti (1999) *FEMS Microbiol. Lett.* 179:53-59; Meissner, et al., (2000) *Plant J.* 22:265-274; Phogat, et al., (2000) *J. Biosci.* 25:57-63; Walbot (2000) *Curr. Opin. Plant Biol.* 2:103-107; Gai, et al., (2000) *Nucleic Acids Res.* 28:94-96; Fitzmaurice, et al., (1999) *Genetics* 153:1919-1928; Bensen, et al., (1995) *Plant Cell* 7:75-84; Mena, et al., (1996) *Science* 274:1537-1540; and U.S. Pat. No. 5,962,764); each of which is herein incorporated by reference; and other methods or combinations of the above methods known to those of skill in the art.

It is recognized that with the polynucleotides of the invention, antisense constructions, complementary to at least a portion of the messenger RNA (mRNA) for the Zm-D9 sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used.

The polynucleotides of the present invention may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a polynucleotide that corresponds to the transcript of the endogenous gene. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference. Thus, many methods may be used to reduce or eliminate the activity of a Zm-D9 polypeptide. More than one method may be used to reduce the activity of a single Zm-D9 polypeptide. In addition, combinations of methods may be employed to reduce or eliminate the activity of the Zm-D9 polypeptides.

In some embodiments, the activity of the Zm-D9 is reduced or eliminated by transforming a Zm-D9 plant cell with an expression cassette that expresses a polynucleotide that inhibits the expression of the Zm-D9. The polynucleotide may inhibit the expression of one or more Zm-D9 proteins directly, by preventing translation of the Zm-D9 messenger RNA, or indirectly, by encoding a polypeptide that inhibits the transcription or translation of a maize gene encoding a Zm-D9 protein. Methods for inhibiting or eliminating the expression of a gene in a plant are well known in the art, and any such method may be used in the present invention to inhibit the expression of one or more Zm-D9 proteins.

In accordance with the present invention, the expression of a Zm-D9 is inhibited if the protein level of the Zm-D9 is statistically lower than the protein level of the same Zm-D9 in a plant that has not been genetically modified or mutagenized to inhibit the expression of that Zm-D9 protein. In particular embodiments of the invention, the protein level of the Zm-D9 protein in a modified plant according to the invention is less than 95%, less than 90%, less than 80%, less than 70%, less than 60%, less than 50%, less than 40%, less than 30%, less than 20%, less than 10% or less than 5% of the protein level of the same Zm-D9 protein in a plant that is not a mutant or that has not been genetically modified to inhibit the expression of that Zm-D9 protein. The expression level of the Zm-D9 protein may be measured directly, for example, by assaying for the level of Zm-D9 protein expressed in the maize plant cell or plant, or indirectly, for example, by measuring the Zm-D9 activity of the Zm-D9 protein in the maize plant cell or plant. Methods for determining the Zm-D9 activity of Zm-D9 proteins are described elsewhere herein.

In other embodiments of the invention, the activity of one or more Zm-D9 proteins is reduced or eliminated by transforming a maize plant cell with an expression cassette comprising a polynucleotide encoding a polypeptide that inhibits the activity of one or more Zm-D9 proteins. The Zm-D9 activity of a Zm-D9 protein is inhibited according to the present invention if the Zm-D9 activity of the Zm-D9 protein is statistically lower the Zm-D9 activity of the same Zm-D9 protein in a plant that has not been genetically modified to inhibit the Zm-D9 activity of that Zm-D9 protein. In particular embodiments of the invention, the Zm-D9 activity of the Zm-D9 protein in a modified plant according to the invention is less than 95%, less than 90%, less than 80%, less than 70%, less than 60%, less than 50%, less than 40%, less than 30%, less than 20%, less than 10%, or less than 5% of the Zm-D9 activity of the same Zm-D9 protein in a plant that has not been genetically modified to inhibit the expression of that Zm-D9 protein. The Zm-D9 activity of a Zm-D9 protein is "eliminated" according to the invention when it is not detectable by the assay methods described elsewhere herein. Methods of determining the Zm-D9 activity of a Zm-D9 protein are described elsewhere herein.

In other embodiments, the activity of a Zm-D9 protein may be reduced or eliminated by disrupting the gene encoding the Zm-D9 protein. The invention encompasses mutagenized maize plants that carry mutations in Zm-D9 genes, where the mutations reduce expression of the Zm-D9 gene or inhibit the Zm-D9 activity of the encoded Zm-D9 protein.

Thus, many methods may be used to reduce or eliminate the activity of a Zm-D9 protein. More than one method may be used to reduce the activity of a single Zm-D9 protein. In addition, combinations of methods may be employed to reduce or eliminate the activity of two or more different Zm-D9 proteins.

Non-limiting examples of methods of reducing or eliminating the expression of a Zm-D9 protein are given below.

A. Polynucleotide-Based Methods:

In some embodiments of the present invention, a maize plant cell is transformed with an expression cassette that is capable of expressing a polynucleotide that inhibits the expression of Zm-D9 protein. The term "expression" as used herein refers to the biosynthesis of a gene product, including the transcription and/or translation of said gene product. For example, for the purposes of the present invention, an expression cassette capable of expressing a polynucleotide that inhibits the expression of at least one Zm-D9 protein in a maize plant is an expression cassette capable of producing an RNA molecule that inhibits the transcription and/or translation of at least one Zm-D9 protein in a maize plant. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a Zm-D9 protein in a maize plant are given below.

1. Sense Suppression/Cosuppression

In some embodiments of the invention, inhibition of the expression of Zm-D9 protein may be obtained by sense suppression or cosuppression. For cosuppression, an expression cassette is designed to express an RNA molecule corresponding to all or part of a messenger RNA encoding a Zm-D9 protein in the "sense" orientation. Overexpression of the RNA molecule can result in reduced expression of the native gene. Accordingly, multiple plant lines transformed with the cosuppression expression cassette are screened to identify those that show the greatest inhibition of Zm-D9 protein expression.

The polynucleotide used for cosuppression may correspond to all or part of the sequence encoding the Zm-D9 protein, all or part of the 5' and/or 3' untranslated region of a Zm-D9 protein transcript, or all or part of both the coding sequence and the untranslated regions of a transcript encoding a Zm-D9 protein. In some embodiments where the polynucleotide comprises all or part of the coding region for the Zm-D9 protein, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763; and U.S. Pat. Nos. 5,034,323, 5,283,184 and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication Number 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference.

2. Antisense Suppression

In some embodiments of the invention, inhibition of the expression of the Zm-D9 protein may be obtained by antisense suppression. For antisense suppression, the expression cassette is designed to express an RNA molecule complementary to all or part of a messenger RNA encoding the Zm-D9 protein. Overexpression of the antisense RNA molecule can result in reduced expression of the native gene. Accordingly, multiple plant lines transformed with the antisense suppression expression cassette are screened to identify those that show the greatest inhibition of Zm-D9 protein expression.

The polynucleotide for use in antisense suppression may correspond to all or part of the complement of the sequence encoding the Zm-D9 protein, all or part of the complement of the 5' and/or 3' untranslated region of the Zm-D9 protein transcript, or all or part of the complement of both the coding sequence and the untranslated regions of a transcript encoding the Zm-D9 protein. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication Number 20020048814, herein incorporated by reference.

3. Double-Stranded RNA Interference

In some embodiments of the invention, inhibition of the expression of a Zm-D9 protein may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of Zm-D9 protein expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631, and WO 00/49035; each of which is herein incorporated by reference.

4. Hairpin RNA Interference and Intron-Containing Hairpin RNA Interference

In some embodiments of the invention, inhibition of the expression of Zm-D9 protein may be obtained by hairpin RNA (hpRNA) interference or intron-containing hairpin RNA (ihpRNA) interference. These methods are highly efficient at inhibiting the expression of endogenous genes. See, Waterhouse and Helliwell (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97:4985-4990; Stoutjesdijk, et al., (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk, et al., (2002) *Plant Physiol.* 129:1723-1731; Waterhouse and Helliwell (2003) *Nat. Rev. Genet.* 4:29-38; Pandolfini, et al., *BMC Biotechnology* 3:7, and U.S. Patent Publication Number 20030175965; each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and U.S. Patent Publication Number 20030180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing (Aufsatz, et al., (2002) *PNAS* 99(4): 16499-16506; Mette, et al., (2000) *EMBO J.* 19(19):5194-5201).

5. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for Zm-D9 protein). Methods of using amplicons to inhibit the expression of endogenous plant genes are described, for example, in Angell and Baulcombe (1997) *EMBO J.* 16:3675-3684, Angell and Baulcombe (1999) *Plant J.* 20:357-362, and U.S. Pat. No. 6,646,805, each of which is herein incorporated by reference.

6. Ribozymes

In some embodiments, the polynucleotide expressed by the expression cassette of the invention is catalytic RNA or has ribozyme activity specific for the messenger RNA of Zm-D9 protein. Thus, the polynucleotide causes the degradation of the endogenous messenger RNA, resulting in reduced expression of the Zm-D9 protein. This method is described, for example, in U.S. Pat. No. 4,987,071, herein incorporated by reference.

7. Small Interfering RNA or Micro RNA

In some embodiments of the invention, inhibition of the expression of Zm-D9 protein may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of Zm-D9 protein expression, the 22-nucleotide sequence is selected from a Zm-D9 protein transcript sequence and contains 22 nucleotides of said Zm-D9 protein sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

B. Polypeptide-Based Inhibition of Gene Expression:

In one embodiment, the polynucleotide encodes a zinc finger protein that binds to a gene encoding a Zm-D9 protein in a maize plant or cell, resulting in reduced expression of the gene. In particular embodiments, the zinc finger protein binds to a regulatory region of a Zm-D9 protein gene. In other embodiments, the zinc finger protein binds to a messenger RNA encoding a Zm-D9 protein and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication Number 20030037355; each of which is herein incorporated by reference.

C. Polypeptide-Based Inhibition of Protein Activity:

In some embodiments of the invention, the polynucleotide encodes an antibody that binds to at least one Zm-D9 protein, and reduces the Zm-D9 activity of the Zm-D9 protein. In another embodiment, the binding of the antibody results in increased turnover of the antibody-Zm-D9 protein complex by cellular quality control mechanisms. The expression of antibodies in plant cells and the inhibition of molecular pathways by expression and binding of antibodies to proteins in plant cells are well known in the art. See, for example, Conrad and Sonnewald (2003) *Nature Biotech.* 21:35-36, incorporated herein by reference.

D. Gene Disruption:

In some embodiments of the present invention, the activity of a Zm-D9 protein is reduced or eliminated by disrupting the gene encoding the Zm-D9 protein. The gene encoding the Zm-D9 protein may be disrupted by any method known in the art. For example, in one embodiment, the gene is disrupted by transposon tagging. In another embodiment, the gene is disrupted by mutagenizing maize plants using random or targeted mutagenesis, and selecting for plants that have reduced or altered Zm-D9 protein activity.

1. Transposon Tagging

In one embodiment of the invention, transposon tagging is used to reduce or eliminate the Zm-D9 activity of the Zm-D9 protein. Transposon tagging comprises inserting a transposon within an endogenous Zm-D9 gene to reduce or eliminate expression of the Zm-D9 protein. "Zm-D9 gene" is intended to mean the gene that encodes a Zm-D9 protein according to the invention.

In this embodiment, the expression of the Zm-D9 protein is reduced or eliminated by inserting a transposon within a regulatory region or coding region of the gene encoding the Zm-D9 protein. A transposon that is within an exon, intron, 5' or 3' untranslated sequence, a promoter, or any other regulatory sequence of a Zm-D9 gene may be used to reduce or eliminate the expression and/or activity of the encoded Zm-D9 protein.

Methods for the transposon tagging of specific genes in plants are well known in the art. See, for example, Maes, et al., (1999) *Trends Plant Sci.* 4:90-96; Dharmapuri and Sonti (1999) *FEMS Microbiol. Lett.* 179:53-59; Meissner, et al., (2000) *Plant J.* 22:265-274; Phogat, et al., (2000) *J. Biosci.* 25:57-63; Walbot (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540; and U.S. Pat. No. 5,962,764; each of which is herein incorporated by reference.

2. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima, et al., (1998) *Virology* 243: 472-481; Okubara, et al., (1994) *Genetics* 137:867-874; and Quesada, et al., (2000) *Genetics* 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (Zm-D9 activity) of the encoded protein are well known in the art. Insertional mutations in gene exons usually result in null-mutants. Mutations in conserved residues are particularly effective in inhibiting the Zm-D9 activity of the encoded protein. Conserved residues of plant DELLA proteins are suitable for mutagenesis with the goal to eliminate or repress gibberellin signaling activity have been described. See, for example, Itoh, H., M. Ueguchi-Tanaka, et al., (2002) *Plant Cell* 14:57-70. Such mutants can be isolated according to well-known procedures, and mutations in different Zm-D9 loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of a Zm-D9 protein. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,984; each of which are herein incorporated by reference. See also, WO 98/49350, WO 99/07865, WO 99/25821, and Beetham, et al., (1999) *Proc. Natl. Acad. Sci. USA* 96:8774-8778; each of which is herein incorporated by reference.

In certain embodiments, the polynucleotide molecules of the present invention can be stacked with any combination of polynucleotide sequences of interest in order to create plants with a desired trait. A trait, as used herein, refers to the phenotype derived from a particular sequence or groups of sequences. For example, the polynucleotide molecules of the present invention may be stacked with any other polynucleotide molecules encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser, et al., (1986) *Gene* 48:109), lectins (Van Damme, et al., (1994) *Plant Mol. Biol.* 24:825, pentin (described in U.S. Pat. No. 5,981,722), and the like. The combinations generated can also include multiple copies of any one of the polynucleotide molecules of interest. The polynucleotide molecules of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson, et al., (1987) *Eur. J. Biochem.* 165:99-106; and WO 98/20122) and high methionine proteins (Pedersen, et al., (1986) *J. Biol. Chem.* 261:6279; Kirihara, et al., (1988) *Gene* 71:359; and Musumura, et al., (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotide molecules of the present invention can also be stacked with traits desirable for disease or herbicide resistance (e.g., fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)); the disclosures of which are herein incorporated by reference. One could also combine the polynucleotide molecules of the present invention with polynucleotide molecules providing agronomic traits such as male sterility (e.g., see, U.S. Pat. No. 5,583,210), stalk strength (see, U.S. Pat. No. 6,803,498) flowering time (see, U.S. Pat. No. 6,573,430), or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotide molecules of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802 and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen, et al., (1986) *J. Biol. Chem.* 261:6279; Kirihara, et al., (1988) *Gene* 71:359; both of which are herein incorporated by reference); and rice (Musumura, et al., (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser, et al., (1986) *Gene* 48:109); and the like.

Genes encoding disease resistance traits include detoxification genes, such as against fumonosin (U.S. Pat. No. 5,792, 931); avirulence (avr) and disease resistance (R) genes (Jones, et al., (1994) *Science* 266:789; Martin, et al., (1993) *Science* 262:1432; and Mindrinos, et al., (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene); glyphosate (e.g., the EPSPS gene and the GAT gene; see, for example, U.S. Publication Number 20040082770 and WO 03/092360); or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802 and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see, Schubert, et al., (1988) *J. Bacteriol* 170:5837-5847) facilitate expression of polyhydroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

The following examples are offered by way of illustration and not by way of limitation.

EXAMPLE 1

Isolation of the Maize D9 Gene

Maize encodes two DELLA proteins (dwarf plant8, D8 and dwarf plant9, D9) of which several dominant mutants have been isolated (Winkler and Freeling (1994) *Planta* 193:341-348). Although, Zm-D9 has been described genetically (Winkler and Freeling (1994) *Planta* 193:341-348), the gene has not been previously characterized at the molecular level. Two Zm-D9 alleles have been isolated and analyzed in the course of this work. The wild type Zm-D9 allele was isolated by RT PCR from RNA from maize line B73. The Zm-D9 MUT1 allele was isolated by PCR from genomic DNA isolated from seedlings of a GA-unresponsive line designated D9xB73 (FIG. 1). Zm-D9 MUT1 was predicted to lack introns, as do other reported DELLA genes. To ensure that the correct coding sequence was obtained for Zm-D9 MUT1, the cDNA was verified by RT-PCR.

Figure 2:
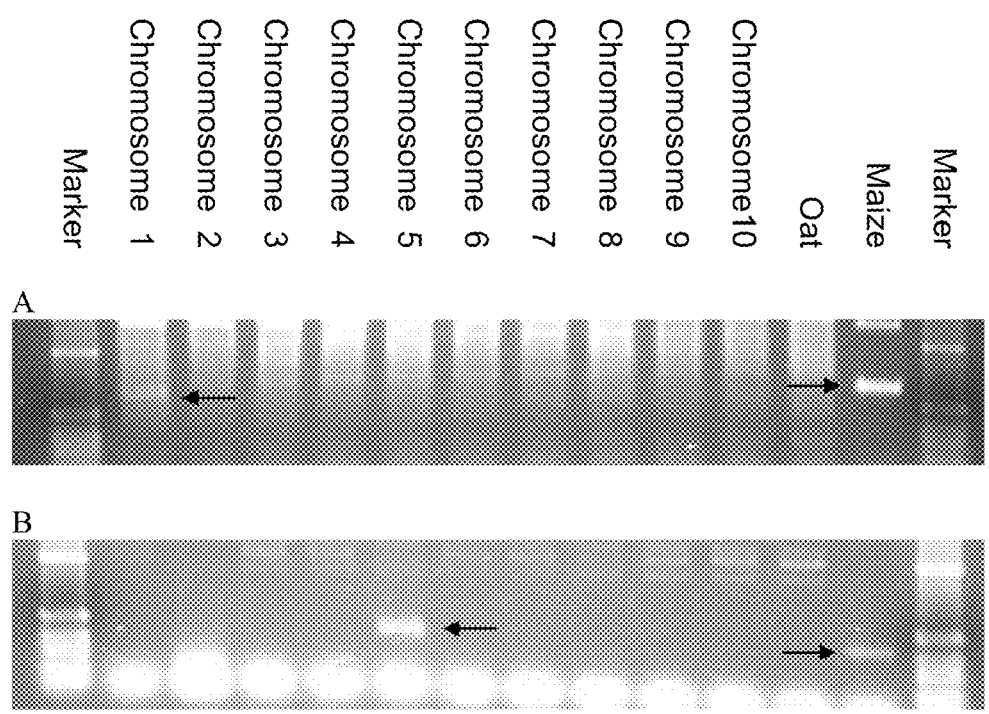
FIG. 2 depicts the chromosomal location of the maize Dwarf 8 and Dwarf 9 genes. Analytical PCR from oat addition lines (FIG. 2B) demonstrated that the putative Zm-D9 gene is indeed located on maize Chromosome 5 as expected from genetic mapping. This gene was found to be in a distinct location from the positive control Zm-D8 PCR product (FIG. 2A), which is known to be on Chromosome 1.

Zm-D8 is located in BIN 1.09, while Zm-D9 is located in a syntenous region on chromosome 5, BIN 5.00 (Helentjaris, et al., (1988) *Genetics* 118:353-363; Winkler and Freeling (1994) *Planta* 193:341-348; Lawrence, et al., (2005) *Plant Physiol.* 138:55-58). To verify that the alleles isolated are forms of Zm-D9, multiple projects were initiated including BAC library screening and phenotype recapitulation through transgenics. Zm-D9 was mapped to B73 BAC bacb.pk425.i4 which could not be tied to the genetic or physical maps, although it did link to markers found on both chromosomes 1 and 5. To show that the putative Zm-D9 was distinct from Zm-D8 and to determine its chromosomal location, PCR analysis of oat addition lines was performed (FIG. 2; Ananiev, et al., (1997) *Proc. Natl. Sci. USA* 94:3524-3529) and confirmed by sequencing of the reaction products. This analysis confirmed the location of the putative Zm-D9 as chromosome 5, distinct from the Zm-D8 locus on chromosome 1.

Figure 3:
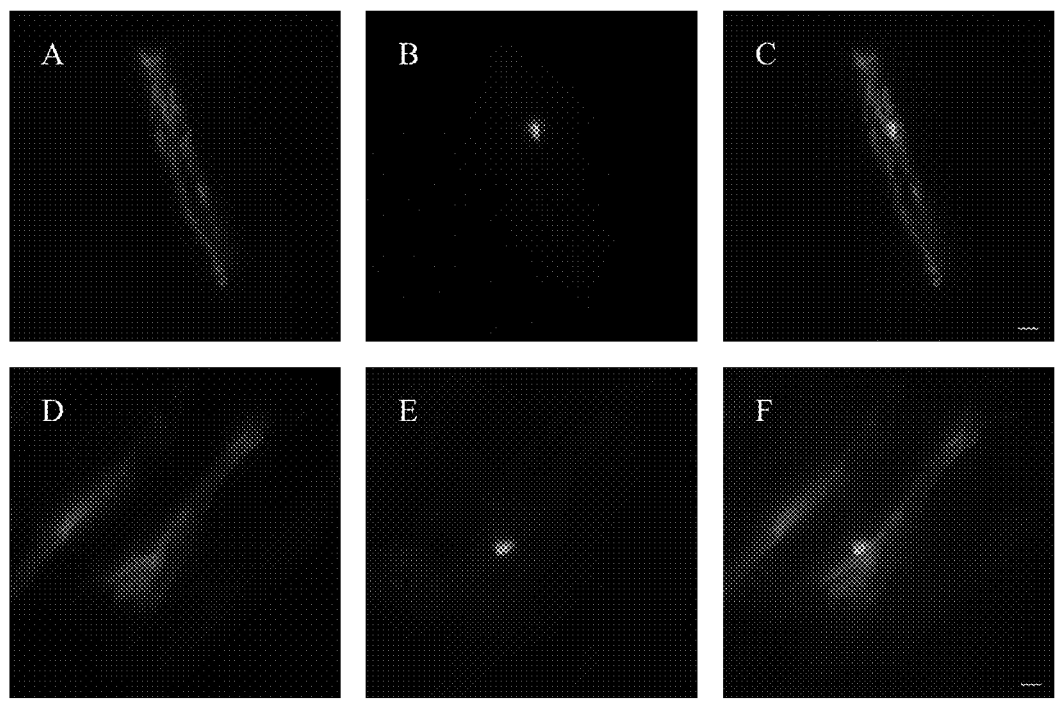
FIGS. 3A-3F depict the subcellular localization of maize DELLA proteins fused to AC-GFP1 (*Aequorea coerulescens* GFP).

The subcellular localization of two maize DELLA proteins was determined by fluorescent protein fusions (FIG. 3). The putative Zm-D9 localization was similar to that of Zm-D8 and is consistent with localization in the nucleus. Nuclear localization has been documented for numerous DELLA proteins in other plant systems (Silverstone, et al., (2001) *Plant Cell* 10:155-169; Ogawa, et al., (2000) *Gene* 245:21-29; Fleck and Harberd (2002) *Plant J.* 32:935-947; Gubler, et al., (2002) *Plant Physiol.* 129:191-200; Wen and Chang (2002) *Plant Cell* 14:87-100). Tungsten particles coated with the following Multisite Gateway (Invitrogen, USA) adapted Japan Tobacco intermediate constructs (Hiei, et al., 1994; Ishida, et al., 1996): PHP23800, attB4:UBI PRO:attB1:ZM-D8:attB2:AC-GFP1:NOS TERM:attB3 or PHP25355, attB4:UBI PRO:attB1:ZM-D9:attB2:AcGFP1:NOS TERM:attB3 were employed. Three days after germination (DAG) in the dark at RT, HG11 etiolated seedlings were particle bombarded with the above constructs with using a Biolistic PDS-1000/He Particle Delivering System (BioRad, USA) and 650 psi rupture disks. At 6 DAG, the bombarded, etiolated seedlings were visualized with a CARV spinning disk confocal microscope (Fryer Company, USA).

Figure 5:
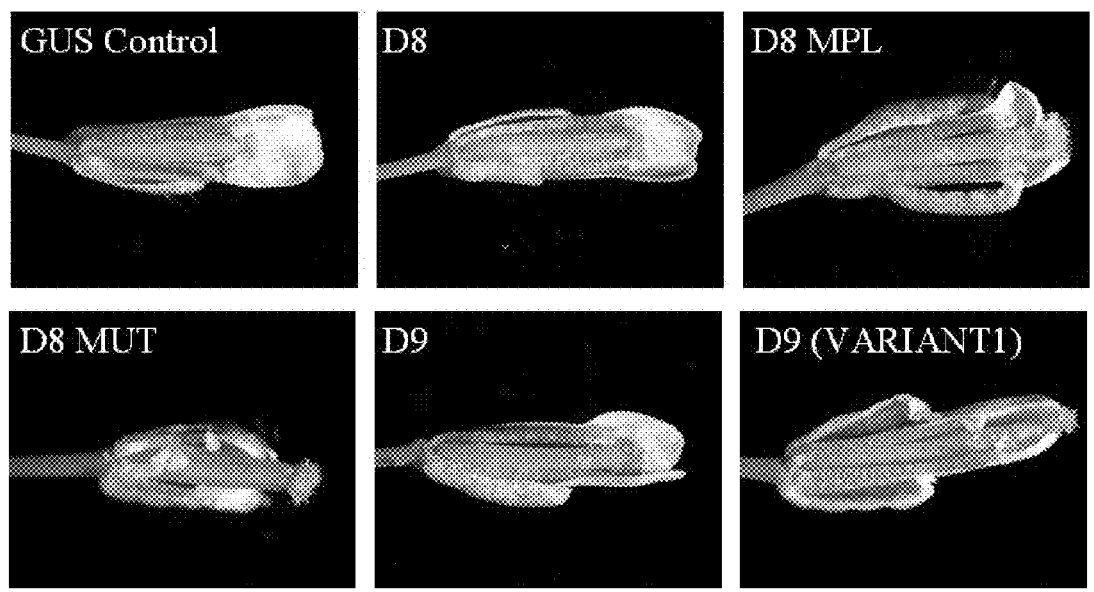
FIG. 5 depicts representative dissected flowers from *Arabidopsis thaliana* T1 plants comprising the maize DELLA cDNAs driven by the MS-S2a promoter. Two petals and two sepals were removed from the above flowers.

*Arabidopsis* T2 plants carrying maize DELLA cDNAs driven by the alfalfa vasculature sclerenchyma cell-preferred MS-S2a promoter have been produced. The dwarfing effects (from most severe to least severe) appear as follows Zm-D8 MUT>Zm-D8 MPL≧Zm-D9 MUT1>Zm-D8=Zm-D9 (see FIG. 4). Additionally, the transgenics appear to have altered flower morphology as seen in FIG. 5. In the Zm-D8 MUT, Zm-D8 MPL, Zm-D9 and Zm-D9 MUT1 the filaments appear to be preferentially shortened such that the anthers are shorter than the stigma. The Zm-D8 MUT transgenics appears most greatly affected and the Zm-D9 and Zm-D8 MPL transgenics least affected. The filaments of the GUS, and Zm-D8 transgenics appear unaffected. The particular Zm-D8 MUT transgenic line shown is also male sterile in that it is not shedding pollen.

The results disclosed in FIGS. 2-5 demonstrate conclusively that the putative Zm-D9 alleles that were isolated are bona fide alleles of Zm-D9. The isolated, wild type Zm-D9 is encoded on maize chromosome 5, as has been previously determined for Zm-D9 (Winkler and Freeling, 1994). When the protein encoded by Zm-D9 is translationally fused to a fluorescent marker protein it is found in a subcellular location consistent with the nucleus, as are other DELLA proteins. Most significantly, *Arabidopsis* transgenics carrying the Zm-D9 MUT1 allele are dwarfed while those carrying the wild type Zm-D9 are of normal stature. These results demonstrate that the mutant DELLA protein allele isolated from the dwarfed D9 mutant maize seedlings is indeed responsible for the maize dwarfism, verifying the identity of this gene as Zm-D9.

The effects on root architecture of expressing the maize DELLA proteins was also studied in the T2 *Arabidopsis* plants. All plants were grown under 18 h day length on an ArabiSun cart lighting system on vertical, square Petri plates. Average root length and the average number of root tips per plant were determined at ten days after germination and the results are summarized in Table 1. Plants carrying the Zm-D8 MPL, Zm-D8 MUT, and MUT1 Zm-D9 constructs had significant shorter average root lengths and significantly fewer root tips per plant than the control plants (GUS). Thus, the Zm-D9 gene, like the Zm-D8 gene, is involved in the control of root architecture, particularly root length and root branching (as evidenced by average number of root tips per plant).

TABLE 1

The Effects of Expressing Maize DELLA Proteins on the Root Architecture of Transgenic (T2) Arabidopsis Plants principal growth stage 1.03 (Boyes, et al., (2001) Plant Cell 13:1499-1510).

| Construct | Avg. Root Length (cm) | Avg. No. of Root Tips |
|---|---|---|
| MS-S2a PRO::GUS | $6.34^a$ | $9.73^d$ |
| MS-S2a PRO::Zm-D8 | $5.97^a$ | $9.10^d$ |
| MS-S2a PRO::Zm-D8 MPL | $4.82^c$ | $4.30^e$ |
| MS-S2a PRO::Zm-D8 MUT | $4.69^c$ | $5.00^e$ |
| MS-S2a PRO::Zm-D9 | $5.77^{ab}$ | $9.66^d$ |
| MS-S2a PRO::MUT1 Zm-D9 | $5.15^{bc}$ | $6.00^e$ |

Superscript letters indicate groups that are not significantly different from one another by LSD analysis at 95% confidence level. Data was collected from 4-15 replicates from 4 independent transformation events.

EXAMPLE 2

Transformation of Maize Plants with Zm-D9 and Regeneration of Transgenic Plants

Immature maize embryos from greenhouse donor plants are bombarded with a plasmid containing the Zm-D9 operably linked to the MS-S2A promoter (MS-S2a PRO) and the selectable marker gene PAT (Wohlleben, et al., (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the Zm-D9 operably linked to a promoter expressible in a plant is made. This plasmid DNA plus plasmid DNA containing a PAT selectable marker is precipitated onto 1.1 μm (average diameter) tungsten pellets using a $CaCl_2$ precipitation procedure as follows: 100 μl prepared tungsten particles in water; 10 μl (1 μg) DNA in Tris EDTA buffer (1 μg total DNA); 100 μl 2.5 M $CaCl_2$; and, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are bombarded at level #4 in a particle gun. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for plant height. MUT1 Zm-D9 plants are reduced in height at this stage by approximately 60%.

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

EXAMPLE 3

*Agrobacterium*-mediated Transformation of Maize with Zm-D9 and Regeneration of Transformed Plants For *Agrobacterium*-mediated transformation of maize with one or more of the Zm-D9 nucleotide polynucleotide molecules of the invention, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the Zm-D9 polynucleotide(s) of interest to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

EXAMPLE 4

Transformation of Soybean Embryos with Zm-D9 and Regeneration of Transformed Plants Culture Conditions Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the following examples by the method of particle gun bombardment (Klein, et al., (1987) Nature, 327:70).

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the genes of interest and the selectable marker gene are used for bombardment. Plasmid DNAs for bombardment are routinely prepared and purified using the method described in the Promega™ Protocols and Applications Guide, Second Edition (page 106). Fragments of the plasmids carrying the Zm-D9 polynucleotide are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing the Zm-D9 polynucleotide are cut from the agarose gel. DNA is purified from the agarose using the GELase digesting enzyme following the manufacturer's protocol.

A 50 µl aliquot of sterile distilled water containing 3 mg of gold particles (3 mg gold) is added to 5 µl of a 1 µg/µl DNA solution (either intact plasmid or DNA fragment prepared as described above), 50 µl 2.5M $CaCl_2$ and 20 µl of 0.1 M spermidine. The mixture is shaken 3 min on level 3 of a vortex shaker and spun for 10 sec in a bench microfuge. After a wash with 400 µl 100% ethanol the pellet is suspended by sonication in 40 µl of 100% ethanol. Five µl of DNA suspension is dispensed to each flying disk of the Biolistic PDS100/HE instrument disk. Each 5 µl aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for proteins.

Media Recipes

| SB 196 - FN Lite liquid proliferation medium (per liter) - | |
|---|---|
| MS FeEDTA - 100x Stock 1 | 10 ml |
| MS Sulfate - 100x Stock 2 | 10 ml |
| FN Lite Halides - 100x Stock 3 | 10 ml |

-continued

| SB 196 - FN Lite liquid proliferation medium (per liter) - | |
| --- | --- |
| FN Lite P, B, Mo - 100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2 SO 4 | 0.463 gm |
| Asparagine | 1.0 gm |
| Sucrose (1%) | 10 gm |
| pH 5.8 | |

FN Lite Stock Solutions

| Stock # | 1000 ml | 500 ml |
| --- | --- | --- |
| 1 MS Fe EDTA 100x Stock | | |
| Na$_2$ EDTA* | 3.724 g | 1.862 g |
| FeSO$_4$—7H$_2$O | 2.784 g | 1.392 g |
| 2 MS Sulfate 100x stock | | |
| MgSO$_4$—7H$_2$O | 37.0 g | 18.5 g |
| MnSO$_4$—H$_2$O | 1.69 g | 0.845 g |
| ZnSO$_4$—7H$_2$O | 0.86 g | 0.43 g |
| CUSO$_4$—5H$_2$O | 0.0025 g | 0.00125 g |
| 3 FN Lite Halides 100x Stock | | |
| CaCl$_2$—2H$_2$O | 30.0 g | 15.0 g |
| KI | 0.083 g | 0.0715 g |
| CoCl$_2$—6H$_2$O | 0.0025 g | 0.00125 g |
| 4 FN Lite P, B, Mo 100x Stock | | |
| KH$_2$PO$_4$ | 18.5 g | 9.25 g |
| H$_3$BO$_3$ | 0.62 g | 0.31 g |
| Na$_2$MoO$_4$—2H$_2$O | 0.025 g | 0.0125 g |

*Add first, dissolve in dark bottle while stirring

SB1 solid medium (per liter) comprises: 1 pkg. MS salts (Gibco/BRL-Cat# 11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat# 11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL—Cat# 11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/sucrose (Gibco/BRL—Cat# 21153-036); pH 5.7; and, 5 g TC agar.

2,4-D stock is obtained premade from Phytotech cat# D 295—concentration is 1 mg/ml.

B5 Vitamins Stock (per 100 ml) which is stored in aliquots at −20° C. comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide.

EXAMPLE 5

Sunflower Meristem Tissue Transformation with Zm-D9 and Regeneration of Transformed Plants Sunflower meristem tissues are transformed with an expression cassette containing a Zm-D9 polynucleotide molecule of the invention operably linked to the MS-S2A promoter as follows (see also, European Patent Number EP 0 486233, herein incorporated by reference, and Malone-Schoneberg, et al., (1994) *Plant Science* 103:199-207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer, et al., (Schrammeijer, et al., (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant.*, 15:473-497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA$_3$), pH 5.6, and 8 g/l Phytagar.

The explants are subjected to microprojectile bombardment prior to *Agrobacterium* treatment (Bidney, et al., (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the Zm-D9 polynucleotide molecule operably linked to the promoter is introduced into *Agrobacterium* strain EHA105 via freeze-thawing as described by Holsters, et al., (1978) *Mol. Gen. Genet.* 163:181-187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an OD$_{600}$ of about 0.4 to 0.8. The *Agrobacterium* cells are pelleted and resuspended at a final OD$_{600}$ of 0.5 in an inoculation medium comprised of 12.5 mM MES pH 5.7, 1 gm/l NH$_4$Cl, and 0.3 gm/l MgSO$_4$.

Freshly bombarded explants are placed in an *Agrobacterium suspension*, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for Zm-D9 activity.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA of leaf extracts.

EXAMPLE 6

Expression and Characterization of Zm-D9

Figure 10:
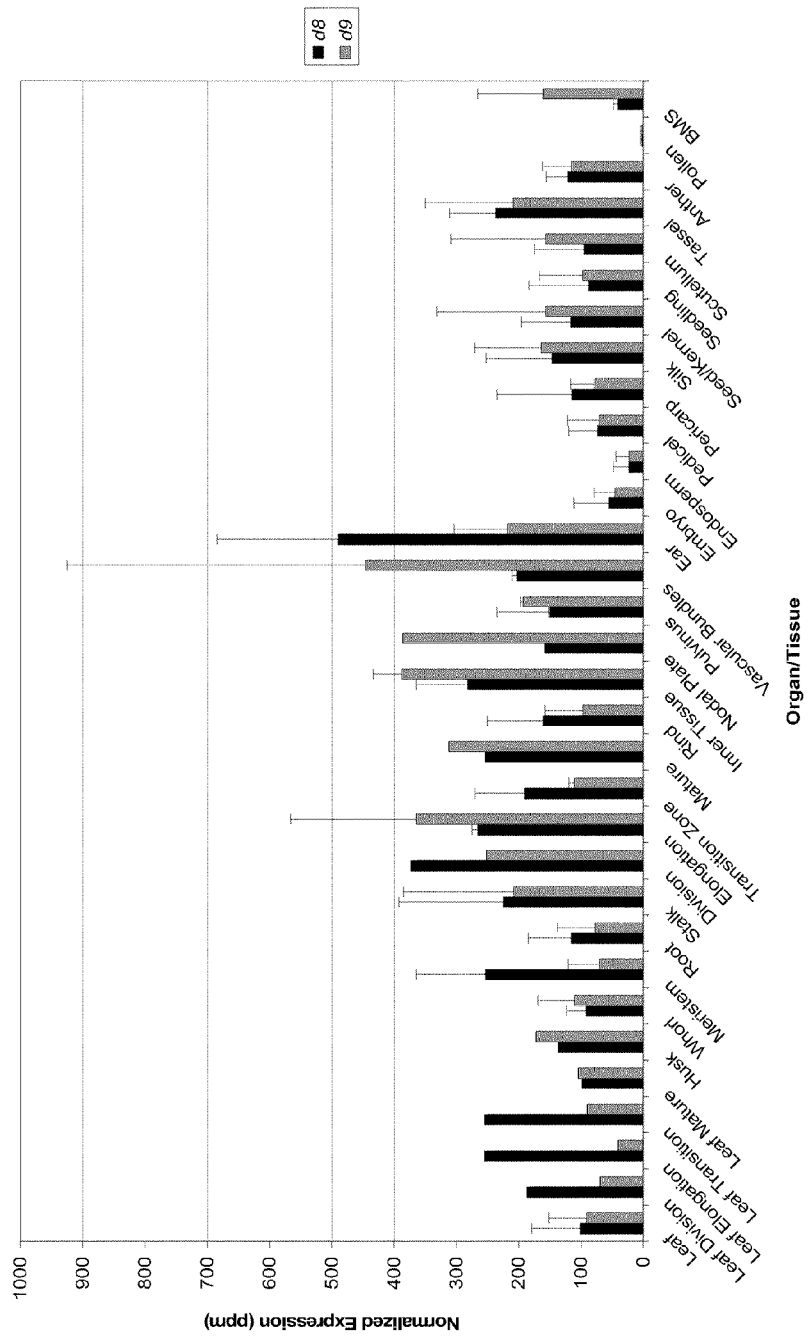
FIG. 10 represents the relative expression levels (in ppm) of the d8 and d9 genes in 32 different tissues and developmental stages of maize obtained via the Lynx MPSS system (Brenner, et al., (2000) *PNAS* 97:1665-1670 and Brenner, et al., (2000) *Nat Biotechnol* 18:630-634). Vertical lines divide the chart by the organ from which the samples were derived.

Expression profiles show that from a developmental standpoint, d9 shows preference for mature, differentiated cells, particularly those associated with stalk, while d8 is more associated with the dividing or meristematic cells (FIG. 10). For example, d8 is expressed significantly higher in meristems, the division region of the stalk (internode) and transition zone, while d8 and d9 are expressed roughly at parity in the mature zone of the internode. The highest expression levels for d8 and d9 were in ears and vascular bundles, respectively. In general, vascular organs/tissues had greater expression of both genes than did non-vascular organs/tissues. This is consistent with a presence of DELLA mRNAs and proteins in and around the vasculature in dicots (Haywood, et al., (2005) *Plant Journal* 42:49-68; Israelsson, et al., (2005) *Plant Journal* 44:494-504) and suggests that the localization has been conserved between dicots and monocots.

Figure 11A:
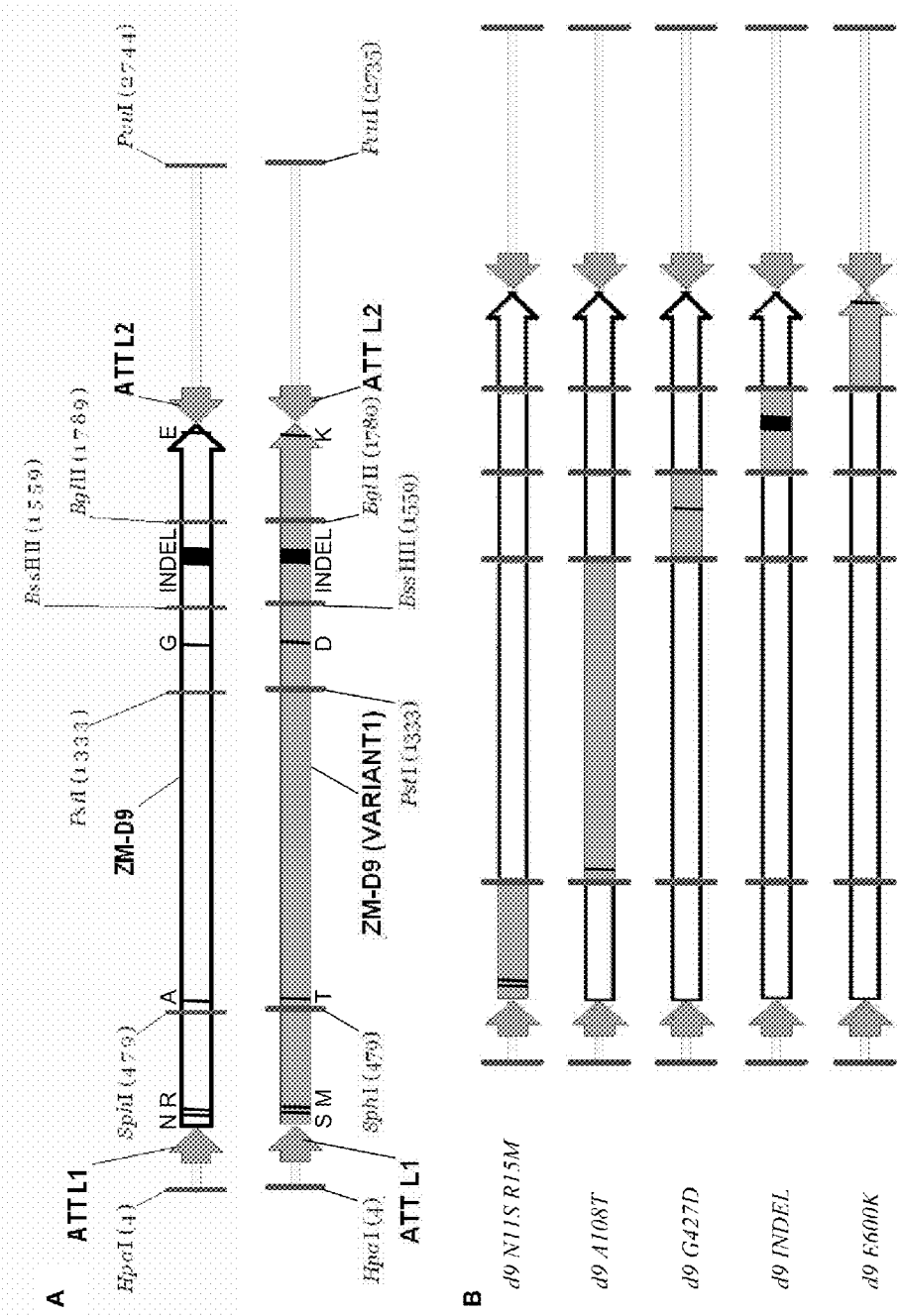
FIG. 11 presents partial d9 and D9 entry clone maps representing the domain swap chimeras that were produced. A—shows partial maps of the d9 and D9 entry clones with the amino acid differences encoded in each region denoted. The amino acid sequence of the d9 INDEL is SGSGSGQPT-DASPPA (SEQ ID NO: 7). The MUT1 D9 INDEL amino acid sequence is QPTDASSPAAG (SEQ ID NO: 8). B—shows partial maps of the d9 allele based (white regions) chimeras with segments of MUT1 D9 in grey. C—shows partial maps of the MUT1 D9 allele based (grey regions) chimeras with segments of d9 in white.
Figure 11B:
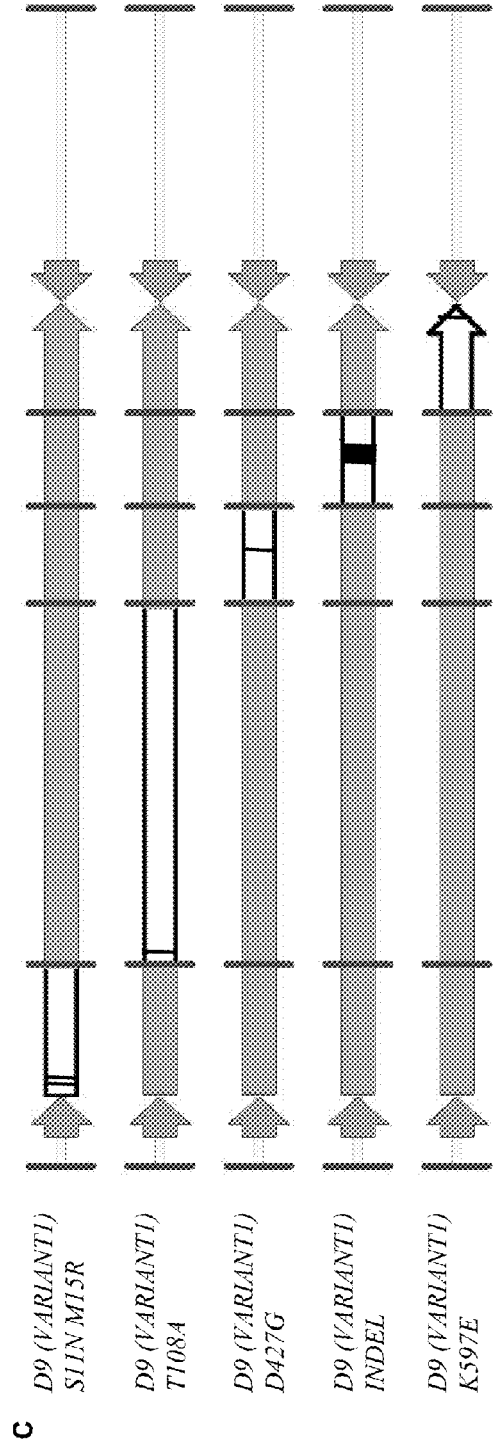

To further dissect the nature of the D9 allele, domain swap constructs were created and transformed into *Arabidopsis*. Five genetic regions were exchanged between the d9 and D9 entry clones (FIG. 11), and the resultant chimeric entry clones were used to create S2A PRO::DELLA intermediate and co-integrate vectors for transformation as described for the native maize alleles. Morphometric analysis of the domain swap transgenics was performed at the T1 generation (FIG. 14). The E600K mutation from D9 is necessary and sufficient for the dwarfing and earlier flowering phenotypic changes. The d9 E600K and the D9 K597E produced morphological effects dissimilar to their backbone alleles (FIG. 14). The most notable differences were in plant height, silique length, days to flowering, and number of rosette leaves at flowering. In all four cases, the d9 (E600K) plants showed characteristics similar to D9. On average, the d9 (E600K) chimera produced plants with the shortest stems and siliques and had the fewest rosette leaves at flowering of any of the ten constructs. Conversely, D9 K597E ranked second or third highest for silique length, day to flowering, and number of rosette leaves at flowering. No other polymorphism displayed a clear pattern of stature or flowering time changes. This mutation and other mutations might therefore have specific application in changing the stature of corn toward a grain type, high yield potential architecture.

The maize DELLA dwarfing alleles were found to hasten *Arabidopsis flowering*. D8 MPL and D8 MUT shifted flowering approximately 6 days earlier (FIG. 12). Strikingly, D9 accelerated flowering by 11 days (26.5%). This effect appears to be linked to gibberellin-insensitivity since flowering times of the d8 and d9 transgenics were not significantly different from the GUS control. The D9 gene causes later flowering in T0 GS3× Gaspe Flint (FIG. 13), while d9 led to earlier flowering (using total above ground nodes as a basis for maturity shift; FIG. 12). No flowering time alteration has been observed in d8 or D8 MPL transgenic maize.

The MS-S2A promoter was selected to drive expression of five maize DELLA alleles in transgenic *Arabidopsis*. The rice Actin1 promoter was used to drive these alleles in *Arabidopsis* in an earlier set of transgenics. T1 plants from these transformations did not display any visible phenotype, suggesting that the rice Actin 1 promoter was not expressing the DELLA proteins in proper tissues. Given this result, the maize expression profiles for d8 and d9 (FIG. 10), and the work of Haywood, et al., ((2005) *Plant Journal* 42:49-68) which showed a vasculature association of DELLA proteins and mRNAs in three species, the MS-S2A promoter was chosen for maize DELLA expression in *Arabidopsis* and maize. A transgenic approach was chosen so that a direct comparison of the maize alleles could be performed that would not be skewed by promoter dependent effects. These data establish the use of tissue specific promoters as a strategy to change plant architecture.

EXAMPLE 7

Variants of Zm-D9

A. Variant Nucleotide Sequences of Zm-D9 (SEQ ID NO: 1, 3, 4 or 6) That Do Not Alter the Encoded Amino Acid Sequence The Zm-D9 nucleotide sequence set forth in SEQ ID NO: 1, 3, 4 or 6 is used to generate variant nucleotide sequences having the nucleotide sequence of the open reading frame with about 70%, 76%, 81%, 86%, 92% and 97% nucleotide sequence identity when compared to the starting unaltered ORF nucleotide sequence of SEQ ID NO: 1, 3, 4 or 6. These functional variants are generated using a standard codon table. While the nucleotide sequence of the variant is altered, the amino acid sequence encoded by the open reading frame does not change.

B. Variant Amino Acid Sequences of Zm-D9

Figure 7A:
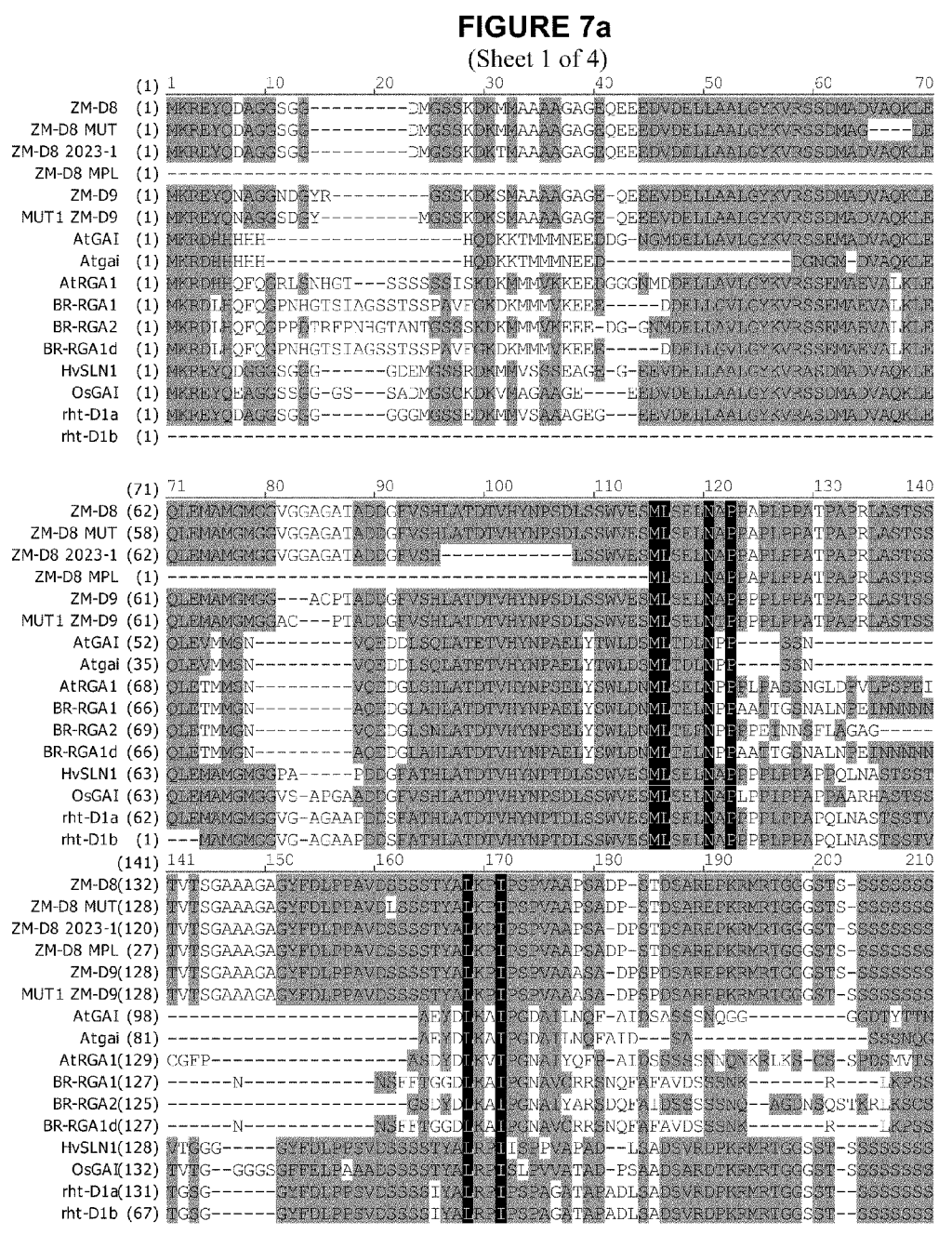
Figure 7C:
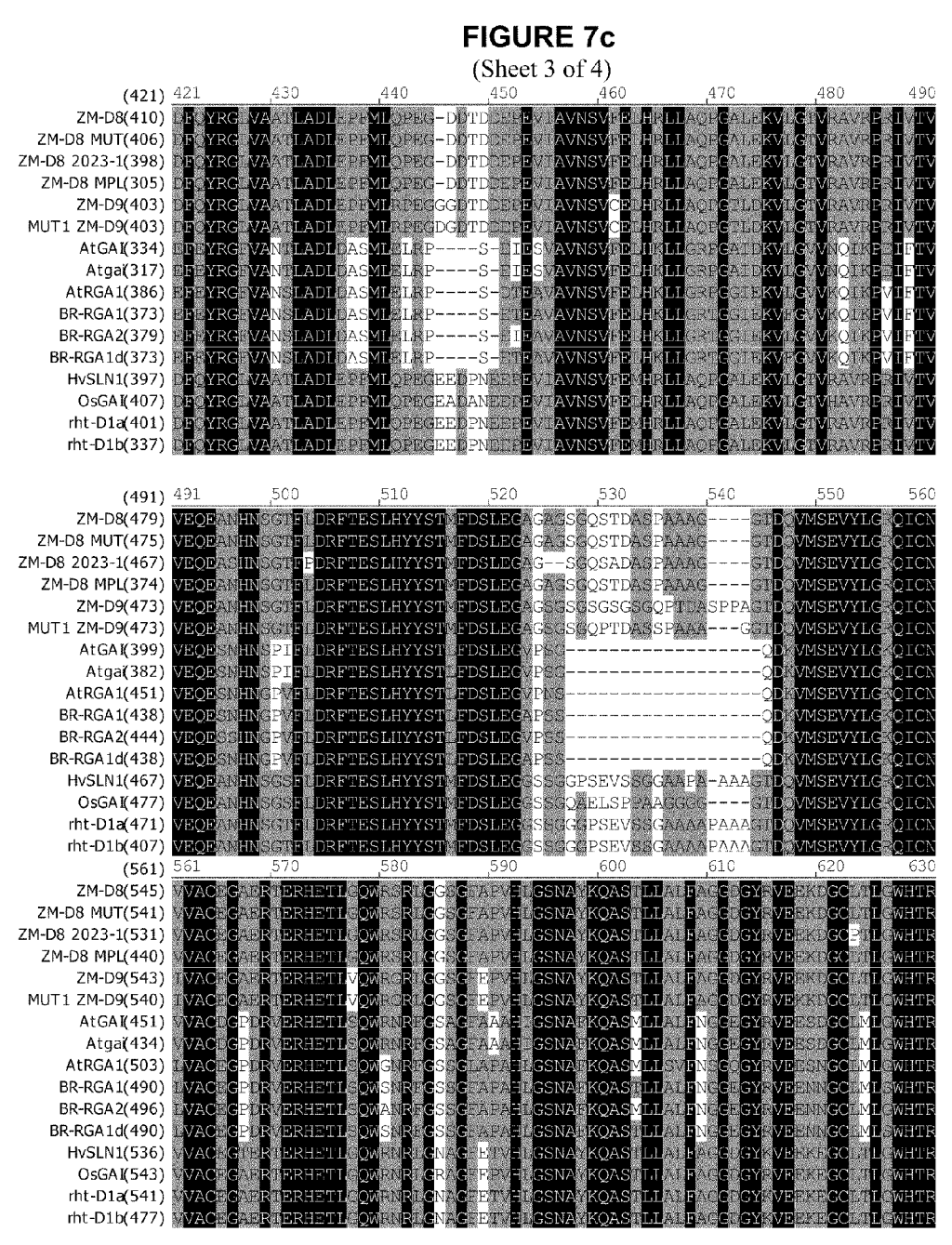

Variant amino acid sequences of Zm-D9 are generated. In this example, one amino acid is altered. Specifically, the amino acid sequence set forth in SEQ ID NO: 2 or 5 is reviewed to determine the appropriate amino acid alteration. The selection of the amino acid to change is made by consulting the protein alignment (with the other orthologs and other gene family members from various species). See FIG. 7. An amino acid is selected that is deemed not to be under high selection pressure (not highly conserved) and which is rather easily substituted by an amino acid with similar chemical characteristics (i.e., similar functional side-chain). Using the protein alignment set forth in FIG. 7 an appropriate amino acid can be changed. Once the targeted amino acid is identified, the procedure outlined in Example 6A is followed. Variants having about 70%, 75%, 81%, 86%, 92% and 97% nucleic acid sequence identity to SEQ ID NO: 1, 3, 4, or 6 are generated using this method.

C. Additional Variant Amino Acid Sequences of Zm-D9

In this example, artificial protein sequences are created having 82%, 87%, 92% and 97% identity relative to the reference protein sequence. This latter effort requires identifying conserved and variable regions from the alignment set forth in FIG. 7 and then the judicious application of an amino acid substitutions table. These parts will be discussed in more detail below.

Largely, the determination of which amino acid sequences are altered is made based on the conserved regions among Zm-D9 protein or among the other DELLA proteins. See FIG. 7. Based on the sequence alignment, the various regions of the Zm-D9 protein that can likely be altered are represented in lower case letters, while the conserved regions are represented by capital letters. It is recognized that conservative substitutions can be made in the conserved regions below without altering function. In addition, one of skill will understand that functional variants of a Zm-D9 amino acid sequence of the invention can have minor non-conserved amino acid alterations in the conserved domain.

The conserved regions are found between about amino acids 37 to 109, 224 to 504, 528 to 625, of SEQ ID NO: 2. The non-conserved regions are from about amino acids 1 to 36, 110 to 223, 505 to 527, of SEQ ID NO: 2.

Artificial protein sequences are then created that are different from the original in the intervals of 80-85%, 85-90%, 90-95%, and 95-100% identity. Midpoints of these intervals are targeted, with liberal latitude of plus or minus 1%, for example. The amino acids substitutions will be effected by a custom Perl script. The substitution table is provided below in Table 2.

TABLE 2

Substitution Table

| Amino Acid | Strongly Similar and Optimal Substitution | Rank of Order to Change | Comment |
|---|---|---|---|
| I | L,V | 1 | 50:50 substitution |
| L | I,V | 2 | 50:50 substitution |
| V | I,L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C, and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involved a 50:50 substitution of the two alternate optimal substitutions.

The variant amino acid sequences are written as output. Perl script is used to calculate the percent identities. Using this procedure, variants of a Zm-D9 protein are generating having about 82%, 87%, 92% and 97% amino acid identity to the starting unaltered ORF nucleotide sequence of SEQ ID NO: 1, 3, 4 or 6.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXAMPLE 8

Expression and Characterization of Zm-D9 in Maize

Domain swap constructs (see example 6) d9 E600k and D9 K597E were tested in maize (T0 generation) to determine their effect on plant height, leaf number, days to tassel emergence, days to first pollen shed, and days to pollination. The phenotypic data of d9 E600k and D9 K597E were compared to the data using the MUT1 Zm-D9 allele and the Zm-D8 MPL allele. In all cases the S2a promoter was used to drive expression of the respective structural genes. Vector construction was as detailed in example 6. The plant height of D9 K597E was not altered compared non-transformed maize plants of the same genotype growing at the same time in the greenhouse. Similarly, leaf number, days to tassel emergence, days to first pollen shed, and days to pollination of D9 K597E was similar to non transformed plants. On average, the MUT1 D9 and d9 E600K transgenics had one additional leaf compared to D9 K597E. The d9 E600 K and MUT1 D9 transgenics were dramatically reduced in height (50% and 30% reduced respectively) compared to D9 K597E. On the other hand, d9 E600k and MUT1 D9 were delayed in tassel emergence, pollen shed and in pollination date compared to D9 K597E. The pollen shed was delayed up to 14 days with MUT1 D9 and 10 days with d9 E600k. Pollination delay was similar with these transgenic plants. In addition, these transgenics showed approximately one extra node compared to D9 K597E. These data show a similar pattern to *Arabidopsis* for height (shorter stems) but the opposite phenotype for maturity shift in which the MUT1 D9 and d9 E600k have delayed maturity. These data confirm the significance of this polymorphism for stature and flowering time changes in both *Arabidopsis* and maize. The MUT1 D9 and d9 E600k mutations might have specific application in changing stature, node number, or maturity in an alternative plant architecture in a grain type, high yield potential architecture in corn.

That which is claimed:

1. An isolated polynucleotide molecule comprising a nucleotide sequence selected from the group consisting of:
   (a) the nucleotide sequence comprising SEQ ID NO: 4; and
   (b) a nucleotide sequence encoding an amino acid sequence comprising SEQ ID NO: 5.

2. An expression cassette comprising the polynucleotide molecule of claim 1.

3. The expression cassette of claim 2, wherein said polynucleotide molecule is operably linked to a promoter that drives expression in a plant.

4. A non-human host cell comprising the expression cassette of claim 2 or 3.

5. The host cell of claim 4, wherein said host cell is a plant cell, a bacterial cell, or a fungal cell.

6. A plant comprising an isolated polynucleotide molecule operably linked to a promoter that drives expression in the plant, wherein said polynucleotide molecule comprises a nucleotide sequence selected from the group consisting of:
   (a) the nucleotide sequence comprising SEQ ID NO: 4; and
   (b) a nucleotide sequence encoding an amino acid sequence comprising SEQ ID NO: 5.

7. A plant cell of the plant of claim 6.

8. The plant of claim 6, wherein said plant is a monocot.

9. The plant of claim 8, wherein said monocot is selected from the group consisting of maize, wheat, rice, sorghum, rye, millet and barley.

10. The plant of claim 6, wherein said plant is a dicot.

11. The plant of claim 10, wherein said dicot is selected from the group consisting of *Arabidopsis*, soybean, sunflower, safflower, alfalfa, *Brassica*, cotton, and peanut.

12. The plant of any one of claims 6 to 11, wherein said polynucleotide molecule is stably incorporated into the genome of the plant.

13. A transformed seed of the plant of claim 12, wherein the seed comprises the polynucleotide molecule.

* * * * *

SEQUENCE LISTING

<160> NUMBER OF SEQ ID NOS: 8

<210> SEQ ID NO 1
<211> LENGTH: 1878
<212> TYPE: DNA
<213> ORGANISM: Zea mays

<400> SEQUENCE: 1

```
atgaagcgcg agtaccaaaa cgccggcggg aacgacggct acaggggctc ctccaaggac      60
aagtcgatgg cggcggcggc gggggcaggg gagcaggagg aggaggtgga cgagctgctg     120
gcggcgctcg ggtacaaggt gcgttcgtcg gatatggcgg acgtcgcgca gaagctagag     180
cagctcgaga tggccatggg gatgggcggc gcctgcccca ccgctgatga cgggttcgtc     240
tcgcacctcg ccacggacac cgtgcactac aatccctccg acctgtcgtc ctgggtcgag     300
agcatgctgt ccgagctcaa cgcgcccccg ccgccgctcc cacccgcgac gccggcacca     360
aggctggcgt ccacctcgtc caccgtcaca gtggcgccg ccgccggtgc cggctacttc      420
gatctcccgc ccgccgtcga ctcgtccagc agtacctacg ctctgaagcc gatccctcg      480
ccggtggcgg cggcgtcggc cgacccgtcc ccggactcgg cgcgggagcc caagcggatg     540
cgaactggcg gcggcagcac gtcgtcgtcc tcttcctcgt cgtcatccat ggacggcggc     600
cgcactagga gctccgtggt cgaagctgcc ccgccggcga cgcaggcggc caacgggccg     660
gcggtgccgg tggtggtggt ggacacgcag gaggccggga tccggctggt gcacgcgctg     720
ctggcgtgcg cggaggccgt gcagcaggag aacttctctg cggcggacgc gctggtgaag     780
cagatccccg tgctggcctc gtcgcagggc ggcgccatgc gcaaggtcgc cgcctacttc     840
ggcgaggcgc tcgcccggcg cgtgtatcgc ctccgcccgg caccgacgg ctcccctcctc       900
gacgccgcct tcgccgacct cctgcacgcg cacttctacg agtcctgccc ctacctcaag     960
ttcgcccact tcaccgcgaa ccaggccatc ctcgaggctt cgccgggtg ccgccgcgtc      1020
cacgtcgtcg acttcggcat caagcagggg atgcagtggc cggctctcct ccaggccctc     1080
gccctccgcc ccggcggccc cccgtcgttc cgtctcaccg gcgtaggccc gccgcagccc     1140
gacgagaccg acgccctgca gcaggtgggc tggaagctcg cccagttcgc gcacaccatc     1200
cgcgtcgact ccagtaccg tggcctcgtc gccgccacgc tcgctgacct ggagccgttc     1260
atgctgcgac cggagggcgg cggcgacacg gacgacgagc ccgaggtgat cgccgtaaac     1320
tcggtgtgcg agctgcaccg gctgctcgcg cagcccggta cactcgacaa ggtcctgggc     1380
accgtgcgcg cggtgcggcc gaggatcgtg acggtggtgg agcaggaggc caaccacaac     1440
tccggcacat tcctcgaccg cttcacggag tcgctgcact actactccac catgttcgac     1500
tccctcgagg gcgccggctc aggctccggc tccggctccg gctccggcca gcccaccgac     1560
gcctccccgc cggccggcac ggaccaggtg atgtccgagg tgtacctcgg ccggcagatc     1620
tgcaacatcg tggcgtgcga gggcgccgag cgcacggagc ccacgagac gctggtccag     1680
tggcgcggcc gcctcggcgg gtccgggttc gagcccgtgc acctgggatc caacgcctac     1740
aagcaggcaa gcacgctgct ggccctcttc gccggcggcg acgggtacag ggtggaggag     1800
aaggacgggt gcctgactct gggatggcat acgcgcccgc tcatcgccac ctcggcgtgg     1860
cgcgtcgccg ctccgtga                                                  1878
```

<210> SEQ ID NO 2
<211> LENGTH: 625
<212> TYPE: PRT
<213> ORGANISM: Zea mays

<400> SEQUENCE: 2

```
Met Lys Arg Glu Tyr Gln Asn Ala Gly Gly Asn Asp Gly Tyr Arg Gly
  1               5                  10                  15

Ser Ser Lys Asp Lys Ser Met Ala Ala Ala Gly Ala Gly Glu Gln
                 20                  25                  30

Glu Glu Glu Val Asp Glu Leu Leu Ala Ala Leu Gly Tyr Lys Val Arg
                 35                  40                  45

Ser Ser Asp Met Ala Asp Val Ala Gln Lys Leu Glu Gln Leu Glu Met
             50                  55                  60

Ala Met Gly Met Gly Gly Ala Cys Pro Thr Ala Asp Asp Gly Phe Val
 65                  70                  75                  80

Ser His Leu Ala Thr Asp Thr Val His Tyr Asn Pro Ser Asp Leu Ser
                 85                  90                  95

Ser Trp Val Glu Ser Met Leu Ser Glu Leu Asn Ala Pro Pro Pro Pro
                100                 105                 110

Leu Pro Pro Ala Thr Pro Ala Pro Arg Leu Ala Ser Thr Ser Ser Thr
            115                 120                 125

Val Thr Ser Gly Ala Ala Gly Ala Gly Tyr Phe Asp Leu Pro Pro
            130                 135                 140

Ala Val Asp Ser Ser Ser Ser Thr Tyr Ala Leu Lys Pro Ile Pro Ser
145                 150                 155                 160

Pro Val Ala Ala Ala Ser Ala Asp Pro Ser Pro Asp Ser Ala Arg Glu
                165                 170                 175

Pro Lys Arg Met Arg Thr Gly Gly Gly Ser Thr Ser Ser Ser Ser Ser
                180                 185                 190

Ser Ser Ser Ser Met Asp Gly Gly Arg Thr Arg Ser Ser Val Val Glu
            195                 200                 205

Ala Ala Pro Pro Ala Thr Gln Ala Ala Asn Gly Pro Ala Val Pro Val
        210                 215                 220

Val Val Val Asp Thr Gln Glu Ala Gly Ile Arg Leu Val His Ala Leu
225                 230                 235                 240

Leu Ala Cys Ala Glu Ala Val Gln Gln Glu Asn Phe Ser Ala Ala Asp
                245                 250                 255

Ala Leu Val Lys Gln Ile Pro Val Leu Ala Ser Ser Gln Gly Gly Ala
                260                 265                 270

Met Arg Lys Val Ala Ala Tyr Phe Gly Glu Ala Leu Ala Arg Arg Val
            275                 280                 285

Tyr Arg Leu Arg Pro Ala Pro Asp Gly Ser Leu Leu Asp Ala Ala Phe
        290                 295                 300

Ala Asp Leu Leu His Ala His Phe Tyr Glu Ser Cys Pro Tyr Leu Lys
305                 310                 315                 320

Phe Ala His Phe Thr Ala Asn Gln Ala Ile Leu Glu Ala Phe Ala Gly
                325                 330                 335

Cys Arg Arg Val His Val Val Asp Phe Gly Ile Lys Gln Gly Met Gln
                340                 345                 350

Trp Pro Ala Leu Leu Gln Ala Leu Ala Leu Arg Pro Gly Gly Pro Pro
            355                 360                 365

Ser Phe Arg Leu Thr Gly Val Gly Pro Pro Gln Pro Asp Glu Thr Asp
        370                 375                 380
```

```
Ala Leu Gln Gln Val Gly Trp Lys Leu Ala Gln Phe Ala His Thr Ile
385                 390                 395                 400

Arg Val Asp Phe Gln Tyr Arg Gly Leu Val Ala Ala Thr Leu Ala Asp
            405                 410                 415

Leu Glu Pro Phe Met Leu Arg Pro Glu Gly Gly Asp Thr Asp Asp
        420                 425                 430

Glu Pro Glu Val Ile Ala Val Asn Ser Val Cys Glu Leu His Arg Leu
    435                 440                 445

Leu Ala Gln Pro Gly Thr Leu Asp Lys Val Leu Gly Thr Val Arg Ala
    450                 455                 460

Val Arg Pro Arg Ile Val Thr Val Val Glu Gln Ala Asn His Asn
465                 470                 475                 480

Ser Gly Thr Phe Leu Asp Arg Phe Thr Glu Ser Leu His Tyr Tyr Ser
                485                 490                 495

Thr Met Phe Asp Ser Leu Glu Gly Ala Gly Ser Gly Ser Gly
        500                 505                 510

Ser Gly Ser Gly Gln Pro Thr Asp Ala Ser Pro Ala Gly Thr Asp
    515                 520                 525

Gln Val Met Ser Glu Val Tyr Leu Gly Arg Gln Ile Cys Asn Ile Val
530                 535                 540

Ala Cys Glu Gly Ala Glu Arg Thr Glu Arg His Glu Thr Leu Val Gln
545                 550                 555                 560

Trp Arg Gly Arg Leu Gly Gly Ser Gly Phe Glu Pro Val His Leu Gly
                565                 570                 575

Ser Asn Ala Tyr Lys Gln Ala Ser Thr Leu Leu Ala Leu Phe Ala Gly
                580                 585                 590

Gly Asp Gly Tyr Arg Val Glu Glu Lys Asp Gly Cys Leu Thr Leu Gly
            595                 600                 605

Trp His Thr Arg Pro Leu Ile Ala Thr Ser Ala Trp Arg Val Ala Ala
    610                 615                 620

Pro
625

<210> SEQ ID NO 3
<211> LENGTH: 1875
<212> TYPE: DNA
<213> ORGANISM: Zea mays

<400> SEQUENCE: 3
atgaagcgcg agtaccaaaa cgccggcggg aacgacggct acaggggctc ctccaaggac      60
aagtcgatgg cggcggcggc gggggcaggg gagcaggagg aggaggtgga cgagctgctg     120
gcggcgctcg ggtacaaggt gcgttcgtcg gatatggcgg acgtcgcgca gaagctagag     180
cagctcgaga tggccatggg gatgggcggc gcctgcccca ccgctgatga cgggttcgtc     240
tcgcacctcg ccacggacac cgtgcactac aatccctccg acctgtcgtc ctgggtcgag     300
agcatgctgt ccgagctcaa cgcgcccccg ccgccgctcc cacccgcgac gccggcacca     360
aggctggcgt ccacctcgtc caccgtcaca agtggcgccg ccgccggtgc cggctacttc     420
gatctcccgc ccgccgtcga ctcgtccagc agtacctacg ctctgaagcc gatcccctcg     480
ccggtggcgc ggcgtcggc cgacccgtcc ccggactcgg cgcgggagcc caagcggatg     540
cgaactggcg gcggcagcac gtcgtcgtcc tcttcctcgt cgtcatccat ggacggcggc     600
cgcactagga gctccgtggt cgaagctgcc ccgccggcga cgcaggcggc caacgggccg     660
gcggtgccgg tggtggtggt ggacacgcag gaggccggga tccggctggt gcacgcgctg     720
```

```
ctggcgtgcg cggaggccgt gcagcaggag aacttctctg cggcggacgc gctggtgaag      780 cagatcccg  tgctggcctc gtcgcagggc ggcgccatgc gcaaggtcgc cgcctacttc      840
ggcgaggcgc tcgcccggcg cgtgtatcgc ctccgcccgg caccgacgg  ctccctcctc      900 gacgccgcct tcgccgacct cctgcacgcg cacttctacg agtcctgccc ctacctcaag      960
ttcgcccact tcaccgcgaa ccaggccatc ctcgaggctt cgccggggtg ccgccgcgtc     1020
cacgtcgtcg acttcggcat caagcagggg atgcagtggc cggctctcct ccaggccctc     1080
gccctccgcc ccggcggccc cccgtcgttc cgtctcaccg gcgtaggccc gccgcagccc     1140
gacgagaccg acgccctgca gcaggtgggc tggaagctcg cccagttcgc gcacaccatc     1200
cgcgtcgact tccagtaccg tggcctcgtc gccgccacgc tcgctgacct ggagccgttc     1260
atgctgcgac cggagggcgg cggcgacacg gacgacgagc ccgaggtgat cgccgtaaac     1320
tcggtgtgcg agctgcaccg gctgctcgcg cagcccggta cactcgacaa ggtcctgggc     1380
accgtgcgcg cggtgcggcc gaggatcgtg acggtggtgg agcaggaggc caaccacaac     1440
tccggcacat tcctcgaccg cttcacggag tcgctgcact actactccac catgttcgac     1500
tccctcgagg gcgccggctc aggctccggc tccggctccg gctccggcca gcccaccgac     1560
gcctccccgc cggccggcac ggaccaggtg atgtccgagg tgtacctcgg ccggcagatc     1620
tgcaacatcg tggcgtgcga gggcgccgag cgcacggagc ccacgagac  gctggtccag     1680 tggcgcggcc gcctcggcgg gtccgggttc gagcccgtgc acctgggatc caacgcctac     1740
aagcaggcaa gcacgctgct ggccctcttc gccggcggcg acgggtacag ggtggaggag     1800
aaggacgggt gcctgactct gggatggcat acgcgcccgc tcatcgccac ctcggcgtgg     1860
cgcgtcgccg ctccg                                                     1875

<210> SEQ ID NO 4
<211> LENGTH: 1869
<212> TYPE: DNA
<213> ORGANISM: Zea mays

<400> SEQUENCE: 4
atgaagcgcg agtaccaaaa cgccggcggg agcgacggct acatggggtc ctccaaggac       60
aagtcgatgg cggcggcggc gggggcaggg gagcaggagg aggaggtgga cgagctgctg      120
gcggcgctcg ggtacaaggt gcgttcgtcg gatatggcgg acgtcgcgca gaagctagag      180
cagctcgaga tggccatggg gatgggcggc cctgccccca ccgctgatga cgggttcgtc      240
tcgcacctcg ccacggacac cgtgcactac aatccctccg acctgtcgtc ctgggtcgag      300
agcatgctat ccgagctcaa cacgcccccg ccgccgctcc cgcccgcgac gccggcacca      360
aggctcgcgt ccacctcgtc caccgtcaca agtggcgccg ccgccggtgc cggctacttc      420 gatctccccgc ccgccgtcga ctcgtccagc agtacctacg ctctgaagcc gatcccctcg      480
ccggtggcgg cggcgtcggc cgacccgtcc ccggactcgg cgcgggagcc caagcggatg      540
cgaactggcg gcggcagcac gtcgtcgtcc tcttcctcgt cgtcatccat ggacggcggc      600
cgcactagga gctccgtggt cgaagctgcc ccgccggcga cgcaggcggc caacgggccc      660
gcggtgccgg tggtggtggt ggacacgcag gaggccggta ccggctggt  gcacgcgctg      720 ctggcgtgcg cggaggccgt gcagcaggag aacttctctg cggcggacgc gctggtgaag      780 cagatcccg  tgctggcctc gtcgcagggc ggcgccatgc gcaaggtcgc cgcctacttc      840
ggcgaggcgc tcgcccggcg cgtgtatcgc ctccgcccgg caccgacgg  ctccctcctc      900 gacgccgcct tcgccgacct cctgcacgcg cacttctacg agtcctgccc ctacctcaag      960
```

-continued

```
ttcgcccact tcaccgcgaa ccaggccatc ctcgaggctt cgccgggtg ccgccgcgtc      1020 cacgtcgtcg acttcggcat caagcagggg atgcagtggc cggctctcct ccaggccctc      1080
gccctccgcc ccgtggcccc ccgtcgttc cgtctcaccg gcgtaggccc gccgcagccc      1140
gacgagaccg acgccctgca gcaggtgggc tggaagcttg cccagttcgc gcacaccatc      1200
cgcgtcgact tccagtaccg tggcctcgtc gccgccacgc tcgctgacct ggagccgttc      1260
atgctgcgac ggagggcga cggcgacacg gacgacgagc ccgaggtgat cgccgtaaac      1320
tcggtgtgcg agctgcaccg gctgctcgcg cagcccggta cactcgacaa ggtcctgggc      1380
accgtgcgcg cggtgcggcc gaggatcgtg acggtggtgg agcaggaggc caaccacaac      1440
tccggcacat tcctcgaccg cttcacggag tcgctgcact actactctac catgttcgac      1500
tccctcgagg gcgccggctc cggctccggc cagcccaccg acgcctcctc ccggccgcg      1560 gccggcggca cggaccaggt gatgtccgag gtgtacctcg gcggcagat ctgcaacatc      1620 gtggcgtgcg agggcgccga gcgcacggag cgccacgaga cgctggtcca gtggcgcggc      1680
cgcctcggcg ggtccgggtt cgagcccgtg cacctgggct ccaacgccta caagcaggca      1740
agcacgctgc tggccctctt cgccggcggc gacgggtaca gggtggagaa gaaggacggg      1800
tgcctgactc tgggatggca tacgcgcccg ctcatcgcca cctcggcgtg gcgcgtcgcc      1860
gctccgtga                                                             1869
```

<210> SEQ ID NO 5
<211> LENGTH: 622
<212> TYPE: PRT
<213> ORGANISM: Zea mays

<400> SEQUENCE: 5

```
Met Lys Arg Glu Tyr Gln Asn Ala Gly Gly Ser Asp Gly Tyr Met Gly
  1               5                  10                  15

Ser Ser Lys Asp Lys Ser Met Ala Ala Ala Gly Ala Gly Glu Gln
             20                  25                  30

Glu Glu Glu Val Asp Glu Leu Leu Ala Ala Leu Gly Tyr Lys Val Arg
         35                  40                  45

Ser Ser Asp Met Ala Asp Val Ala Gln Lys Leu Glu Gln Leu Glu Met
     50                  55                  60

Ala Met Gly Met Gly Gly Ala Cys Pro Thr Ala Asp Asp Gly Phe Val
 65                  70                  75                  80

Ser His Leu Ala Thr Asp Thr Val His Tyr Asn Pro Ser Asp Leu Ser
                 85                  90                  95

Ser Trp Val Glu Ser Met Leu Ser Glu Leu Asn Thr Pro Pro Pro
            100                 105                 110

Leu Pro Pro Ala Thr Pro Ala Pro Arg Leu Ala Ser Thr Ser Ser Thr
        115                 120                 125

Val Thr Ser Gly Ala Ala Ala Gly Ala Gly Tyr Phe Asp Leu Pro Pro
    130                 135                 140

Ala Val Asp Ser Ser Ser Ser Thr Tyr Ala Leu Lys Pro Ile Pro Ser
145                 150                 155                 160

Pro Val Ala Ala Ala Ser Ala Asp Pro Ser Asp Ser Ala Arg Glu
                165                 170                 175

Pro Lys Arg Met Arg Thr Gly Gly Gly Ser Thr Ser Ser Ser Ser
            180                 185                 190

Ser Ser Ser Ser Met Asp Gly Gly Arg Thr Arg Ser Ser Val Val Glu
        195                 200                 205
```

```
Ala Ala Pro Pro Ala Thr Gln Ala Ala Asn Gly Pro Ala Val Pro Val
    210                 215                 220

Val Val Val Asp Thr Gln Glu Ala Gly Ile Arg Leu Val His Ala Leu
225                 230                 235                 240

Leu Ala Cys Ala Glu Ala Val Gln Gln Glu Asn Phe Ser Ala Ala Asp
                245                 250                 255

Ala Leu Val Lys Gln Ile Pro Val Leu Ala Ser Ser Gln Gly Gly Ala
            260                 265                 270

Met Arg Lys Val Ala Ala Tyr Phe Gly Glu Ala Leu Ala Arg Arg Val
        275                 280                 285

Tyr Arg Leu Arg Pro Ala Pro Asp Gly Ser Leu Leu Asp Ala Ala Phe
    290                 295                 300

Ala Asp Leu Leu His Ala His Phe Tyr Glu Ser Cys Pro Tyr Leu Lys
305                 310                 315                 320

Phe Ala His Phe Thr Ala Asn Gln Ala Ile Leu Glu Ala Phe Ala Gly
                325                 330                 335

Cys Arg Arg Val His Val Val Asp Phe Gly Ile Lys Gln Gly Met Gln
            340                 345                 350

Trp Pro Ala Leu Leu Gln Ala Leu Ala Leu Arg Pro Gly Gly Pro Pro
        355                 360                 365

Ser Phe Arg Leu Thr Gly Val Gly Pro Pro Gln Pro Asp Glu Thr Asp
    370                 375                 380

Ala Leu Gln Gln Val Gly Trp Lys Leu Ala Gln Phe Ala His Thr Ile
385                 390                 395                 400

Arg Val Asp Phe Gln Tyr Arg Gly Leu Val Ala Ala Thr Leu Ala Asp
                405                 410                 415

Leu Glu Pro Phe Met Leu Arg Pro Glu Gly Asp Gly Thr Asp
            420                 425                 430

Glu Pro Glu Val Ile Ala Val Asn Ser Val Cys Glu Leu His Arg Leu
        435                 440                 445

Leu Ala Gln Pro Gly Thr Leu Asp Lys Val Leu Gly Thr Val Arg Ala
    450                 455                 460

Val Arg Pro Arg Ile Val Thr Val Val Glu Gln Glu Ala Asn His Asn
465                 470                 475                 480

Ser Gly Thr Phe Leu Asp Arg Phe Thr Glu Ser Leu His Tyr Tyr Ser
                485                 490                 495

Thr Met Phe Asp Ser Leu Glu Gly Ala Gly Ser Gly Ser Gly Gln Pro
            500                 505                 510

Thr Asp Ala Ser Ser Pro Ala Ala Ala Gly Gly Thr Asp Gln Val Met
        515                 520                 525

Ser Glu Val Tyr Leu Gly Arg Gln Ile Cys Asn Ile Val Ala Cys Glu
    530                 535                 540

Gly Ala Glu Arg Thr Glu Arg His Glu Thr Leu Val Gln Trp Arg Gly
545                 550                 555                 560

Arg Leu Gly Gly Ser Gly Phe Glu Pro Val His Leu Gly Ser Asn Ala
                565                 570                 575

Tyr Lys Gln Ala Ser Thr Leu Leu Ala Leu Phe Ala Gly Gly Asp Gly
            580                 585                 590

Tyr Arg Val Glu Lys Lys Asp Gly Cys Leu Thr Leu Gly Trp His Thr
        595                 600                 605

Arg Pro Leu Ile Ala Thr Ser Ala Trp Arg Val Ala Ala Pro
    610                 615                 620
```

<210> SEQ ID NO 6
<211> LENGTH: 1866
<212> TYPE: DNA
<213> ORGANISM: Zea mays

<400> SEQUENCE: 6

| | | | | | |
|---|---|---|---|---|---|
| atgaagcgcg | agtaccaaaa | cgccggcggg | agcgacggct | acatggggtc | ctccaaggac | 60 |
| aagtcgatgg | cggcggcggc | gggggcaggg | gagcaggagg | aggaggtgga | cgagctgctg | 120 |
| gcggcgctcg | ggtacaaggt | gcgttcgtcg | gatatggcgg | acgtcgcgca | gaagctagag | 180 |
| cagctcgaga | tggccatggg | gatggcggc | gcctgcccca | ccgctgatga | cgggttcgtc | 240 |
| tcgcacctcg | ccacggacac | cgtgcactac | aatccctccg | acctgtcgtc | ctgggtcgag | 300 |
| agcatgctat | ccgagctcaa | cacgcccccg | ccgccgctcc | cgcccgcgac | gccggcacca | 360 |
| aggctcgcgt | ccacctcgtc | caccgtcaca | agtggcgccg | ccgccggtgc | cggctacttc | 420 |
| gatctcccgc | ccgccgtcga | ctcgtccagc | agtacctacg | ctctgaagcc | gatcccctcg | 480 |
| ccggtggcgg | cggcgtcggc | cgacccgtcc | ccggactcgg | cgcgggagcc | caagcggatg | 540 |
| cgaactggcg | gcggcagcac | gtcgtcgtcc | tcttcctcgt | cgtcatccat | ggacggcggc | 600 |
| cgcactagga | gctccgtggt | cgaagctgcc | ccgccggcga | cgcaggcggc | caacgggccc | 660 |
| gcggtgccgg | tggtggtggt | ggacacgcag | gaggccggta | tccggctggt | gcacgcgctg | 720 |
| ctggcgtgcg | cggaggccgt | gcagcaggag | aacttctctg | cggcggacgc | gctggtgaag | 780 |
| cagatccccg | tgctggcctc | gtcgcagggc | ggcgccatgc | gcaaggtcgc | cgcctacttc | 840 |
| ggcgaggcgc | tcgcccggcg | cgtgtatcgc | ctccgcccgg | caccggacgg | ctcccctcctc | 900 |
| gacgccgcct | tcgccgacct | cctgcacgcg | cacttctacg | agtcctgccc | ctacctcaag | 960 |
| ttcgcccact | tcaccgcgaa | ccaggccatc | ctcgaggctt | tcgccgggtg | ccgccgcgtc | 1020 |
| cacgtcgtcg | acttcggcat | caagcagggg | atgcagtggc | cggctctcct | ccaggccctc | 1080 |
| gccctccgcc | ccgtggcccc | ccgtcgttc | cgtctcaccg | gcgtaggccc | gccgcagccc | 1140 |
| gacgagaccg | acgccctgca | gcaggtgggc | tggaagcttg | cccagttcgc | gcacaccatc | 1200 |
| cgcgtcgact | tccagtaccg | tggcctcgtc | gccgccacgc | tcgctgacct | ggagccgttc | 1260 |
| atgctgcgac | cggagggcga | cggcgacacg | gacgacgagc | ccgaggtgat | cgccgtaaac | 1320 |
| tcggtgtgcg | agctgcaccg | gctgctcgcg | cagcccggta | cactcgacaa | ggtcctgggc | 1380 |
| accgtgcgcg | cggtgcggcc | gaggatcgtg | acggtggtgg | agcaggaggc | caaccacaac | 1440 |
| tccggcacat | tcctcgaccg | cttcacggag | tcgctgcact | actactctac | catgttcgac | 1500 |
| tccctcgagg | gcgccggctc | cggctccggc | cagcccaccg | acgcctcctc | ccggccgcg | 1560 |
| gccggcggca | cggaccaggt | gatgtccgag | gtgtacctcg | gcggcagat | ctgcaacatc | 1620 |
| gtggcgtgcg | agggcgccga | gcgcacggag | cgccacgaga | cgctggtcca | gtggcgcggc | 1680 |
| cgcctcggcg | ggtccgggtt | cgagcccgtg | cacctgggct | ccaacgccta | caagcaggca | 1740 |
| agcacgctgc | tggcccctctt | cgccggcggc | gacgggtaca | gggtggagaa | gaaggacggg | 1800 |
| tgcctgactc | tgggatggca | tacgcgcccg | ctcatcgcca | cctcggcgtg | gcgcgtcgcc | 1860 |
| gctccg | | | | | | 1866 |

<210> SEQ ID NO 7
<211> LENGTH: 15
<212> TYPE: PRT
<213> ORGANISM: Zea mays
<220> FEATURE:
<223> OTHER INFORMATION: indel sequence

```
<400> SEQUENCE: 7

Ser Gly Ser Gly Ser Gly Gln Pro Thr Asp Ala Ser Pro Pro Ala
 1               5                  10                  15

<210> SEQ ID NO 8
<211> LENGTH: 11
<212> TYPE: PRT
<213> ORGANISM: Zea mays
<220> FEATURE:
<223> OTHER INFORMATION: indel sequence

<400> SEQUENCE: 8

Gln Pro Thr Asp Ala Ser Ser Pro Ala Ala Gly
 1               5                  10
```